United States Patent
Laporte et al.

(10) Patent No.: US 10,647,986 B2
(45) Date of Patent: May 12, 2020

(54) DYNAMIN 2 INHIBITOR FOR THE TREATMENT OF CENTRONUCLEAR MYOPATHIES

(71) Applicants: UNIVERSITE DE STRASBOURG, Strasbourg (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR)

(72) Inventors: Jocelyn Laporte, Strasbourg (FR); Belinda Cowling, Kaltenhouse (FR); Hichem Tasfaout, Illkirch-Grafenstaden (FR)

(73) Assignees: UNIVERSITE DE STRASBOURG, Strasbourg (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR)

(*) Notice: Subject to any disclaimer, the term of this patent is extended or adjusted under 35 U.S.C. 154(b) by 152 days.

(21) Appl. No.: 15/030,127

(22) PCT Filed: Oct. 20, 2014

(86) PCT No.: PCT/EP2014/072466
§ 371 (c)(1),
(2) Date: Apr. 18, 2016

(87) PCT Pub. No.: WO2015/055859
PCT Pub. Date: Apr. 23, 2015

(65) Prior Publication Data
US 2016/0264976 A1 Sep. 15, 2016

(30) Foreign Application Priority Data

Oct. 18, 2013 (EP) ..................................... 13306440

(51) Int. Cl.
*C12N 15/113* (2010.01)
*G01N 33/50* (2006.01)

(52) U.S. Cl.
CPC .. *C12N 15/1137* (2013.01); *C12Y 306/05005* (2013.01); *G01N 33/5061* (2013.01); *C12N 2310/11* (2013.01); *C12N 2310/12* (2013.01); *C12N 2310/14* (2013.01); *C12N 2320/30* (2013.01); *G01N 2333/914* (2013.01)

(58) Field of Classification Search
None
See application file for complete search history.

(56) References Cited

U.S. PATENT DOCUMENTS

2011/0123436 A1* 5/2011 Chang .............. A61K 47/48561
424/1.11

FOREIGN PATENT DOCUMENTS

WO     WO099062494 A2 * 12/1999
WO     WO 2013/006558      1/2013

OTHER PUBLICATIONS

Cowling, B.S. et al. "Increased Expression of Wild-Type or a Centronuclear Myopathy Mutant of Dynamin 2 in Skeletal Muscle of Adult Mice Leads to Structural Defects and Muscle Weakness" *The American Journal of Pathology*, May 1, 2011, pp. 2224-2235, vol. 178, No. 5.
Cowling, B.S. et al. "Reducing dynamin 2 expression rescues X-linked centronuclear myopathy" *The Journal of Clinical Investigation*, Mar. 3, 2014, pp. 1350-1363, vol. 124, No. 3.
Demonbreun, A.R. et al. "Dynamin 2 the rescue for centronuclear myopathy" *The Journal of Clinical Investigation*, Feb. 24, 2014, pp. 976-978, vol. 124, No. 3.
Durieux, A-C. et al. "A centronuclear myopathy-dynamin 2 mutation impairs skeletal muscle structure and function in mice" *Human Molecular Genetics*, Sep. 21, 2010, pp. 4820-4836, vol. 19, No. 24.
Tinelli, E. et al. "Muscle-specific function of the centronuclear myopathy and Charcot-Marie-Tooth neuropathy-associated dynamin 2 is required for proper lipid metabolism, mitochondria, muscle fibers, neuromuscular junctions and peripheral nerves" *Human Molecular Genetics*, Jun. 27, 2013, pp. 4417-4429, vol. 22, No. 21.
Written Opinion in International Application No. PCT/EP2014/072466, dated Feb. 2, 2015, pp. 1-6.
Tong, H. et al. "Dopamine D1 receptor inhibition of NMDA receptor currents mediated by tyrosine kinase-dependent receptor trafficking in neonatal rat striatum" *J Physiol.*, 2008, pp. 4693-4707, vol. 586, No. 19.
Sharma, M. et al. "Mega roles of microRNAs in regulation of skeletal muscle health and disease" *Frontiers in Physiology*, Jun. 26, 2014, pp. 1-9, vol. 5, Article 239.
Buono, S. et al. "Reducing dynamin 2 (DNM2) rescues DNM2-related dominant centronuclear myopathy" *PNAS*, pp. 11066-11071, Oct. 23, 2018, vol. 115, No. 43.

* cited by examiner

*Primary Examiner* — J. E Angell
(74) *Attorney, Agent, or Firm* — Saliwanchik, Lloyd & Eisenchenk

(57) ABSTRACT

The present disclosure relates to an inhibitor of Dynamin 2 for use in the treatment of centronuclear myopathies. The present disclosure relates to pharmaceutical compositions containing Dynamin 2 inhibitor and to their use for the treatment of centronuclear myopathies. It also deals with a method for identifying or screening molecules useful in the treatment of a centronuclear myopathy.

7 Claims, 25 Drawing Sheets
Specification includes a Sequence Listing.

A. Fibre size

B. Nuclei position

SEQUENCE LISTING

```
<160> NUMBER OF SEQ ID NOS: 31

<210> SEQ ID NO 1
<211> LENGTH: 3714
<212> TYPE: DNA
<213> ORGANISM: Homo sapiens

<400> SEQUENCE: 1
gaggtcgctc gggtcgggtg tcgcctgaga accggatgag gcggcgaccg tgaggccgag      60
ccgggagcgg gcgtcttgcc gaggcccggg cgggcgggga gcaacggcta cagacgccgc     120
ggggccaggt cgttgagggt cggcggcggg cgaggagcgc agggcgctcg ggccgggggc     180
cgccggcgcc atgggcaacc gcgggatgga agagctgatc ccgctggtca acaaactgca     240
ggacgccttc agctccatcg gccagagctg ccacctggac ctgccgcaga tcgctgtagt     300
gggcggccag agcgccggca agagctcggt gctggagaac ttcgtgggcc gggacttcct     360
tccccgcggt tcaggaatcg tcacccgcg gcctctcatt ctgcagctca tcttctcaaa      420
aacagaacat gccgagtttt tgcactgcaa gtccaaaaag tttacagact ttgatgaagt     480
ccggcaggag attgaagcag agaccgacag ggtcacgggg accaacaaag gcatctcccc     540
agtgcccatc aaccttcgag tctactcgcc acacgtgttg aacttgaccc tcatcgacct     600
cccgggtatc accaaggtgc ctgtgggcga ccagcctcca gacatcgagt accagatcaa     660
ggacatgatc ctgcagttca tcagccggga gagcagcctc attctggctg tcacgcccgc     720
caacatggac ctggccaact ccgacgccct caagctggcc aaggaagtcg atccccaagg     780
cctacggacc atcggtgtca tcaccaagct tgacctgatg gacgagggca ccgacgccag     840
ggacgtcttg gagaacaagt tgctcccgtt gagaagaggc tacattggcg tggtgaaccg     900
cagccagaag gatattgagg gcaagaagga catccgtgca gcactggcag ctgagaggaa     960
gttcttcctc tcccacccgg cctacggca catggccgac cgcatgggca cgccacatct    1020
gcagaagacg ctgaatcagc aactgaccaa ccacatccgg gagtcgctgc cggccctacg    1080
tagcaaacta cagagccagc tgctgtccct ggagaaggag gtggaggagt acaagaactt    1140
tcggcccgac gaccccaccc gcaaaaccaa agccctgctg cagatggtcc agcagtttgg    1200
ggtggatttt gagaagagga tcgagggctc aggagatcag gtggacactc tggagctctc    1260
cgggggcgcc cgaatcaatc gcatcttcca cgagcggttc ccatttgagc tggtgaagat    1320
ggagtttgac gagaaggact acgacggga gatcagctat gccattaaga catccatgg     1380 agtcaggacc gggctttcta cccccggactt ggcattcgag gccattgtga aaaagcaggt    1440
cgtcaagctg aaagagccct gtctgaaatg tgtcgacctg gttatccagg agctaatcaa    1500
tacagttagg cagtgtacca gtaagctcag ttcctacccc cggttgcgag aggagacaga    1560
gcgaatcgtc accacttaca tccgggaacg ggaggggaga acgaaggacc agattcttct    1620
gctgatcgac attgagcagt cctacatcaa cacgaaccat gaggacttca tcgggtttgc    1680
caactgttac tatactgagc agctggtgac ctgtgcccag cagaggagca cgcagctgaa    1740
caagaagaga gccatcccca tcaggggga gatcctggtg atccgcaggg gctggctgac    1800
```

```
catcaacaac atcagcctga tgaaaggcgg ctccaaggag tactggtttg tgctgactgc   1860
cgagtcactg tcctggtaca aggatgagga ggagaaagag aagaagtaca tgctgcctct   1920
ggacaacctc aagatccgtg atgtggagaa gggcttcatg tccaacaagc acgtcttcgc   1980
catcttcaac acggagcaga gaaacgtcta caaggacctg cggcagatcg agctggcctg   2040
tgactcccag gaagacgtgg acagctggaa ggcctcgttc ctccgagctg cgtctaccc    2100
cgagaaggac caggcagaaa cgaggatgg ggcccaggag aacaccttct ccatggaccc    2160
ccaactggag cggcaggtgg agaccattcg caacctggtg gactcatacg tggccatcat   2220
caacaagtcc atccgcgacc tcatgccaaa gaccatcatg cacctcatga tcaacaatac   2280
gaaggccttc atccaccacg agctgctggc ctacctatac tcctcggcag accagagcag   2340
cctcatggag gagtcggctg accaggcaca gcggcgggac gacatgctgc gcatgtacca   2400
tgccctcaag gaggcgctca acatcatcgg tgacatcagc accagcactg tgtccacgcc   2460
tgtaccccg cctgtcgatg cacctggct ccagagcgcc agcagccaca gcccactcc     2520
acagcgccga ccggtgtcca gcatacaccc ccctggccgg cccccagcag tgaggggccc   2580
cactccaggg ccccccctga ttcctgttcc cgtggggca gcagcctcct tctcggcgcc    2640
cccaatccca tcccggcctg accccagag cgtgtttgcc aacagtgacc tcttcccagc    2700
cccgcctcag atcccatctc ggccagttcg gatccccca gggattcccc caggagtgcc    2760
cagcagaaga ccccctgctg cgcccagccg gcccaccatt atccgcccag ccgagccatc   2820
cctgctcgac taggcctcga ggggggcgtg ctctcggggg ggcctcacgc acccgcggcg   2880
caggagcttc agtggtctgg ggcctccgc cgcccctatg ctgggaccag gctcccagtg    2940
ggcagccctg gcctcttcct taacgctggc cccggtccag ggccggcccc tgtgcctggc   3000
tggacaccgc actgcgcaaa ggggccctgg agctccaggc agggggcgct ggggtgttgc   3060
actttggggg atgagtctc agggtggcag aggggggacc agaacccttg acaccatcct   3120
gaatgagggg tccagcctgg ggggactct accaaggtct tcttgggctg ggaaagccca    3180
tgtagggcag gccttctata agtgcgggca ccaaggcgc ctacatcccc aggccttgct    3240
ggggtgcagg ggtatatcaa cttcccatta gcaggagctc cccagcggca agcctggccc   3300
agtgggctcg gtagtgccca gctggcaggc ctgaggtgta catagtcctt cccggccata   3360
ttaaccacac agcctgagcc tggcccagcc tcggctgcca gaggtgcctt tgctaggccc   3420
ggagccgttg gcccgggccg gccttgccct attcctctcc tcctcctcct cctgggtccc   3480
ccagggtggc tgggcttggg ctatgtgggt ggtggtggcg ggggtcttg ggggcctctc    3540
agctcccgcc catgcctccc tgatgggtgg gccagggcg gcctctctct gaggagacct    3600
cacccactcc tcgctcagtt tgaccactgt aagtgcctgc actctgtatt ctattaataa   3660
actaaaataa agggaagacg ctgctggtgg ctgctgaaaa aaaaaaaaa aaaa           3714
```

<210> SEQ ID NO 2
<211> LENGTH: 23
<212> TYPE: DNA
<213> ORGANISM: artificial sequence
<220> FEATURE:
<223> OTHER INFORMATION: iRNA

<400> SEQUENCE: 2
aaggacatga tcctgcagtt cat                                             23

<210> SEQ ID NO 3

```
<211> LENGTH: 23
<212> TYPE: DNA
<213> ORGANISM: artificial sequence
<220> FEATURE:
<223> OTHER INFORMATION: iRNA

<400> SEQUENCE: 3
aagaggctac attggcgtgg tga                                              23

<210> SEQ ID NO 4
<211> LENGTH: 23
<212> TYPE: DNA
<213> ORGANISM: artificial sequence
<220> FEATURE:
<223> OTHER INFORMATION: iRNA

<400> SEQUENCE: 4
aggtggacac tctggagctc tcc                                              23

<210> SEQ ID NO 5
<211> LENGTH: 23
<212> TYPE: DNA
<213> ORGANISM: artificial sequence
<220> FEATURE:
<223> OTHER INFORMATION: iRNA

<400> SEQUENCE: 5
aagaagtaca tgctgcctct gga                                              23

<210> SEQ ID NO 6
<211> LENGTH: 23
<212> TYPE: DNA
<213> ORGANISM: artificial sequence
<220> FEATURE:
<223> OTHER INFORMATION: iRNA

<400> SEQUENCE: 6
aacgtctaca aggacctgcg gca                                              23

<210> SEQ ID NO 7
<211> LENGTH: 23
<212> TYPE: DNA
<213> ORGANISM: artificial sequence
<220> FEATURE:
<223> OTHER INFORMATION: iRNA

<400> SEQUENCE: 7
aggagaacac cttctccatg gac                                              23

<210> SEQ ID NO 8
<211> LENGTH: 21
<212> TYPE: DNA
<213> ORGANISM: artificial sequence
<220> FEATURE:
<223> OTHER INFORMATION: iRNA

<400> SEQUENCE: 8
aactgttact atactgagca g                                                21

<210> SEQ ID NO 9
<211> LENGTH: 19
<212> TYPE: DNA
<213> ORGANISM: artificial sequence
<220> FEATURE:
<223> OTHER INFORMATION: iRNA

<400> SEQUENCE: 9
```
tgccaactgt tactatact                                                19

<210> SEQ ID NO 10
<211> LENGTH: 19
<212> TYPE: DNA
<213> ORGANISM: artificial sequence
<220> FEATURE:
<223> OTHER INFORMATION: iRNA

<400> SEQUENCE: 10
gaagagctga tcccgctgg                                                19

<210> SEQ ID NO 11
<211> LENGTH: 19
<212> TYPE: DNA
<213> ORGANISM: artificial sequence
<220> FEATURE:
<223> OTHER INFORMATION: iRNA

<400> SEQUENCE: 11
gcacgcagct gaacaagaa                                                19

<210> SEQ ID NO 12
<211> LENGTH: 19
<212> TYPE: DNA
<213> ORGANISM: artificial sequence
<220> FEATURE:
<223> OTHER INFORMATION: iRNA

<400> SEQUENCE: 12
ggacttacga cgggagatc                                                19

<210> SEQ ID NO 13
<211> LENGTH: 19
<212> TYPE: DNA
<213> ORGANISM: artificial sequence
<220> FEATURE:
<223> OTHER INFORMATION: iRNA

<400> SEQUENCE: 13
ggatattgag ggcaagaag                                                19

<210> SEQ ID NO 14
<211> LENGTH: 19
<212> TYPE: DNA
<213> ORGANISM: artificial sequence
<220> FEATURE:
<223> OTHER INFORMATION: iRNA

<400> SEQUENCE: 14
ggaccaggca gaaaacgag                                                19

<210> SEQ ID NO 15
<211> LENGTH: 19
<212> TYPE: DNA
<213> ORGANISM: artificial sequence
<220> FEATURE:
<223> OTHER INFORMATION: iRNA

<400> SEQUENCE: 15
gcgaatcgtc accacttac                                                19

<210> SEQ ID NO 16
<211> LENGTH: 20
<212> TYPE: DNA

```
<213> ORGANISM: artificial sequence
<220> FEATURE:
<223> OTHER INFORMATION: shRNA

<400> SEQUENCE: 16
aaccgcggga tggaagagct                                                  20

<210> SEQ ID NO 17
<211> LENGTH: 21
<212> TYPE: DNA
<213> ORGANISM: artificial sequence
<220> FEATURE:
<223> OTHER INFORMATION: shRNA

<400> SEQUENCE: 17
aacttgaccc tcatcgacct c                                                21

<210> SEQ ID NO 18
<211> LENGTH: 19
<212> TYPE: DNA
<213> ORGANISM: artificial sequence
<220> FEATURE:
<223> OTHER INFORMATION: shRNA

<400> SEQUENCE: 18
tcggtgtcat caccaagct                                                   19

<210> SEQ ID NO 19
<211> LENGTH: 19
<212> TYPE: DNA
<213> ORGANISM: artificial sequence
<220> FEATURE:
<223> OTHER INFORMATION: shRNA

<400> SEQUENCE: 19
tgccaactgt ttctatact                                                   19

<210> SEQ ID NO 20
<211> LENGTH: 21
<212> TYPE: DNA
<213> ORGANISM: artificial sequence
<220> FEATURE:
<223> OTHER INFORMATION: shRNA

<400> SEQUENCE: 20
aactgtttct atactgagga g                                                21

<210> SEQ ID NO 21
<211> LENGTH: 21
<212> TYPE: DNA
<213> ORGANISM: artificial sequence
<220> FEATURE:
<223> OTHER INFORMATION: shRNA

<400> SEQUENCE: 21
tttctatact gaggagctgg t                                                21

<210> SEQ ID NO 22
<211> LENGTH: 19
<212> TYPE: DNA
<213> ORGANISM: artificial sequence
<220> FEATURE:
<223> OTHER INFORMATION: shRNA

<400> SEQUENCE: 22
gcacgcagct gaacaagaa                                                   19
```

<210> SEQ ID NO 23
<211> LENGTH: 23
<212> TYPE: DNA
<213> ORGANISM: artificial sequence
<220> FEATURE:
<223> OTHER INFORMATION: shRNA

<400> SEQUENCE: 23
aagaagtaca tgctgcctct gga                                           23

<210> SEQ ID NO 24
<211> LENGTH: 20
<212> TYPE: DNA
<213> ORGANISM: artificial sequence
<220> FEATURE:
<223> OTHER INFORMATION: shRNA

<400> SEQUENCE: 24
aacaccttct ccatggaccc                                               20

<210> SEQ ID NO 25
<211> LENGTH: 21
<212> TYPE: DNA
<213> ORGANISM: artificial sequence
<220> FEATURE:
<223> OTHER INFORMATION: shRNA

<400> SEQUENCE: 25
ccattatccg cccagccgag c                                             21

<210> SEQ ID NO 26
<211> LENGTH: 30
<212> TYPE: DNA
<213> ORGANISM: artificial sequence
<220> FEATURE:
<223> OTHER INFORMATION: antisense RNA

<400> SEQUENCE: 26
gtcacccgga ggcctctcat tctgcagctc                                    30

<210> SEQ ID NO 27
<211> LENGTH: 33
<212> TYPE: DNA
<213> ORGANISM: artificial sequence
<220> FEATURE:
<223> OTHER INFORMATION: antisense RNA

<400> SEQUENCE: 27
acacactaga gttgtctggt ggagcccgca tca                                33

<210> SEQ ID NO 28
<211> LENGTH: 20
<212> TYPE: DNA
<213> ORGANISM: artificial sequence
<220> FEATURE:
<223> OTHER INFORMATION: forward DNM2 primer

<400> SEQUENCE: 28
ccaacaaagg catctcccct                                               20

<210> SEQ ID NO 29
<211> LENGTH: 20
<212> TYPE: DNA
<213> ORGANISM: artificial sequence
<220> FEATURE:

```
<223> OTHER INFORMATION: reverse DNM2 primer

<400> SEQUENCE: 29
tggtgagtag acccgaaggt                                                   20

<210> SEQ ID NO 30
<211> LENGTH: 30
<212> TYPE: DNA
<213> ORGANISM: artificial sequence
<220> FEATURE:
<223> OTHER INFORMATION: mRNA

<400> SEQUENCE: 30
ctgttactat actgagcagc tggtgacctg                                        30

<210> SEQ ID NO 31
<211> LENGTH: 10
<212> TYPE: PRT
<213> ORGANISM: Homo sapiens

<400> SEQUENCE: 31

Cys Tyr Tyr Thr Glu Gln Leu Val Thr Cys
1               5                   10
```

DYNAMIN 2 INHIBITOR FOR THE TREATMENT OF CENTRONUCLEAR MYOPATHIES

FIELD OF THE INVENTION

The present disclosure relates to an inhibitor of Dynamin 2 for use in the treatment of centronuclear myopathies. The present disclosure also relates to pharmaceutical compositions containing Dynamin 2 inhibitor and to their use for the treatment of centronuclear myopathies.

BACKGROUND OF THE INVENTION

Centronuclear Myopathies (CNM) are a group of congenital myopathies characterized by muscle weakness and confirmed histologically by fiber atrophy, predominance of type I fibers, and increased centralization of nuclei, not secondary to muscle regeneration. Three main forms of CNM have been characterized: X-linked CNM (XLCNM also called myotubular myopathy, OMIM 310400) due to mutations in the phosphoinositides phosphatase myotubularin (MTM1) (Laporte, J. et al., Nature Genetics, 1996. 13(2): p. 175-82), autosomal recessive CNM (ARCNM, OMIM 255200) caused by mutations in the membrane remodeling protein amphiphysin 2 (BIN1) (Nicot, A. S. et al., Nature Genetics, 2007. 39(9): p. 1134-9), and autosomal dominant CNM (ADCNM, OMIM 160150) due to mutations in dynamin 2 (DNM2) (Bitoun, M. et al., Nature Genetics, 2005. 37(11): p. 1207-9) or due to mutations in other genes, such as BIN1 (Bohm et al., Brain. 2014 Sep. 25. pii: awu272. [Epub ahead of print]). Other genes have been linked to a CNM-like myopathy: RYR1 encoding for the ryanodine receptor, TTN encoding for Titin, CCDC78 (OMIM 614807) and the phosphoinositides phosphatase MTMR14 (called hJUMPY; OMIM 160150). The genetic relationship between the implicated genes is not known and potent therapeutic approaches are lacking.

X-linked centronuclear myopathy, also called myotubular myopathy, is the most common and severe form of CNM, with neonatal onset and death often occurring in the first years of life (Jungbluth, H. et al., Orphanet J Rare Dis, 2008. 3: p. 26). There is currently no cure, nor effective treatments available for this disorder. To date more than 200 different mutations in MTM1 have been reported in about 450 families, most of which lead to a strong reduction of protein. Mtm1 knockout or knockin mice have previously been characterized, which recapitulate the CNM phenotype with classical histological features including abnormal organelle positioning, mislocalization of nuclei and muscle atrophy, associated with a corresponding reduction in muscle strength. A defect in triads structure associated with abnormal excitation-contraction coupling has been detected in several animal models and patients with different forms of CNM, identifying a common defect in all CNM forms (Defects in amphiphysin 2 (BIN1) and triads in several forms of centronuclear myopathies, Toussaint A. et al., Acta Neuropathol. 2011 February; 121(2):253-66). This is consistent with a proposed role of MTM1 in the regulation of phosphoinositides level on the sarcoplasmic reticulum component of the triads.

Dynamins are large GTPase proteins that play important roles in membrane trafficking and endocytosis, and in actin cytoskeleton assembly. Dynamin proteins contain an N-terminal GTPase domain, middle domain, PH domain (phosphoinositide binding), GED (GTPase effector domain), and a PRD (Proline-rich domain) for protein-protein interactions. Three human dynamins have been identified; dynamin 1, expressed exclusively in neurons, dynamin 3 predominantly in brain and testis, and dynamin 2 (DNM2) which is ubiquitously expressed. Different heterozygous DNM2 mutations have been identified in tissue-specific diseases: Autosomal Dominant Centronuclear Myopathy which affects skeletal muscle, and autosomal dominant Charcot-Marie-Tooth (CMTDIB, OMIM 606482) peripheral neuropathy.

Recent biochemical studies have suggested that some CNM-causing DNM2 mutations increase the dynamin oligomer stability and GTPase activity. This was complemented in vivo by either knockin or over-expression of the most common CNM-DNM2 patient mutation (p.R465W) in mice, which induced CNM-like features in adult mice, indicating the disease is not due to haploinsufficiency. Over-expression of wild type (WT) DNM2 also caused perturbation to the muscle, albeit to a lesser extent.

The patent application WO 2013/0065558 describes that miR-133a plays a modulatory role on DNM2 expression. As DNM2 is mutated in CNM, it is stated that an agonist of a miR-133 family member might be beneficial for the treatment of centronuclear myopathy. However, miR-133 has numerous targets (see online databases for miRNA target prediction and functional annotations, such as http://mird-b.org/miRDB/ where 226 predicted targets for hsa-miR-133a in miRDB are given and none of them is DNM2, the same types of results are obtained with other online databases). Since miR-133 has numerous targets and is therefore not selective, it could have deleterious effects. Moreover, improvement of CNM with miR133 delivery has not been reported so far.

Accordingly, there is a significant need for an appropriate centronuclear myopathy treatment, in particular for new and more effective therapeutic agents.

SUMMARY OF THE INVENTION

The search for promising therapies of centronuclear myopathies led the inventors to the discovery that downregulation of DNM2 can prevent, stop and potentially overturn the progression of the XLCNM phenotype. Moreover, it was identified that MTM1 acts as a negative regulator of DNM2 in muscle organization and force. While DNM2 is a key mechanoenzyme for important cellular processes, its reduction is strongly beneficial for XLCNM and other centronuclear myopathies and thus represents a novel potential therapeutic approach. The work presented here demonstrates that downregulation of DNM2 has a potent therapeutic impact on centronuclear myopathies.

In a first aspect, the present invention concerns an inhibitor of Dynamin 2 for use in the treatment of centronuclear myopathies. In a particular embodiment, the centronuclear myopathy is selected from the group consisting of X-linked CNM (XLCNM), autosomal recessive CNM (ARCNM), and autosomal dominant CNM (ADCNM). In a preferred embodiment, the centronuclear myopathy is XLCNM or ARCNM.

The present invention also concerns a pharmaceutical composition comprising an inhibitor of Dynamin 2 and a pharmaceutically acceptable carrier/excipient for use in the treatment of a centronuclear myopathy.

The present invention further concerns a method for the treatment of a centronuclear myopathy, wherein the method comprises the step of administering into a subject in need of such treatment a therapeutically efficient amount of a Dynamin 2 inhibitor.

Finally, the present invention concerns the use of a Dynamin 2 inhibitor for the preparation of a pharmaceutical composition for the treatment of a centronuclear myopathy.

The Dynamin 2 inhibitor is preferably selected from the group consisting of an antibody directed against Dynamin 2, a nucleic acid molecule interfering specifically with Dynamin 2 expression, and a small molecule inhibiting the Dynamin 2 activity, expression or function. In a preferred embodiment, the Dynamin 2 inhibitor is selected from the group consisting of a nucleic acid molecule interfering specifically with Dynamin 2 expression. In a particular embodiment, the Dynamin 2 inhibitor is a RNAi, an antisense nucleic acid or a ribozyme interfering specifically with Dynamin 2 expression.

In a more specific embodiment, the Dynamin 2 inhibitor is a siRNA, shRNA or an antisense snRNA.

A further object of the invention relates to a method of screening for or identifying compounds useful for the treatment of centronuclear myopathies comprising:

a) Providing or obtaining a candidate compound; and b) Determining whether said candidate compound inhibits the activity/expression of Dynamin 2, c) Selecting said candidate compound if it inhibits the activity/expression of Dynamin 2.

The method for screening or identifying a molecule suitable for the treatment of centronuclear myopathies can optionally further comprise the step of administering in vivo or in vitro selected molecule in a centronuclear myopathy non-human animal model or a part thereof (tissue or cells) and analyzing the effect on the myopathy onset or progression.

These and other objects and embodiments of the invention will become more apparent after the detailed description of the invention.

DETAILED DESCRIPTION

Unless otherwise defined, all technical and scientific terms used herein have the same meaning as commonly understood by one of ordinary skill in the art to which this invention belongs.

The Dynamin 2 is encoded by the DNM2 gene (Gene ID 1785). More precisely, the DNM2 gene is located from base pair 10,919,884 to base pair 10,942,586 on chromosome 19 (GRCh37/hg19 release) or from 10,718,053 to 10,831,910 base pairs on the NC_000019.10 location (GRCh38/hg19). The dynamin 2 gene or gene products are also known by other names, including but not limited to CMTDI1, CMTDIB, DI-CMTB, DYN2, DYN2_HUMAN, dynamin II, DYNII.

Dynamin 2 Inhibitors

As used herein, the term "Dynamin 2 inhibitor" refers to any molecule able to decrease specifically the expression of Dynamin 2 or inhibit the Dynamin 2 activity or function. Preferably, such a Dynamin 2 inhibitor is a direct inhibitor, meaning that it interacts directly with either the Dynamin 2 protein or a nucleic acid encoding said Dynamin 2 or a part thereof. The Dynamin 2 inhibitors according to the invention are capable of inhibiting or decreasing the functional activity of Dynamin 2 in vivo and/or in vitro. The inhibitor may inhibit the functional activity of Dynamin 2 by at least about 30%, preferably by at least about 50%, preferably by at least about 70, 75 or 80%, still preferably by 85, 90, or 95%. In particular, the inhibitor may inhibit Dynamin 2 expression by at least about 10%, preferably by at least about 30%, preferably by at least about 50%, preferably by at least about 70, 75 or 80%, still preferably by 85, 90, or 95%.

A Dynamin 2 inhibitor of the invention may act by blocking and/or inhibiting the activity or function of Dynamin 2. This may for example be achieved by inhibiting the enzymatic activity of Dynamin 2. Functional or enzymatic activity of Dynamin 2 may be readily assessed by one skilled in the art according to known methods by testing for example the GTPase activity or the function of Dynamin 2 in clathrin-mediated endocytosis (Macia E. et al., Dynasore, a cell-permeable inhibitor of dynamin: Developmental cell 10, 839-850, June 2006). For inhibitors of GTPase activity or lipid binding, subcellular localization, clathrin mediated endocytosis, synaptic vesicle endocytosis, one can use the method described in McCluskey et al, Traffic, 2013; McGeachie et al, ACS Chem Biol, 2013. For Dynamin 2 GTPase activity, oligomerisation, lipid binding, one can use the methods described in Wang et al J Biol Chem 2010; or Kenniston and Lemmon, Embo J, 2010.

Figure 1:
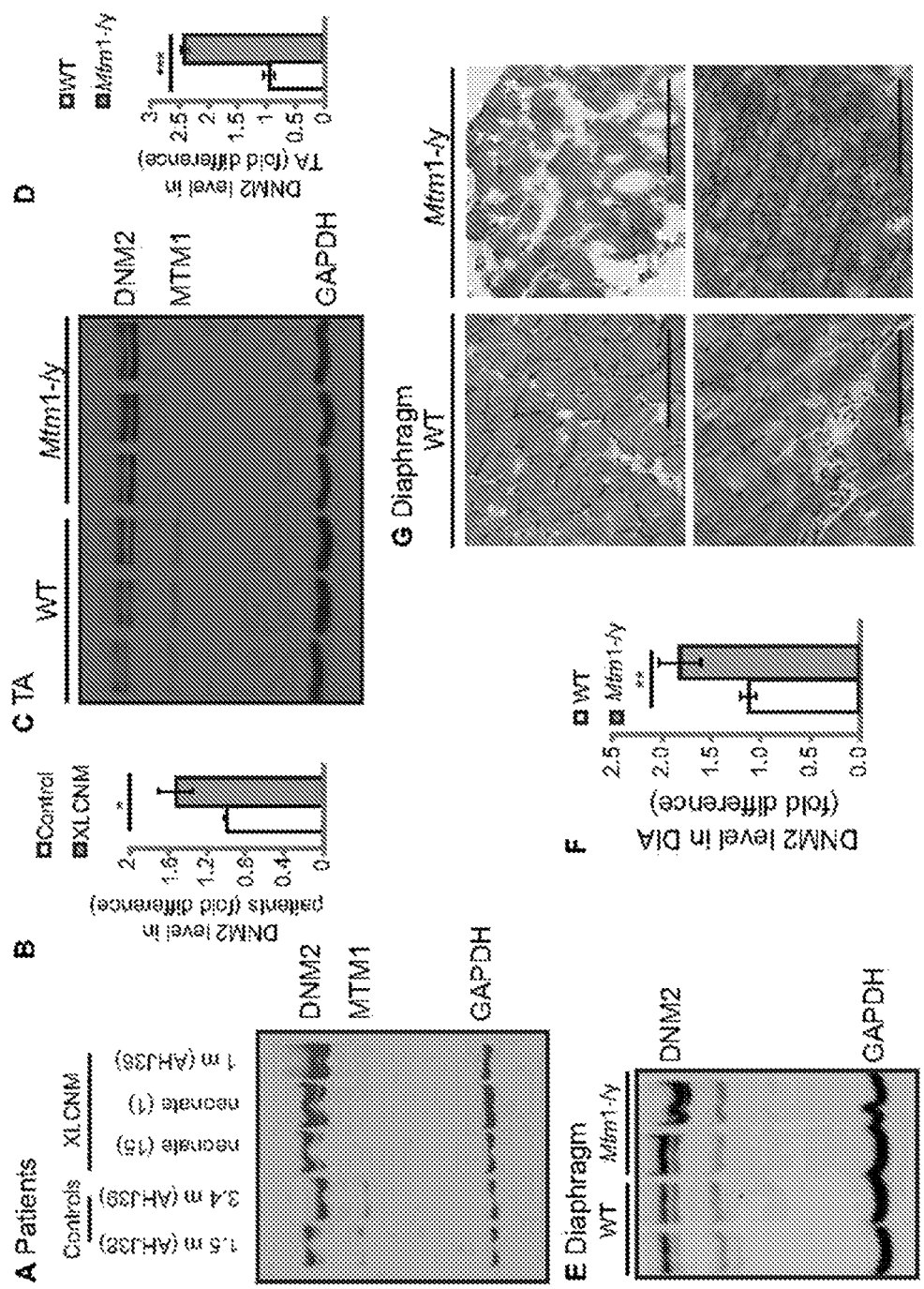
FIG. 1. DNM2 levels in XLCNM. (A) Representative WB of XLCNM patient muscle lysates for DNM2, MTM1, and GAPDH loading control, m=months of age. (B) Relative level of DNM2 protein expression determined by densitometry, standardized to GAPDH loading control, total n=3-5 patients. (C) Tibialis anterior (TA) and diaphragm (E) skeletal muscle lysates from 5 week old WT and Mtm1−/y mice were immunoblotted for DNM2 and GAPDH (loading control). Relative level of DNM2 protein determined by densitometry of DNM2 immunoreactive polypeptides, standardized to GAPDH loading, for TA (D) and diaphragm (F). DNM2 expression is represented as fold difference from WT control lysate, n=4 mice. (G) Diaphragm muscle sections were stained for HE. Scale bar 100 mm. All graphs depict mean±s.e.m. ($*p<0.05$, $p<0.01$, $*p<0.001$).
Figure 2:
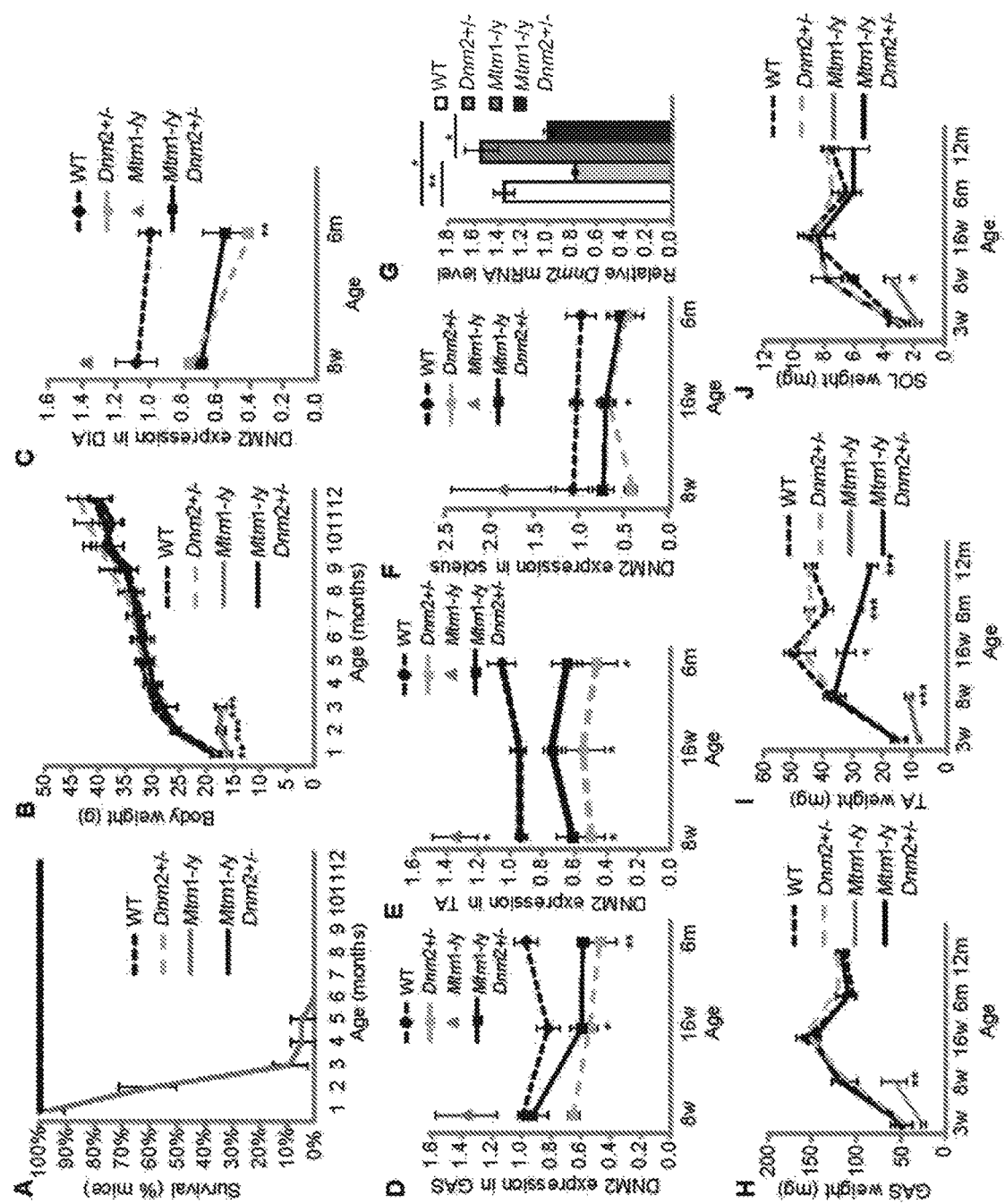
FIG. 2. Reduced DNM2 expression greatly rescues the lifespan of Mtm1−/y mice. (A) Lifespan of all mice, represented as percentage (%) survival of mice. All mice in groups WT, Dnm2+/−, and Mtm1−/yDnm2+/− survived to 12 months of age. The oldest mice reached 2 years of age. (B) Whole body weight of all mice is depicted. Only Mtm1−/y mice exhibit a significant reduction in body weight. (C) Relative level of DNM2 protein was determined by densitometry of DNM2-immunoreactive polypeptides, standardized to GAPDH loading. DNM2 level is represented as fold difference from WT control lysate. Expression was determined in 8, 16 weeks old and 6 month old mice from diaphragm (DIA) (C), gastrocnemius (GAS) (D), tibialis anterior (TA) (E), and soleus (SOL) (F) muscles, n=2-8 mice. mRNA levels were quantified by qRT-PCR analysis, with DNM2 levels expressed relative to GAPDH loading control (G). Graph represents 3 independent experiments. GAS (H), TA (I), and SOL (J) muscle weights (n=5-13 mice). All graphs depict mean±s.e.m. ($*p<0.05$, $p<0.01$, $*p<0.001$) (w=weeks of age, m=months of age).

The Dynamin 2 inhibitor of the invention may also act by blocking and/or inhibiting the Dynamin 2 expression (including transcription, splicing, transcript maturation, or translation). The decrease or inhibition of Dynamin 2 expression can be evaluated by any means known to those skilled in the art including but not limited to assessing the level of Dynamin 2 protein using for instance Western Blot analysis (such as shown by FIG. 1) or ELISA, for example using an Anti Dynamin 2 antibody, and/or assessing the level of mRNA for Dynamin 2 (such as shown by FIG. 2) using any available technique such as quantitative PCR for example.

The Dynamin 2 inhibitor is preferably selected from the group consisting of an antibody directed against Dynamin 2, a nucleic acid molecule interfering specifically with Dynamin 2 expression, and a small molecule inhibiting the Dynamin 2 enzymatic activity (i.e., inhibition of the GTPase activity), expression (such as by inhibiting promoter, splicing or translation), or function (such as inhibition of oligomerisation, activation, lipid binding, or partner binding).

According to a particular embodiment, the Dynamin 2 inhibitor is selected from the group consisting of an antibody directed against Dynamin 2 or a nucleic acid molecule (or nucleotide) interfering specifically with Dynamin 2 expression. In a preferred embodiment, the Dynamin 2 inhibitor is selected from the group consisting of a nucleic acid molecule interfering specifically with Dynamin 2 expression. According to the invention, the nucleic acid molecule interfering specifically with Dynamin 2 expression is usually a non-naturally occurring nucleic acid. In a particular embodiment, the Dynamin 2 inhibitor is a RNAi, an antisense nucleic acid or a ribozyme interfering specifically with Dynamin 2 expression.

In a particular embodiment, the Dynamin 2 inhibitor is a siRNA or shRNA.

In the present invention, the nucleic acid is capable of hybridizing specifically to a gene or transcripts coding for Dynamin 2. By "hybridizing specifically", is intended hybridized in stringent conditions. In particular, stringent conditions can be defined by salt concentration, the concentration of organic solvent, for example, formamide, temperature, and other conditions well known in the art. Typical stringent hybridisation conditions include temperatures above 30° C., preferably above 35° C., more preferably in excess of 42° C., and/or salinity of less than about 500 mM, preferably less than 200 mM. Nevertheless, it is understood that the nucleic acid according to the invention does not need to have 100% complementarity with the target sequence to hybridize specifically. In particular, a nucleic acid with a degree of complementarity at least equal to approximately 90% is capable of hybridizing specifically. Preferably, the degree of complementarity between the nucleic acid according to the invention and the target sequence is equal to at least 95%, 96%, 97%, 98%, 99% or 100%.

The term "complementary" or "complementarity" refers to the ability of polynucleotides to form base pairs with another polynucleotide molecule. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated. Perfect complementarity or 100 percent complementarity refers to the situation in which each nucleotide unit of one polynucleotide strand can bind to a nucleotide unit of a second polynucleotide strand. Less than perfect complementarity refers to the situation in which some, but not all, nucleotide units of two strands can bind with each other. For example, for two 20-mers, if only two base pairs on each strand can bind with each other, the polynucleotide strands exhibit 10 percent complementarity. In the same way, if 18 base pairs on each strand can be bond with each other, the polynucleotide strands exhibit 90 percent complementarity.

As used herein, the term "iRNA", "RNAi" or "interfering RNA" means any RNA which is capable of down-regulating the expression of the targeted protein. It encompasses small interfering RNA (siRNA), double-stranded RNA (dsRNA), single-stranded RNA (ssRNA), and short hairpin RNA (shRNA) molecules. RNA interference designates a phenomenon by which dsRNA specifically suppresses expression of a target gene at post-transcriptional level. In normal conditions, RNA interference is initiated by double-stranded RNA molecules (dsRNA) of several thousands of base pair length. In vivo, dsRNA introduced into a cell is cleaved into a mixture of short dsRNA molecules called siRNA. The enzyme that catalyzes the cleavage, Dicer, is an endo-RNase that contains RNase III domains (Bernstein, Caudy et al. 2001 Nature. 2001 Jan. 18; 409(6818):363-6). In mammalian cells, the siRNAs produced by Dicer are 21-23 bp in length, with a 19 or 20 nucleotides duplex sequence, two-nucleotide 3' overhangs and 5'-triphosphate extremities (Zamore, Tuschl et al. Cell. 2000 Mar. 31; 101(1):25-33; Elbashir, Lendeckel et al. Genes Dev. 2001 Jan. 15; 15(2): 188-200; Elbashir, Martinez et al. EMBO J. 2001 Dec. 3; 20(23):6877-88). According to the invention, iRNAs do not encompass microRNAs.

A number of patents and patent applications have described, in general terms, the use of siRNA molecules to inhibit gene expression, for example, WO 99/32619. RNA interference therapy by siRNA and shRNA is also detailed in the review by Z. Wang et al., Pharm Res (2011) 28:2983-2995.

siRNA or shRNA are usually designed against a region 19-50 nucleotides downstream the translation initiator codon, whereas 5'UTR (untranslated region) and 3'UTR are usually avoided. The chosen siRNA or shRNA target sequence should be subjected to a BLAST search against EST database to ensure that the only desired gene is targeted. Various products are commercially available to aid in the preparation and use of siRNA or shRNA.

In a preferred embodiment, the RNAi molecule is a siRNA of at least about 10-40 nucleotides in length, preferably about 15-30 base nucleotides.

siRNA or shRNA can comprise naturally occurring RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end of the molecule or to one or more internal nucleotides of the siRNA, including modifications that make the siRNA resistant to nuclease digestion.

Some Dynamin 2 inhibitory nucleic acids are commercially available. One can cite for example, but not limited to: Abnova-Novus Biologicals, Dynamin 2 RNAi with references: H00001785-R05-H00001785-R08; Santa Cruz Biotechnology, Dynamin II siRNA (h) with reference: sc-35236, Dynamin II (h)-PR with reference: sc-35236-PR, Dynamin II shRNA Plasmid (h) with reference: sc-35236-SH, Dynamin II shRNA (h) Lentiviral Particles with reference: sc-35236-V).

In a particular embodiment, the nucleic acid molecule interfering specifically with Dynamin 2 is a nucleic acid interfering specifically with at least one part of the full length muscle human cDNA sequence of dynamin 2 (as shown in SEQ ID No 1, transcript variant 1 (NM_001005360.2)(exon 10a, 13ter) with 12b added). According to this embodiment, and more specifically, the RNAi molecule is a siRNA or shRNA of at least about 10-40 nucleotides in length, preferably about 15-30 base nucleotides iRNA. In a particular embodiment, siRNA or shRNA targets at least one exon of Dynamin2 mRNA, and more specifically at least one of exon 1, 4, 5, 12b, 13, 15, 17 and 21 of Dynamin2 mRNA.

In a particular embodiment, the nucleic acid molecule specifically interfering with Dynamin 2 comprises or consists of a sequence selected from the group consisting of

```
iRNA sequence of SEQ ID No 2:
5'- AAGGACATGATCCTGCAGTTCAT - 3'(or shRNA seq N°C, below), iRNA sequence of SEQ ID No 3:
5'- AAGAGGCTACATTGGCGTGGTGA- 3' iRNA sequence of SEQ ID No 4:
5'- AGGTGGACACTCTGGAGCTCTCC - 3', iRNA sequence of SEQ ID No 5:
5'- AAGAAGTACATGCTGCCTCTGGA - 3', iRNA sequence of SEQ ID No 6:
5'- AACGTCTACAAGGACCTGCGGCA - 3', iRNA sequence of SEQ ID No 7:
5'- AGGAGAACACCTTCTCCATGGAC - 3', iRNA sequence of SEQ ID No 8:
5'- AACTGTTACTATACTGAGCAG - 3', iRNA sequence of SEQ ID No 9:
5'- TGCCAACTGTTACTATACT - 3', iRNA sequence of SEQ ID No 10:
5' - GAAGAGCTGATCCCGCTGG -3' iRNA sequence of SEQ ID No 11:
5' - GCACGCAGCTGAACAAGAA -3' iRNA sequence of SEQ ID No 12:
5'-GGACTTACGACGGGAGATC-3' iRNA sequence of SEQ ID No 13:
5' -GGATATTGAGGGCAAGAAG-3' iRNA sequence of SEQ ID No 14:
5'-GGACCAGGCAGAAAACGAG-3' iRNA sequence of shRNA 15:
5'- GCGAATCGTCACCACTTAC-3'
```

| shRNA against DNM2 | Target sequence | Dnm2 Exon target | SEQ ID No: |
|---|---|---|---|
| A | AACCGCGGGATGGAAGAGCT | 1 | 16 |
| B | AACTTGACCCTCATCGACCTC | 4 | 17 |
| C | AAGGACATGATCCTGCAGTTCAT | 4 | 2 |
| D | TCGGTGTCATCACCAAGCT | 5 | 18 |
| E | TGCCAACTGTTTCTATACT | 12b | 19 |
| F | AACTGTTTCTATACTGAGGAG | 12b | 20 |
| G | TTTCTATACTGAGGAGCTGGT | 12b | 21 |
| H | GCACGCAGCTGAACAAGAA | 13 | 22 |
| I | AAGAAGTACATGCTGCCTCTGGA | 15 | 23 |
| J | AACACCTTCTCCATGGACCC | 17 | 24 |
| K | CCATTATCCGCCCAGCCGAGC | 21 | 25 |

Antisense nucleic acid can also be used to down-regulate the expression of Dynamin 2 The antisense nucleic acid can be complementary to all or part of a sense nucleic acid encoding Dynamin 2, e.g., complementary to the coding strand of a double-stranded cDNA molecule or complementary to an mRNA sequence, and it is thought to interfere with the translation of the target mRNA. The antisense nucleic acids used in the invention interfere specifically with Dynamin 2 expression.

According to an embodiment, the antisense nucleic acid is a RNA molecule complementary to a target mRNA encoding Dynamin 2.

According to another embodiment, the antisense nucleotide denotes a single stranded nucleic acid sequence, either DNA or RNA, which is complementary to a part of a pre-mRNA encoding Dynamin 2. In particular, the antisense nucleotide of the present invention is designed to block a splice acceptor (SA) site and/or an exon splicing enhancer (ESE) and/or a branch point in the Dynamin2 pre-mRNA and/or any sequence which could modulate pre-mRNA splicing, i.e. it is designed to be complementary to a part of the Dynamin 2 pre-mRNA comprising an SA, an ESE, a branch point sequence or any sequence which could modulate pre-mRNA splicing. More specifically, the antisense nucleotide is used for inducing exon-skipping within a Dynamin 2 pre-mRNA, thereby leading to a frameshift which produces a truncated cDNA containing a premature stop codon in the resulting mRNA. This strategy thus allows the reduction of the level of DNM2 protein. In a particular embodiment, the antisense nucleotide is used for inducing exon-skipping within a Dynamin 2 pre-mRNA. For example, the implemented antisense nucleotide is designed to specifically induce exon 2 or exon 8 skipping. In a particular embodiment, the antisense nucleotide of the present invention is able to induce the inclusion of a premature stop codon in the human DNM2 mRNA. Skipping of exon 2 or exon 8 was shown to lead to an absence of the Dynamin 2 protein (as mentioned in "Reducing dynamin 2 expression rescues X-linked centronuclear myopathy". Cowling B S, Chevremont T, Prokic I, Kretz C, Ferry A, Coirault C, Koutsopoulos O, Laugel V, Romero N B, Laporte J., J Clin Invest. 2014 Mar. 3; 124(3):1350-63. doi: 10.1172/JCI71206. Epub 2014 Feb. 24; and Tinelli E, Pereira J A, Suter U. Hum Mol Genet. 2013 Nov. 1; 22(21):4417-29. doi: 10.1093/hmg/ddt292. Epub 2013 Jun. 27).

In a particular embodiment, the antisense nucleotide is designed to specifically induce DNM2 exon 2 or exon 8 skipping, and comprises or consists of one of the following sequences: U7-Ex2 (target skipping of DNM2 exon 2 with an antisense U7 snRNA), comprising the following sequence:

SEQ ID No 26: GTCACCCGGAGGCCTCTCATTCTGCAGCTC

U7-Ex8 (target skipping of DNM2 exon 8 with an antisense U7 snRNA), comprising the following sequence:

SEQ ID No 27: ACACACTAGAGTTGTCTGGTGGAGCCCGCATCA

An antisense nucleic acid can be, for example, about 5, 10, 15, 20, 25, 30, 35, 40, 45 or 50 nucleotides in length. Particularly, antisense RNA molecules are usually 15-50 nucleotides in length. An antisense nucleic acid for use in the invention can be constructed using chemical synthesis and enzymatic ligation reactions using procedures known in the art. Particularly, antisense RNA can be chemically synthesized, produced by in vitro transcription from linear (e.g. PCR products) or circular templates (e.g., viral or non-viral vectors), or produced by in vivo transcription from viral or non-viral vectors. Antisense nucleic acid may be modified to have enhanced stability, nuclease resistance, target specificity and improved pharmacological properties. For example, antisense nucleic acid may include modified nucleotides or/and backbone designed to increase the physical stability of the duplex formed between the antisense and sense nucleic acids.

In the context of the invention "Ribozymes" are catalytic RNA molecules with ribonuclease activity which are capable of cleaving a single-stranded nucleic acid, such as an mRNA, to which they have a complementary region. Thus, ribozymes can be used to catalytically cleave mRNA transcripts to thereby inhibit translation of the protein encoded by the mRNA. Ribozyme molecules specific for functional Dynamin 2 can be designed, produced, and administered by methods commonly known to the art (see e.g., Fanning and Symonds (2006) *RNA Towards Medicine* (*Handbook of Experimental Pharmacology*), ed. Springer p. 289-303).

Genome editing can also be used as a tool according to the invention. Genome editing is a type of genetic engineering in which DNA is inserted, replaced, or removed from a genome using artificially engineered nucleases, or "molecular scissors". The nucleases create specific double-stranded break (DSBs) at desired locations in the genome, and harness the cell's endogenous mechanisms to repair the induced break by natural processes of homologous recombination (HR) and non-homologous end-joining (NHEJ). There are currently four families of engineered nucleases being used: Zinc finger nucleases (ZFNs), Transcription Activator-Like Effector Nucleases (TALENs), the CRISPR/Cas system (more specifically Cas9 system, as described by P. Mali et al., in Nature Methods, vol. 10 No. 10, October 2013), or engineered meganuclease re-engineered horning endonucleases. Said nucleases can be delivered to the cells either as DNAs or mRNAs, such DNAs or mRNAs are engineered to target the DNM2 gene, according to the invention. According to an embodiment, Dynamin 2 inhibitor is a DNA or mRNA engineered to target the DNM2 gene and to deliver nucleases using genome editing therapy or is a nuclease engineered to target the DNM2 using genome editing therapy.

The nucleotides as defined above used according to the invention can be administered in the form of DNA precursors or molecules coding for them.

For use in vivo, the nucleotides of the invention may be stabilized, via chemical modifications, such as phosphate backbone modifications (e.g., phosphorothioate bonds). The nucleotides of the invention may be administered in free (naked) form or by the use of delivery systems that enhance stability and/or targeting, e.g., liposomes, or incorporated into other vehicles, such as hydrogels, cyclodextrins, biodegradable nanocapsules, bioadhesive microspheres, or proteinaceous vectors, or in combination with a cationic peptide. They can also be coupled to a biomimetic cell penetrating peptide. They may also be administered in the form of their precursors or encoding DNAs. Chemically stabilized versions of the nucleotides also include "Morpholinos" (phosphorodiamidate morpholino oligomers—PMO), 2'-O-Methyl oligomers, AcHN-(RXRRBR)2XB peptide-tagged PMO (R, arginine, X, 6-aminohexanoic acid and B,®-alanine) (PPMO), tricyclo-DNAs, or small nuclear (sn) RNAs. The latter forms of nucleotides that may be used to this effect are small nuclear RNA molecules including U1, U2, U4, U4atac, U5, U7, U11, and U12 (or other UsnRNPs), preferably U7snRNA (as identified above for SEQ ID No 26 and 27, in particular in combination with a viral transfer method based on, but not limited to, lentivirus, retrovirus or adeno-associated virus. All these techniques are well known in the art.

The nucleic acid molecule interfering specifically with Dynamin 2 expression of the invention may be delivered in vivo alone or in association with a vector. In its broadest sense, a "vector" is any vehicle capable of facilitating the transfer of the nucleotide to the cells and preferably cells expressing DNM2. Preferably, the vector transports the nucleotide to cells with reduced degradation relative to the extent of degradation that would result in the absence of the vector. In general, the vectors useful in the invention include, but are not limited to, plasmids, phagemids, viruses, and other vehicles derived from viral or bacterial sources that have been manipulated by the insertion or incorporation of the nucleotides of the invention. Viral vectors are a preferred type of vector and include, but are not limited to nucleic acid sequences from the following viruses: lentivirus such as HIV-1, retrovirus, such as moloney murine leukemia virus, adenovirus, adeno-associated virus; SV40-type viruses; Herpes viruses such as HSV-1 and vaccinia virus. One can readily use other vectors not named herein but known in the art. Among the vectors that have been validated for clinical applications and that can be used to deliver the nucleotides, lentivirus, retrovirus and Adeno-Associated Virus (AAV) show a greater potential for exon skipping strategy.

As used herein, the term "antibody" is intended to refer broadly to any immunologic binding agent such as IgG, IgM, IgA, IgD and IgE, and humanized or chimeric antibody. In certain embodiments, IgG and/or IgM are preferred because they are the most common antibodies in the physiological situation and they are most easily manufactured. The term "antibody" is used to refer to any antibody-like molecule that has an antigen binding region, and includes antibody fragments such as Fab', Fab, F(ab')2, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Harlow, E. and Lane, D. (1988) *Antibodies: A Laboratory Manual*, ed., Cold Spring Harbor Laboratory).

A "humanized" antibody is an antibody in which the constant and variable framework region of one or more human immunoglobulins is fused with the binding region, e.g. the CDR, of an animal immunoglobulin. "Humanized" antibodies contemplated in the present invention are chimeric antibodies from mouse, rat, or other species, bearing human constant and/or variable region domains, bispecific antibodies, recombinant and engineered antibodies and fragments thereof. Such humanized antibodies are designed to maintain the binding specificity of the non-human antibody from which the binding regions are derived, but to avoid an immune reaction against the non-human antibody.

A "chimeric" antibody is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

Antibodies directed against Dynamin 2 are commercially available, such as antibodies sold or made by Novus Biologicals: catalogue numbers: Dynamin 2 Antibody NB300-617, Dynamin 2 Antibody NBP2-16244, Dynamin 2 Antibody (6C9) H00001785-M01, by Santa Cruz Biotechnology: catalogue number: sc-81150, sc-6400, sc-166525, sc-166669, sc-166526, by BD-Biosciences: anti-DNM2 (mouse ab, 610264), or by IGBMC-Illkirch: anti-DNM2: R2679, R2680, R2865, R2866, R2640, or R2641.

In another particular embodiment, the Dynamin 2 inhibitor is a small molecule inhibiting the Dynamin 2 enzymatic activity or function.

As used herein, the term "small molecule inhibiting Dynamin 2 activity, expression or function" refers to small molecule that can be an organic or inorganic compound, usually less than 1000 daltons, with the ability to inhibit or reduce the activity, expression or function of Dynamin 2. This small molecule can be derived from any known organism (including, but not limited to, animals, plants, bacteria, fungi and viruses) or from a library of synthetic molecules. Small molecules inhibiting Dynamin 2 activity, expression or function can be identified with the method described in this document.

Dynamin inhibitors are described in Harper C B et al., Trends Cell Biol. 2013 February; 23(2):90-101. Review. In a particular embodiment, such molecule is selected from the group consisting of:

Dynasore (a non-competitive, cell-permeable semicarbazone compound inhibitor of Dynamin 1 and Dynamin 2.—N° CAS 304448-55-3), its chemical name is 3-Hydroxynaphthalene-2-carboxylic acid (3,4-dihydroxybenzylidene)hydrazide, Hydroxy-Dynasore (a highly potent inhibitor of dynamin 2 ($IC_{50}$=2.6 µM)) (Hydroxy-Dynasore is a cell-permeable hydroxylated analog of Dynamin Inhibitor, Dynasore—N° CAS 1256493-34-1), its chemical name is 3-Hydroxy-N'-[(2,4,5-trihydroxyphenyl)methylidene]naphthalene-2-carbohydrazide, Tetradecyltrimethylammonium bromide (N° CAS 1119-97-7), sold under the name MiTMAB™ (ab120466) by Abcam (a Cell permeable dynamin 1 and dynamin 2 inhibitor (IC50=8.4 µM for inhibition of dynamin II). It targets the pleckstrin homology (PH) (lipid binding) domain. It inhibits receptor-mediated and synaptic vesicle endocytosis (IC50 values 2.2 µM), Phthaladyn-23 (a cell-permeable phthalimide compound that is reported to inhibit Dynamin 2 GTPase activity ($IC_{50}$=63 µM)), the chemical name of Phthaladyn-23 is 4-Chloro-2-((2-(3-nitrophenyl)-1,3-dioxo-2,3-dihydro-1H-isoindole-5-carbonyl)-amino)-benzoic acid, Dynole 34-2, it is a Dynamin inhibitor V (scbt.com) and acts on GTPase activity, non-competitive for GTP, chemical name of Dynole 34-2 is 2-Cyano-N-octyl-3-[1-(3-dimethylaminopropyl)-1H-indol-3-yl]acrylamide, M-divi 1 (mitochondrial division inhibitor, IC50=10 µM) (scbt.com), the chemical name of M-divi-1 is 3-(2,4-Dichloro-5-methoxyphenyl)-2-sulfanylquinazolin-4(3H)-one, Iminodyn-22/17 (scbt.com) (Iminodyn 22: $IC_{50}$=390 nM acting on a GTPase allosteric site and displays uncompetitive antagonism with respect to GTP), the chemical name of Iminodyn 22 is N,N'-(Propane-1,3-diyl)bis(7, 8-dihydroxy-2-imino-2H-chromene-3-carboxamide), the chemical name of Iminodyn 17 is N,N'-Ethane-1, 2-diyl)bis(7,8-dihydroxy-2-imino-2H-chromene-3-carboxamide).

OcTMAB, i.e., OctadecylTriMethylAmmonium Bromide, (abcam.com), it targets the PH domain, Dynamin inhibitory peptide (Tocris Biosciences 1774): with aminoacid sequence: QVPSRPNRAP Dyngo-4a (IC50 −2.5 µM), it acts on a GTPase allosteric site, chemical name of Dyngo-4a is 3-Hydroxy-N'-[(2, 4,5-trihydroxyphenyl)methylidene]naphthalene-2-carbohydrazide, RTIL-13 (IC50 −2.3 µM), it is a norcantharidin scaffold targeting the PH domain, chemical name of RTIL-13 is 4-(N,N-Dimethyl-N-octadecyl-N-ethyl)-4-aza-10-oxatricyclo-[5.2.1]decane-3,5-dione bromide.

Uses of Dynamin 2 Inhibitors

The invention relates to a method for treating a centronuclear myopathy by administering a therapeutically effective amount of a Dynamin 2 inhibitor as defined above to patients in need thereof, and to the uses of such Dynamin 2 inhibitor in the treatment of a centronuclear myopathy. It also relates to the use of a Dynamin 2 inhibitor for the manufacture of a pharmaceutical composition for the treatment of a centronuclear myopathy. It relates to a Dynamin 2 inhibitor for use in the treatment of a centronuclear myopathy.

Moreover, the present invention relates to a pharmaceutical composition comprising a Dynamin 2 inhibitor, and optionally a pharmaceutically acceptable carrier, in particular for use in the treatment of a centronuclear myopathy.

In a particular embodiment of the invention, the disease to be treated is selected from the group consisting of X-linked CNM (XLCNM), autosomal recessive CNM (ARCNM), and autosomal dominant CNM (ADCNM). In a more specific preferred embodiment, the centronuclear myopathy is XLCNM (also called myotubular myopathy) or ARCNM. In another specific embodiment, the centronuclear myopathy is a centronuclear myopathy due to BIN1 mutations, said pathology can be either recessive or dominant centronuclear myopathy.

As used herein, the term "therapeutically effective amount" is intended an amount of therapeutic agent, administered to a patient that is sufficient to constitute a treatment of a centronuclear myopathy. In a particular embodiment, the therapeutically effective amount to be administered is an amount sufficient to reduce the Dynamin 2 expression, activity or function in a level equal or preferably less than the normal level. The normal level is the Dynamin 2 expression, activity or function of subjects that do not present centronuclear myopathies (such as shown in FIG. 1, for instance). The amount of Dynamin 2 inhibitor to be administered can be determined by standard procedure well known by those of ordinary skill in the art. Physiological data of the patient (e.g. age, size, and weight), the routes of administration and the disease to be treated have to be taken into account to determine the appropriate dosage, optionally compared with subjects that do not present centronuclear myopathies. One skilled in the art will recognize that the amount of Dynamin 2 inhibitor or of a vector containing or expressing the nucleic acid interfering specifically with Dynamin 2 expression to be administered will be an amount that is sufficient to induce amelioration of unwanted centronuclear myopathy symptoms. Such an amount may vary inter alia depending on such factors as the selected dynamin 2 inhibitor, the gender, age, weight, overall physical condition of the patient, etc. and may be determined on a case by case basis. The amount may also vary according to other components of a treatment protocol (e.g. administration of other medicaments, etc.). Generally, when the Dynamin 2 inhibitor is a nucleic acid, a suitable dose is in the range of from about 1 mg/kg to about 100 mg/kg, and more usually from about 2 mg/kg/day to about 10 mg/kg. If a viral-based delivery of the nucleic acid is chosen, suitable doses will depend on different factors such as the virus that is employed, the route of delivery (intramuscular, intravenous, intra-arterial or other), but may typically range from $10^{-9}$ to $10^{-15}$ viral particles/kg. If the inhibitor is a small molecule inhibiting the Dynamin 2 activity, expression or function, each unit dosage may contain, for example, from 2 to 300 mg/kg of body weight, particularly from 5 to 100 mg/kg of body weight. If the inhibitor is an antibody, each unit dosage may contain, for example, from 0.1 to 20 mg/kg of body weight, particularly from 4 to 10 mg/kg of body weight. Those of skill in the art will recognize that such parameters are normally worked out during clinical trials. Further, those of skill in the art will recognize that, while disease symptoms may be completely alleviated by the treatments described herein, this need not be the case. Even a partial or intermittent relief of symptoms may be of great benefit to the recipient. In addition, treatment of the patient may be a single event, or the patient is administered with the Dynamin 2 inhibitor on multiple occasions, that may be, depending on the results obtained, several days apart, several weeks apart, or several months apart, or even several years apart.

The pharmaceutical composition of the invention is formulated in accordance with standard pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art.

Possible pharmaceutical compositions include those suitable for oral, rectal, intravaginal, mucosal, topical (including transdermal, buccal and sublingual), or parenteral (including subcutaneous, intramuscular, intravenous, intra-arterial and intradermal) administration. For these formulations, conventional excipient can be used according to techniques well known by those skilled in the art.

More particularly, in order to provide a localized therapeutic effect, specific muscular administration routes are preferred. In particular, intramuscular administration is preferred.

Pharmaceutical compositions according to the invention may be formulated to release the active drug substantially immediately upon administration or at any predetermined time or time period after administration.

Within the context of the invention, the term treatment denotes curative, symptomatic, and preventive treatment. As used herein, the term "treatment" of a disease refers to any act intended to extend life span of subjects (or patients) such as therapy and retardation of the disease progression. The treatment can be designed to eradicate the disease, to stop the progression of the disease, and/or to promote the regression of the disease. The term "treatment" of a disease also refers to any act intended to decrease the symptoms associated with the disease, such as hypotonia and muscle weakness. More specifically, the treatment according to the invention is intended to delay the appearance of the centronuclear myopathy phenotypes or symptoms, ameliorate the motor and/or muscular behavior and/or lifespan, in particular by rescuing myofibers intracellular organization, including myofibrils organization, triad structure and/or nuclei positioning.

The subject (or patient) to treat is any mammal, preferably a human being. Preferably the subject is a human patient, whatever its age or sex. New-borns, infants, children are included as well.

Screening of Dynamin 2 Inhibitors

The present invention also concerns a method for identifying or screening molecules useful in the treatment of a centronuclear myopathy, preferably XLCNM, based on the ability of such molecules to inhibit the expression, activity and/or function of Dynamin 2.

In particular, the invention is drawn to a method for screening comprising the steps of:

a) providing or obtaining a candidate compound; and b) determining whether said candidate compound inhibits the activity, function and/or expression of Dynamin 2, c) wherein the ability of said candidate compound to inhibit the expression, function or activity of said Dynamin 2 indicates that said candidate compound is indicative of its usefulness for the treatment of centronuclear myopathy.

The candidate compound to be tested in the frame of this method may be of any molecular nature, for example it may correspond to a chemical molecule (preferably a small molecule), an antibody, a peptide, a polypeptide, an aptamer, a siRNA, a shRNA, a snRNA, a sense or antisense oligonucleotide, or a ribozyme.

The ability of said candidate compound to inhibit the expression, activity or function of Dynamin 2 may be tested using any of the methods known to those skilled in the art, such as those identified above or described in the examples.

The method for screening or identifying a molecule suitable for the treatment of centronuclear myopathies can optionally further comprise the step of administering in vivo or in vitro selected molecule in a centronuclear myopathy non-human animal model or a part thereof (tissue or cells, such as muscle tissue or cells) and analyzing the effect on the myopathy onset or progression.

As centronuclear myopathy non-human animal models, one can cite Mtm1 exon 4 KO mice, Mtm1 R69C knock-in mice, Mtm1 Taconic gene trap (Mtm1$^{gt/y}$), Dnm2 knock-in R465W mice, Mtm1 mutated Labrador retriever, Bin1 mutated Great Danes) or mice as used in the following examples.

The following examples are given for purposes of illustration and not by way of limitation.

EXAMPLES

Example 1

Materials. Primary antibodies used were: mouse anti-DHPRα$_1$ (Ca$_v$1.1) subunit (MA3-920; Affinity Bioreagents), α-actinin (EA-53, Sigma-Aldrich), caveolin-3 (clone 26, BD Biosciences), desmin (Y-20; Santa Cruz Biotechnology) and glyceraldehyde-3-phosphate dehydrogenase (GAPDH, MAB374; Chemicon) monoclonal antibodies; and rabbit anti-RYR1 (a kind gift from Isabelle Marty, Grenoble Institut des Neurosciences, France). Rabbit anti-DNM2 antibodies (R2680 and R2865, characterized in Cowling, B. S. et al., 2011, Increased expression of wild-type or a centronuclear myopathy mutant of dynamin 2 in skeletal muscle of adult mice leads to structural defects and muscle weakness, *Am J Pathol* 178:2224-2235. Increased expression of wild-type or a centronuclear myopathy mutant of dynamin 2 in skeletal muscle of adult mice leads to structural defects and muscle weakness. *Am J Pathol* 178:2224-2235) and anti-MTM1 (R2827) (Hnia, K., et al. J. 2011. Myotubularin controls desmin intermediate filament architecture and mitochondrial dynamics in human and mouse skeletal muscle. *J Clin Invest* 121:70-85) were made at IGBMC (France). Alexa-conjugated secondary antibodies were purchased from Invitrogen. Secondary antibodies against mouse and rabbit IgG, conjugated with horseradish peroxidase (HRP) were purchased from Jackson ImmunoResearch Laboratories. The following products were purchased: Hoechst nuclear stain (B2883, Sigma-Aldrich), ECL chemiluminescent reaction kit (Pierce), Lipofectamine™ (Life Technologies), Tri reagent (Molecular Research Center, Ohio, USA), SYBR Green 1 Master kit (Roche Diagnostics), miScript reverse transcription kit (Qiagen), specific miScript primer assays (Qiagen) and an miScript Sybr green PCR kit (Qiagen). Patient control biopsies AHJ38 (1.5 months) and 39 (3.4 months), XLCNM biopsies with MTM1 mutations used were AHJ35 (15 days)(MTM1− intron 11-10A>GS420_R421insFIG) and AHJ36 (1m) (MTM1-c.445-49_445-4del), 1 (MTM1-p.Leu213Pro) and 15 (MTM1-p.Ileu466dup) and patient 12129/89 (MTM1− p.Val49PhefsX6, unpublished).

Generation of Dnm2 Heterozygous Mice.

Figure 10:
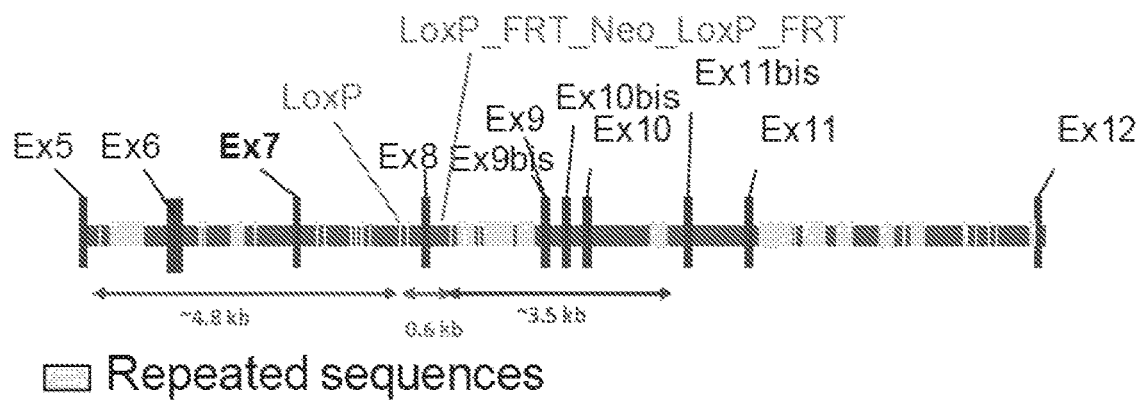
FIG. 10. Targeted disruption of mouse Dnm2 to create Dnm2 heterozygous mice. The genomic region surrounding the targeted exon 8 of Dnm2 in mice. Deletion of exon 8 is predicted to lead to an out-of-frame transcript.

The targeting vector was created with LoxP sites flanking exon 8 of Dnm2 (FIG. 10), then linearized and electroporated into embryonic stem (ES) cells. Recombinant ES cells were injected into C57BL/6 blastocysts that were implanted in pseudo-pregnant females and germline transmission determined. Mice bred and analyzed were 129pas strain (CMV promoter).

Generation of Mtm1−/y/Dnm2 Heterozygous Mice.

The creation and characterization of Mtm1−/y mice were described previously (Buj-Bello, A. et al. 2002. The lipid phosphatase myotubularin is essential for skeletal muscle maintenance but not for myogenesis in mice. *Proc Natl Acad Sci USA* 99:15060-15065; Al-Qusairi, L et al. 2009. T-tubule disorganization and defective excitation-contraction coupling in muscle fibers lacking myotubularin lipid phosphatase. *Proc Natl Acad Sci USA* 106:18763-18768). Female heterozygous Mtm1 mice 129pas strain were bred with male Dnm2 heterozygous mice to produce four possible genotypes in male offspring: Mtm1+/yDnm2+/+ (WT); Mtm1+/yDnm2+/− (Dnm2+/−); Mtm1−/yDnm2+/+ (referred as Mtm1−/y); and Mtm1−/yDnm2+/−. All mice analyzed were male.

Generation of Mtm1−/yDnm2$^{skm+/−}$ and Mtm1−/yDnm2$^{(i)skm+/−}$ Mice.

Human skeletal muscle α-actin (HSA-Cre) C57BL/6 and HSA Cre-ER$^{T2}$ mice were from IGBMC (France) (Schuler, M. et al. 2005. Temporally controlled targeted somatic mutagenesis in skeletal muscles of the mouse. *Genesis* 41:165-170; Miniou, P. et al. 1999. Gene targeting restricted to mouse striated muscle lineage. *Nucleic Acids Res* 27:e27. Floxed Dnm2+/− mice were bred with HSA-Cre mice and HSA Cre-ER$^{T2}$ to produce Cre-positive Dnm2skm+/− and Dnm2skm(i)+/− mice respectively. Male Dnm2$^{skm+/−}$ or Dnm2$^{(i)skm+/−}$ mice were bred with female Mtm1+/− mice. Male offspring with the following genotypes were analyzed; line 1: Mtm1+/yDnm2+/+ (WT), Mtm1−/yDnm2+/+ (Mtm1−/y), Mtm1−/yDnm2$^{skm+/−}$; and line 2: Mtm1+/yDnm2+/+ (WT), Mtm1−/yDnm2+/+ (Mtm1−/y), Mtm1−/yDnm2+/−HSA-Cre-ER$^{T2}$ tamoxifen inducible (Mtm1−/yDnm2$^{(i)skm+/−}$) mice. To induce excision of Dnm2 after birth, 3 week old mice were injected with 1 mg of tamoxifen (concentration 1 mg/100 µl), daily for 3 days. All mice were sacrificed at 16 weeks of age. All mice analyzed were male, 50% 129pas strain (Mtm1−/y) 50% C57BL/6 strain (HSA promoter) mice.

Animal Experiments.

Animals were housed in a temperature-controlled room (19-22° C.) with a 12:12-h light/dark cycle. Mice were weighed weekly until one year of age. Mice were humanely killed when required by CO$_2$ inhalation followed by cervical dislocation, according to national and European legislations on animal experimentation. Muscles and other tissues were dissected (TA muscle under anesthesia when required for TEM) and frozen in nitrogen-cooled isopentane and liquid nitrogen for histological and immunoblot assays, respectively.

Phenotyping of Dnm2+/− Mice.

Dnm2 heterozygous male and female mice aged 10-15 weeks were phenotyped under the EUMODIC phenotyping program (see Worldwide Website: eumodic.eu/) with results made publicly available (see Worldwide Website: europhenome.org/). Blood chemistry, ECG measurements, Dexascan, and Electromyography tests presented here for male mice (n=10 per group) were performed as part of pipelines 1 and 2 of the EUMODIC phenotyping program, at the Institut Clinique de la Souris (ICS, Illkirch, France, see Worldwide Website: www.ics-mci.fr/).

String, Grip (2 and 4 Paws), Hang, Rotarod and Footprint Tests.

String test: Mice are suspended on a wire by their forelimbs, and allowed 20 seconds to climb their hindlimbs onto the wire. Three trials per mouse were performed, with 5 minutes rest between trials. A fall was considered equal to 20 seconds (n=minimum 5 mice per group). Grip strength tests: Performed by placing the 2 front paws or all 4 paws on the grid of a dynamometer (Bioseb, Chaville, France) and mice were pulled by the tail in the opposite direction. The maximal strength exerted by the mouse before losing grip was recorded. Three trials per mouse were performed, with 30 seconds rest between trials (2 paw test, n=minimum 5 mice per group; 4 paw test, n=5-7 mice per group). Hanging test: mice were suspended from a cage lid for a maximum of 60 seconds. The time the mouse fell off the cage was recorded for each trial. Three trials per mouse were performed. Rotarod test: Coordination and whole body muscle strength and fatigability were tested using an accelerated rotating rod test (Panlab, Barcelona, Spain). Mice were placed on the rod which accelerated from 4 to 40 rpm during 5 minutes. Three trials per day, with 5 minutes rest between trials were performed for day 1 (training day) then 4 days which were recorded. Animals were scored for their latency to fall (in seconds). The mean of the three trials was calculated for each experiment listed above (n=5-7 mice per group). Footprint test: Hindfeet of mice were coated with nontoxic ink, and mice were allowed to walk through a tunnel (50 cm long, 9 cm wide, 6 cm high) with paper lining the floor. The angle between the hindlimbs was then measured from the footprint pattern generated, using ImageJ analysis program. A minimum of 6 footprints per mouse was analyzed (n=5-8 mice per group).

Plethysmograph Measurements.

The test was used to measure the spontaneous breathing pattern in non-restrained unstimulated mice and performed using a whole-body barometric plethysmograph (EMKA Technologies), at the ICS, Illkirch, France (n=3-5 mice per group).

TA Muscle Contractile Properties.

Muscle force measurements were evaluated by measuring in situ muscle isometric contraction in response to nerve and muscle stimulation, as described previously (Cowling, B. S. et al., 2011 *Am J Pathol* 178:2224-2235, Vignaud, A. et al. 2005 *Exp Physiol* 90:487-495; Vignaud, A. et al. *J Biomed Biotechnol* 2010:724914). Results from nerve stimulation are shown (n=5-11 mice per group). Fatigue was measured as time taken to reach 50% of the maximum force produced. After contractile measurements, the animals were killed by cervical dislocation. TA muscles were then dissected and weighed to determine specific maximal force.

Diaphragm Muscle Contractile Properties.

Diaphragm isometric contraction was assessed on muscle strips from the ventral part of the costal diaphragm, as previously described (50). In brief, two muscle strips per mouse were dissected in situ. Each muscle was mounted in a tissue chamber containing a Krebs-Henseleit solution. The solution was bubbled with a gas mixture of 95% $O_2$-5% $CO_2$ and maintained at 27° C. and pH 7.4. Muscle extremities were held in spring clips and attached to an electromagnetic force transducer. Diaphragm strips were electrically stimulated by means of two platinum electrodes positioned parallel to the muscle and delivering electrical stimulation of 1 ms duration. Force-frequency curve was determined. Absolute maximal force was achieved at a stimulation frequency of 100 Hz with train duration of 400 ms. At the end of the experiment, each muscle cross-sectional area (in $mm^2$) was calculated from the ratio of muscle weight to optimal muscle length (Lo), assuming a muscle density of 1.06. Total isometric peak force was normalized per cross-sectional area to obtain total tension in $mN \cdot mm^{-2}$ (n=3-5 mice per group).

Western Blotting.

Mouse muscles was minced and homogenized on ice for 3×30 s (Ultra Turrax homogenizer) in 10 times the weight/volume of 1% NP-40 Tris-Cl buffer, pH 8, then extracted for 30 min at 4° C. Protein concentration was determined using a DC protein assay kit (Bio-Rad Laboratories), and lysates analyzed by SDS-PAGE and western blotting on nitrocellulose membrane. Primary antibodies used were DNM2-R2680 (1:500), DNM2-R2865 (1:500), MTM1-R2827 (1:500), and GAPDH (1:10,000); secondary antibodies were anti-rabbit HRP or anti-mouse HRP (1:10,000).Western blot films were scanned and band intensities were determined using ImageJ software (Rasband, W. S., ImageJ, U.S. National Institutes of Health, Bethesda, Md., USA, http://rsb.info.nih.gov/ij/, 1997-2009). Densitometry values were standardized to corresponding total GAPDH values and expressed as a fold difference relative to the listed control (n=5-7 mice per group).

qRT-PCR Analysis.

Total RNA was extracted from 8 w old tibialis anterior skeletal muscle lysates using Tri reagent (Molecular Research Center, Ohio, USA), and reverse transcribed and amplified using Oligo dT primers. Real-time quantitative RT-PCR was then performed using a Lightcycler 480 (Roche Diagnostics, Meylan, France) with DNM2 primers (forward primer CCAACAAAGGCATCTCCCCT (SEQ ID. 28); reverse primer TGGTGAGTAGACCCGAAGGT (SEQ ID 29) and GAPDH mRNA as a standard, with the SYBR Green 1 Master kit (Roche Diagnostics). Results were standardized to corresponding total GAPDH values and expressed as a fold difference relative to WT littermate controls (n=2-3 mice per group, performed in triplicate).

Histological and Immunofluorescence Analysis of Skeletal Muscle.

Longitudinal and transverse cryosections (8 µm) sections of mouse skeletal muscles were prepared, fixed and stained with antibodies to $DHPR\alpha_1$ (1:100), RYR1 (1:200), α-actinin (1:1,000), caveolin-3 (1:1000); DNM2-R2680 (1:200), MTM1-R2827 (1:200), and desmin (1:100). Nuclei were detected by costaining with Hoechst (Sigma-Aldrich) for 10 min. Samples were viewed using a laser scanning confocal microscope (TCS SP5; Leica Microsystems, Mannheim, Germany). Air-dried transverse sections were fixed and stained with haematoxylin and eosin (HE) or succinate dehydrogenase (SDH), and image acquisition performed with a slide scanner NanoZoomer 2 HT equipped with the fluorescence module L11600-21 (Hamamatsu Photonics, Japan) or a DMRXA2 microscope (Leica Microsystems Gmbh). Cross-sectional area (CSA) was analyzed in HE sections from TA mouse skeletal muscle, using FIJI image analysis software. CSA ($\mu m^2$) was calculated (>500 fibers per mouse) from 4-7 mice per group. The percentage of TA muscle fibers with centralized or internalized nuclei was counted in >500 fibers from 4-6 mice using the cell counter plugin in ImageJ image analysis software.

Transmission Electron Microscopy.

Mice were anesthetized by intraperitoneal injection of 10 µl per body gram of ketamine (20 mg/ml, Virbac, Carros, France) and xylazine (0.4%, Rompun, Bayer, Wuppertal, Germany). TA muscle biopsies were fixed with 2.5% glutaraldehyde in 0.1 M cacodylate buffer (pH 7.2) and processed as described previously (Buj-Bello, A. et al., 2002, *Proc Natl Acad Sci USA* 99:15060-15065; Cowling, B. S. et al. 2011, *Am J Pathol*, 178:2224-2235). Triad structures were identified on longitudinal sections of muscle and the number of triads per sarcomere was quantified. The ratio of triads/sarcomere was calculated by dividing number of triads clearly identified, by the total number of sarcomeres present in the image, as described previously (Amoasii, L. et al. 2012 *PLoS Genet* 8:e1002965). 40-80 triads were counted per mouse.

Microscopy and Statistical Analysis.

All microscopy was performed at the IGBMC Imaging Centre. All samples for microscopy were mounted in Fluorsave reagent (Merck) and viewed at room temperature. Light microscopy was performed using a fluorescence microscope (DM4000; Leica microsystems) fitted with a colour CCD camera (Coolsnap cf colour, Photometrics) camera. Confocal microscopy was performed using a confocal laser scanning microscope (TCS SP2 or SP5; Leica Microsystems, Mannheim, Germany). ImageJ and FIJI analysis software were used for image analysis. Statistical analysis was performed using the unpaired student's t test unless stated otherwise. p-values of <0.05 were considered significant.

Study Approval.

Animal experimentation was approved by the institutional ethical committee Com'Eth IGBMC-ICS (2012-128). All human biopsies were used after informed consent was obtained.

Results

Figure 11:
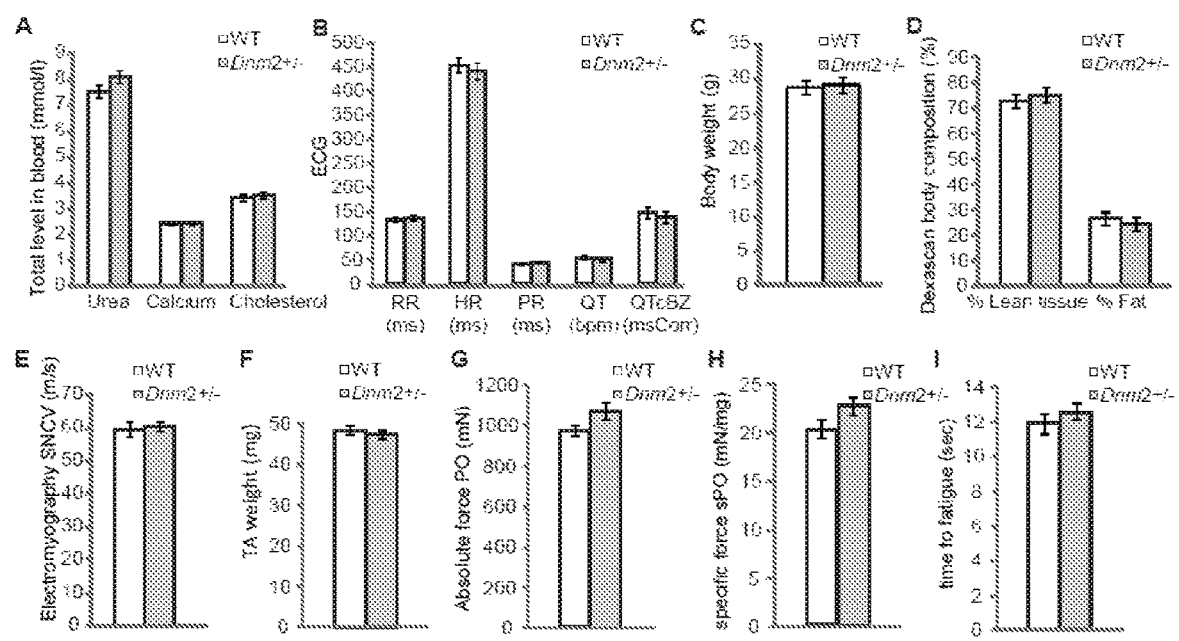
FIG. 11. Biochemical and phenotypic characterization of Dnm2 heterozygous mice. (A) Blood analysis of urea, calcium, and total cholesterol levels in Dnm2 heterozygous (Dnm2+/−) and wild type (WT) mice. (B) Electrocardiograph (ECG) measurements in WT and Dnm2+/− mice. X-axis values represent measurements shown below each test as follows; RR (interval between two R waves, measured in ms); HR=heart rate (ms); PR (interval from P-R wave, ms); QT (interval from Q-T waves, bpm); QTcBZ (QT corrected, msCorr). (C) Whole body weight. (D) Dex-ascan for whole body composition. The amount of lean tissue and fat are shown as a percentage of total body composition. (E) Single nerve conduction velocity (SNCV) results from muscle electromyography performed on WT and Dnm2+/− mice. (F) Total mass of the TA muscle. Absolute (G) and specific (H) maximal force of the TA muscle. (I) Measurement of fatigue of the TA muscle, fatigue represents time to 50% maximal force production in seconds (s). All mice analyzed were 10-15 week old male mice (n=8-12 per group). All graphs depict mean±s.e.m and none of the evaluated parameters were significantly different between WT and Dnm2+/− mice.

Creation and characterization of Dnm2 heterozygous (Dnm2+/−) mice. Constitutive knockout of Dnm2 was previously shown to be lethal early during embryogenesis (Ferguson. S. M. et al. 2009. Coordinated actions of actin and BAR proteins upstream of dynamin at endocytic clathrin-coated pits. Dev Cell 17:811-822). Dnm2 knockout (Dnm2−/−) mice were created by targeting exon 8 of Dnm2 (FIG. 10) (see methods section for details). From 100 pups we did not identify any Dnm2−/− mice, confirming that Dnm2−/− is embryonically lethal. Heterozygous (Dnm2+/—) pups were identified as expected from mendelian inheritance ratios, and these pups were further analyzed under the EUMODIC phenotyping program (for further details see methods section and Worldwide Website: eumodic.eu/). Basic blood chemistry test indicated no difference between wild type (WT) and heterozygous (Dnm2+/−) mice for urea (indicating normal kidney function), calcium (osmotic homeostasis) and total cholesterol (indicating absence of cardiovascular disease) levels (FIG. 11A). Normal ECG measurements suggested unaltered electrical activity in the heart (FIG. 11B). Overall there was no apparent difference in body weight (FIG. 11C), nor a difference in lean tissue or fat content between WT and Dnm2+/− mice (FIG. 11D). Basic muscle function tests were then performed. An electromyography test revealed no difference in Single Nerve Conduction Velocity (SNCV) (FIG. 11E). Tibialis anterior (TA) muscle mass was similar between WT and Dnm2+/− mice (FIG. 11F), and no difference in absolute or specific maximal force or fatigability of the TA muscle was detected (FIG. 11G-I), indicating overall that Dnm2+/− mice are clinically and physiologically similar to WT mice, with no detectable difference in muscle function.

DNM2 Levels in X-Linked Centronuclear Myopathy.

Before investigating the therapeutic potential of downregulation of DNM2 in XLCNM, DNM2 protein levels were checked by western blot analysis on muscle lysates from XLCNM patients (FIG. 1A). A 1.5 fold increase was identified in DNM2 protein expression from five neonatal XLCNM muscle biopsies tested, when compared to control age-matched biopsies (FIG. 1B). It was then determined if the increase in DNM2 expression was also observed in an animal model of XLCNM. In this study the Mtm1−/y mice that were previously characterized and reproduced faithfully XLCNM were used (Buj-Bello, A. et al. 2002 *Proc Natl Acad Sci USA* 99:15060-15065; Al-Qusairi, L. et al. 2009, *Proc Natl Acad Sci USA* 106:18763-18768; Amoasii, L. et al., 2012, *PLoS Genet* 8:e1002965). TA muscle lysates from 5 week old Mtm1−/y mice exhibited a significant increase in DNM2 levels compared to WT control littermates (FIGS. 1C, D), suggesting that increased DNM2 is linked to the XLCNM phenotype. An increase in DNM2 expression was also observed in the diaphragm muscle (FIGS. 1E, F), and this muscle appeared affected histologically, with more atrophic fibers containing mislocalized nuclei (FIG. 1G). This finding suggests respiratory insufficiency as a cause of death for the Mtm1−/y mice.

Reducing DNM2 Expression Greatly Prolongs the Lifespan of Mtm1−/y Mice.

Reducing DNM2 at the genetic level to 50% in the Dnm2+/− mice has no detectable clinical or physiological impacts. To test if reducing dynamin 2 expression may rescue X-linked CNM due to MTM1 mutations, Mtm1+/− mice were crossed with Dnm2+/− mice to produce male offspring that are Mtm1−/yDnm2+/−. Most Mtm1−/y mice died between 1-3 months of age as previously reported (Buj-Bello, A. et al. 2002 *Proc Natl Acad Sci USA* 99:15060-15065), whereas 100% of Mtm1−/yDnm2+/− mice survived for at least one year (FIG. 2A), with no significant difference in body weight compared to WT mice (FIG. 2B), indicating that reduced expression of DNM2 can rescue the early lethality observed in Mtm1−/y mice. Mtm1−/yDnm2+/− mice that were not sacrificed are now more than 2 year old. At 8 w when around 60% of Mtm1−/y mice were still alive, Mtm1−/yDnm2+/− mice were not distinguishable from WT mice upon general inspection, whereas Mtm1−/y mice displayed a significant decrease in movement and activity.

Figure 14:
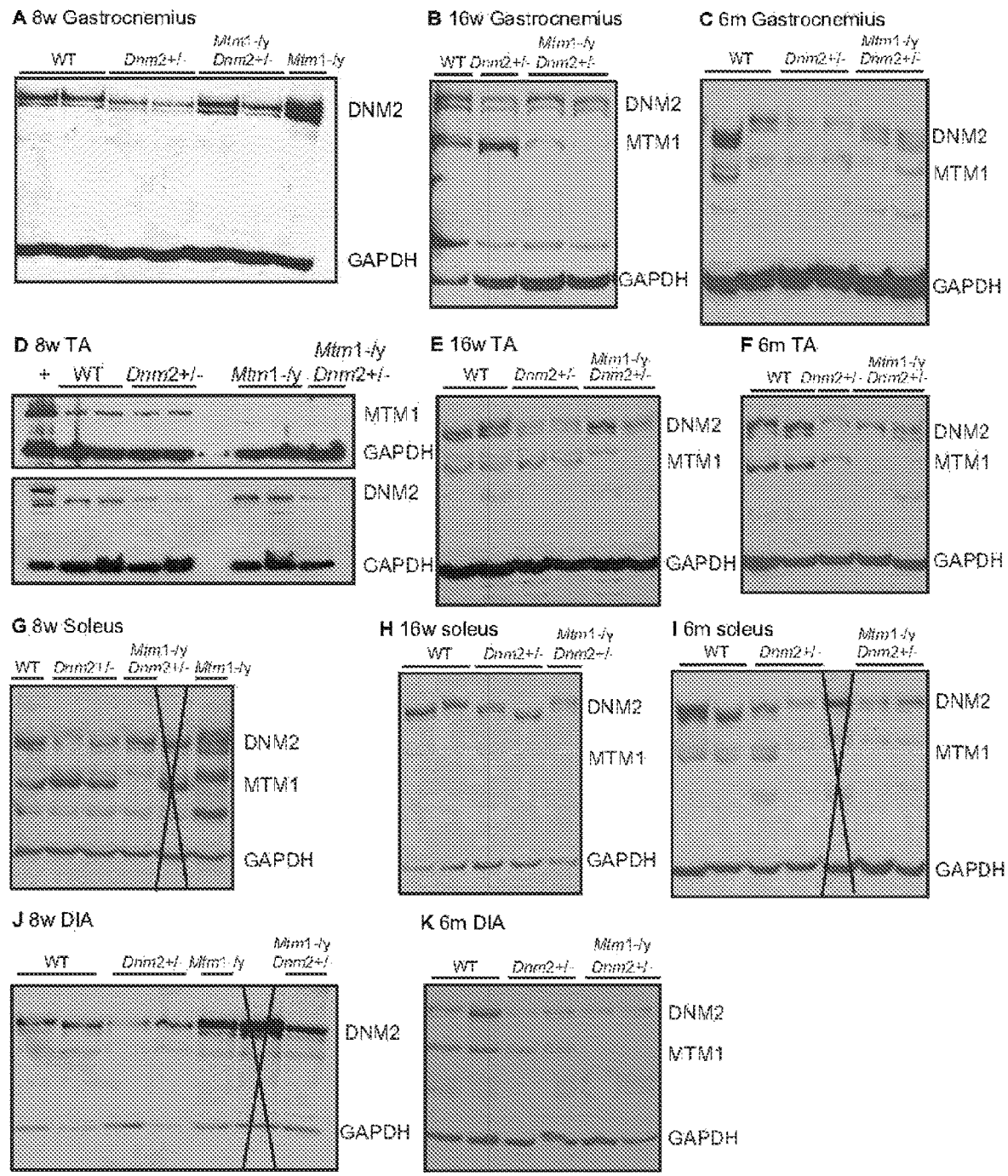
FIG. 14. Protein expression levels in various muscles at different ages. Lysates from 8 (A,D,G,J), 16 (B,E,H) weeks and 6 months (C,F,I,K) old gastrocnemius (GAS) (A-C), tibialis anterior (TA) (D-F), soleus (G-I), and diaphragm (J,K) muscles were immunoblotted for DNM2 and GAPDH (loading control). Where listed, lysates were also blotted for MTM1. When a doublet is present, MTM1 is represented by the lower band. Intervening lanes not relevant to this study were marked with a cross (G, I, J).

Western blot analysis was performed on lysates from several muscles at different ages, to determine the level of DNM2 protein expression. In the diaphragm muscle DNM2 protein levels were reduced approximately 50% in Dnm2+/− and Mtm1−/yDnm2+/− mice compared to WT mice, as expected, at both 8 weeks (8 w) and 6 months (6 m) of age (FIG. 2C). Mtm1−/y mice exhibited an increase in DNM2 in diaphragm compared to WT mice at 8 w, consistent with results from 5 week old mice (FIG. 1F). In the gastrocnemius (FIG. 2D), tibialis anterior (FIG. 2E), and soleus (FIG. 2F) muscles, the same trend was seen at 8 w, 16 w and 6 m (FIG. 14). Therefore DNM2 levels are consistently increased in Mtm1−/y mice and consistently reduced in Dnm2+/− and Mtm1−/yDnm2+/− mice compared to WT mice in different muscles at different ages.

To determine if the varied DNM2 protein expression is due to altered protein synthesis qRT-PCR analysis was performed on 8 w TA muscles lysates. The mRNA Dnm2 levels in both Dnm2+/− and Mtm1−/yDnm2+/− mice were significantly reduced compared to WT and Mtm1−/y mice (FIG. 2G), correlating with DNM2 protein expression (FIG. 2E). Interestingly no significant increase was seen in Dnm2 mRNA expression in Mtm1−/y muscle lysates compared to WT mice, indicating that the increase in DNM2 protein expression in Mtm1−/y muscle may be due to increased stabilization of DNM2 or reduced degradation, rather than increased transcription.

Figure 12:
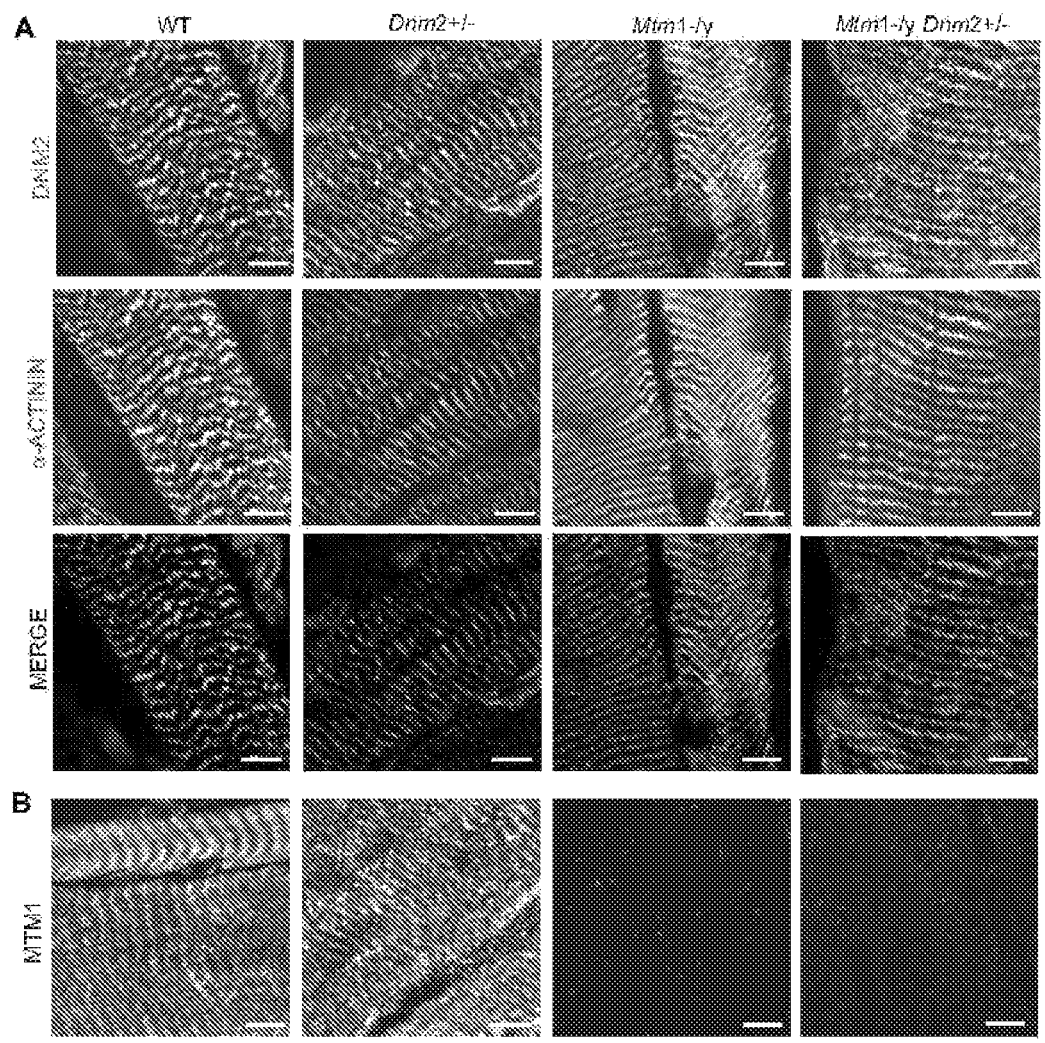
FIG. 12. Dynamin 2, myotubularin and α-actinin localization in TA muscles. Longitudinal muscle sections from 8 week old mice were co-stained with DNM2-R2680 (green) and -actinin (red) (A) antibodies or stained with MTM1-R2827 (B) antibody and imaged by confocal microscopy. Scale bar 5 μm.

As the TA muscle was one of the most affected muscles in Mtm1−/y mice, the localization of MTM1 and DNM2 was investigated by immunofluorescence analysis on TA muscle from 8 w mice. The Z-line, identified by α-actinin staining, appeared relatively undisturbed (FIG. 12A). DNM2 colocalized with α-actinin at the Z-line, and appeared relatively unperturbed in Mtm1−/y and Mtm1−/yDnm2+/− mice (FIG. 12A). Myotubularin was barely detectable in Mtm1−/y and Mtm1−/yDnm2+/− mice as expected (FIG. 12B). Altogether, reducing expression of DNM2 rescues the lifespan and body weight of Mtm1−/y mice to wild-type level.

Muscle Atrophy in Mtm1−/y Mice is Rescued by Reducing DNM2 Expression.

To analyze further the effect of reducing DNM2 expression in Mtm1−/y mice, the mass of different muscles was measured. The fast twitch gastrocnemius muscle was atrophied in Mtm1−/y mice, however no atrophy was observed in Mtm1−/yDnm2+/− analyzed up to 1 year of age (FIG. 2H). Likewise other fast twitch muscles, the EDL and plantaris muscle did not exhibit atrophy in Mtm1−/yDnm2+/− mice up to 1 year of age compared to WT mice (FIGS. 13A,B). The TA muscle, which has been the most characterized in Mtm1−/y mice, showed a strong atrophy in Mtm1−/y mice compared to Mtm1−/yDnm2+/−, WT, and Dnm2+/− mice at 8 w (FIG. 2I). Mtm1−/yDnm2+/− TA weights were indistinguishable from WT mice at this age. At 16 w unlike Mtm1−/y mice, Mtm1−/yDnm2+/− mice are still alive (FIG. 2A), and present with some TA atrophy compared to WT and Dnm2+/− mice, indicating TA atrophy in Mtm1−/yDnm2+/− is delayed. Interestingly the slow-twitch soleus muscle exhibited atrophy in Mtm1−/y mice at 8 w whereas there was no atrophy was present in Mtm1−/yDnm2+/− mice up to 1 year of age compared to WT mice (FIG. 2J). Similar results were seen when whole muscle mass was measured relative to body weight (FIG. 13C-E). No difference was observed in liver or heart weights between Mtm1−/yDnm2+/− and WT mice (FIGS. 13F,G). Therefore muscle atrophy was fully rescued in gastrocnemius and soleus muscles, and strongly delayed in TA muscle following the reduction of DNM2 expression in Mtm1−/y mice.

CNM Histological Features are Greatly Rescued in Mtm1−/y Mice by Reducing DNM2 Expression.

CNM presents histologically with mislocalized internal nuclei and muscle fiber hypotrophy. two main timepoints were analyzed: early (8 weeks old (8 w)), when the majority of the Mtm1−/y mice are still alive, and late (16 weeks old (16 w)), when 95% of Mtm1−/y mice have died. At 8 w Mtm1−/y TA muscle exhibited characteristic mislocalization of nuclei (FIGS. 3A,F), reduced fiber size (FIGS. 3A,D) and abnormal SDH staining with subsarcolemmal and central accumulations (FIG. 3A). Mtm1−/yDnm2+/− TA muscles were histologically similar to WT and Dnm2+/− mice, as observed for the gastrocnemius and soleus muscles (FIGS. 13H, I), with only a few abnormal fibers on SDH staining (FIG. 3A). Fiber hypotrophy was rescued, and internal and central nuclei significantly reduced compared to Mtm1−/y mice (FIGS. 3A,D,F). In addition membrane accumulations around the nucleus were reduced (FIG. 3B). By 16 w the TA muscle phenotype from Mtm1−/yDnm2+/− mice was mixed, as some areas appeared healthy, and other areas resembled Mtm1−/y mice at 8 w, with muscle fiber hypotrophy, mislocalization of nuclei, and abnormal SDH staining (FIGS. 3C, E, F). The localization of desmin, an MTM1 binding partner shown to be disrupted in Mtm1−/y mice (Hnia, K. et al. 2011, *J Clin Invest* 121:70-85), was next analyzed. Mtm1−/y mice showed a strong perturbation in desmin localization, which was barely observed in Mtm1−/y Dnm2+/− mice (FIG. 15A), indicating normal desmin localization is restored in 8 w Mtm1−/yDnm2+/− mice. Overall these results indicate presentation of the CNM phenotype in different muscles in Mtm1−/y mice is rescued or strongly delayed by reduction of dynamin 2 protein expression.

Reducing DNM2 Expression Improves Muscle Strength and Performance of Mtm1−/y Mice.

Figure 4:
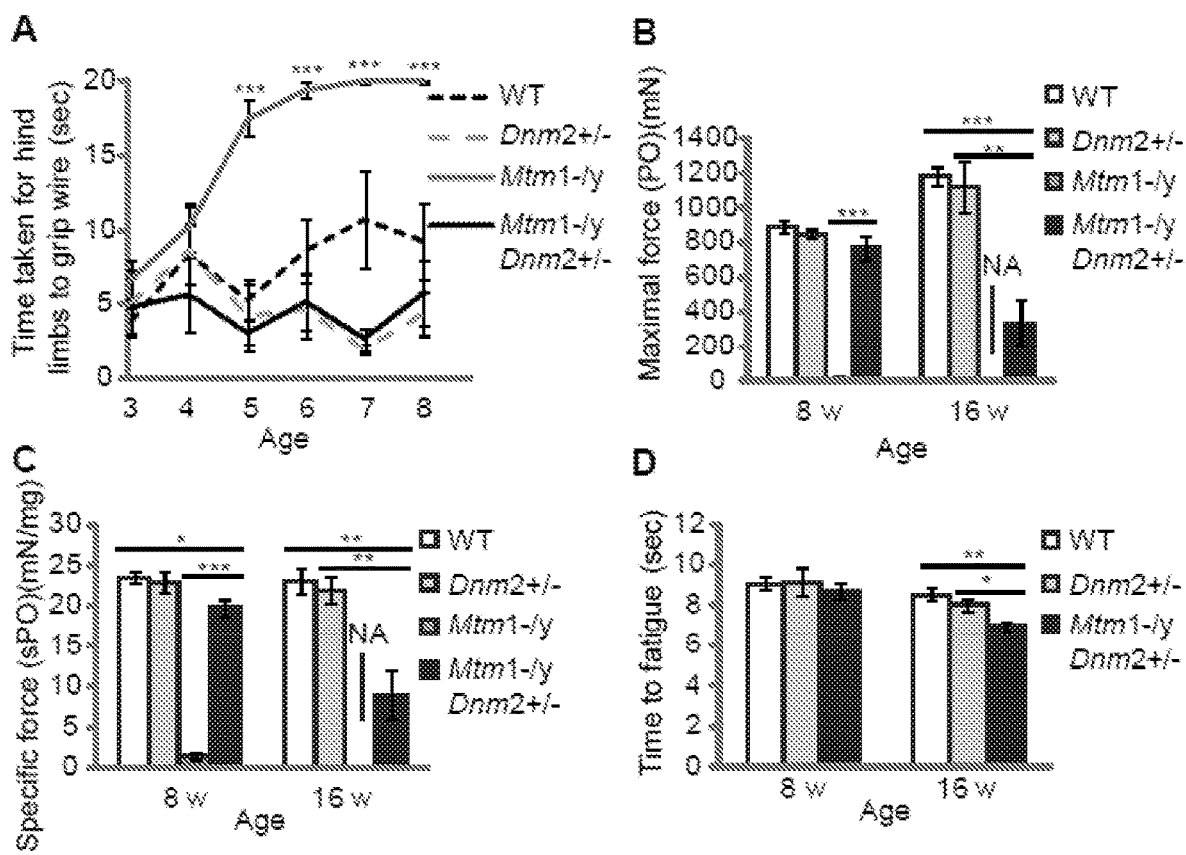
FIG. 4. Improved muscle strength and endurance of Mtm1−/y mice with reduced DNM2 expression. (A) The string test was performed on mice weekly from 3 to 8 weeks old. A fall was considered equal to 20 seconds. (B) The absolute maximal force of the TA muscle was measured in 8 and 16 weeks old mice. (C) The specific maximal force of the TA muscle represents the absolute maximal force related to muscle weight. (D) TA muscle fatigability was measured as the time taken to reach 50% of maximum muscle force produced in (B). Muscle fatigue was unable to be measured in Mtm1−/y mice at 8 weeks old due to extreme muscle weakness. Mtm1−/y mice usually die before 16 weeks old and were therefore not measured at that age (NA). All graphs depict mean±s.e.m. ($*p<0.05$, $p<0.01$, $*p<0.001$) (n=minimum 5 mice per group).

To determine if reducing DNM2 expression rescues the functional phenotype of Mtm1−/y mice in addition to the histological phenotype, various tests were performed. The string test requires mice that are suspended by their front paws to lift and hold their hind limbs on the bar. Whilst Mtm1−/y mice fell off the string on several trials and were unable to perform the test by 8 w, Mtm1−/yDnm2+/− mice performed the test similarly to WT and Dnm2+/− mice (FIG. 4A), indicating a rescue of whole body strength at this age. Absolute and specific (relative to muscle mass) maximal force were measured at 8 and 16 w in the TA muscles. At 8 w, Mtm1−/y mice exhibited extremely weak absolute and specific maximal muscle force, whereas Mtm1−/yDnm2+/− mice performed the test similarly to WT and Dnm2+/− mice (FIGS. 4B, C). At 16 w the maximal force of the TA muscle of Mtm1−/yDnm2+/− mice was reduced, consistent with histological data. Furthermore no change in fatigability was observed at 8 w, however at 16 w TA muscles fatigued faster than controls (FIG. 4D). Notably histologically and physiologically 16 w Mtm1−/yDnm2+/− mice performed better than Mtm1−/y mice at 8 w, indicating either a slower progression of the disease, or rescue in some but not all muscle fibers as indicated by the mixed phenotype observed histologically in the TA muscle at 16 w. Overall atrophy and decreased maximal muscle force of the TA muscle in Mtm1−/yDnm2+/− mice is reduced and strongly delayed compared to Mtm1−/y mice.

Improved Muscle Ultrastructure in Mtm1−/yDnm2+/− Mice.

Figure 5:
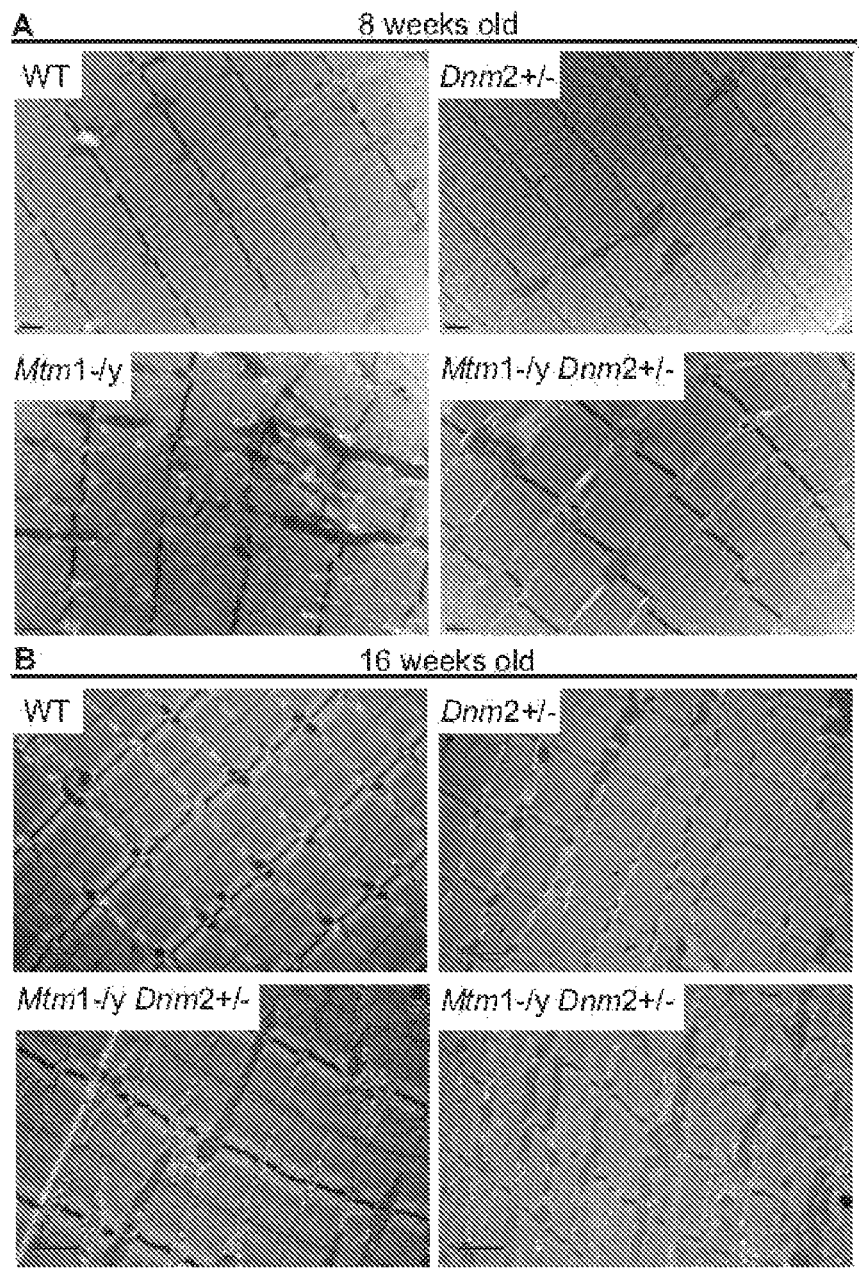
FIG. 5. Improved muscle ultrastructure of Mtm1−/y mice with reduced DNM2 expression. TA muscles from 8 (A) and 16 weeks old (B) mice were imaged by Transmission Electron Microscopy. Scale bar 0.5 mm (A) or 1 mm (B).

It was next determined whether the ultrastructure of Mtm1−/yDnm2+/− muscle was rescued. Transmission electron microscopy (TEM) was performed on TA muscles from 8 and 16 w Mtm1−/yDnm2+/− mice. 8 w Mtm1−/yDnm2+/− TA morphology resembled that of WT and Dnm2+/− mice, with aligned Z-lines and sarcomeres and no obvious mitochondrial structural abnormalities, whereas Mtm1−/y muscle displayed abnormal mitochondria shape, abnormal membrane accumulations and Z-line mis-alignment, and altered myofibrillar width (FIG. 5A). Noteworthy muscle from Mtm1−/yDnm2+/− mice at 16 w was heterogeneous, some regions appeared healthy (FIG. 5B, bottom left), whilst other areas appeared disturbed (bottom right). Furthermore mitochondrial abnormalities were detectable in some regions of 16 w old Mtm1−/yDnm2+/− mice, which were not evident at 8 w. This supports our previous histological and physiological results, indicating the CNM phenotype in Mtm1−/yDnm2+/− TA muscle is partially albeit substantially rescued at different timepoints.

Triad Structures are Normalized in Mtm1−/yDnm2+/− Mice.

Figure 6:
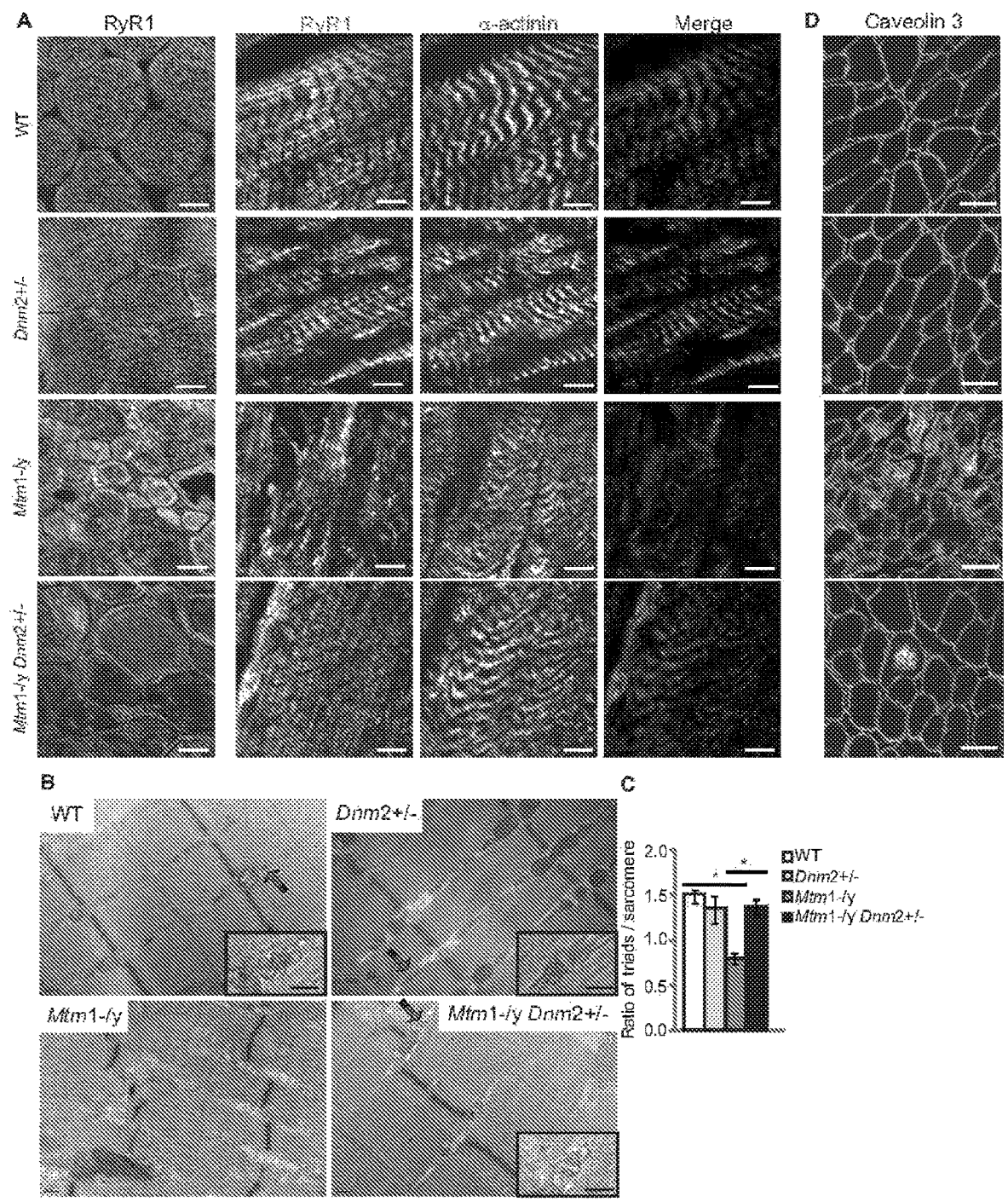
FIG. 6. Localization of triads in TA muscle from 8 week old mice. (A) Transverse and longitudinal muscle sections were stained with RyR1, or costained with RyR1 (green) and α-actinin (red) antibodies and imaged by confocal microscopy. Scale bar 20 mm (transverse) or 5 mm (longitudinal images). (B) TA muscles from 8 week old mice were imaged by Transmission Electron Microscopy (TEM). Arrows point to normally localized triads, shown in high magnification insert. Scale bar 200 nm, high magnification scale bar 100 nm. (C) Percentage of triads visualized per sarcomere in 8 week old TA muscles from (B). Graph depicts mean±s.e.m ($*p<0.05$). (D) Transverse muscle sections were stained with Caveolin 3 and imaged by confocal microscopy. Scale bar 50 mm.
Figure 15:
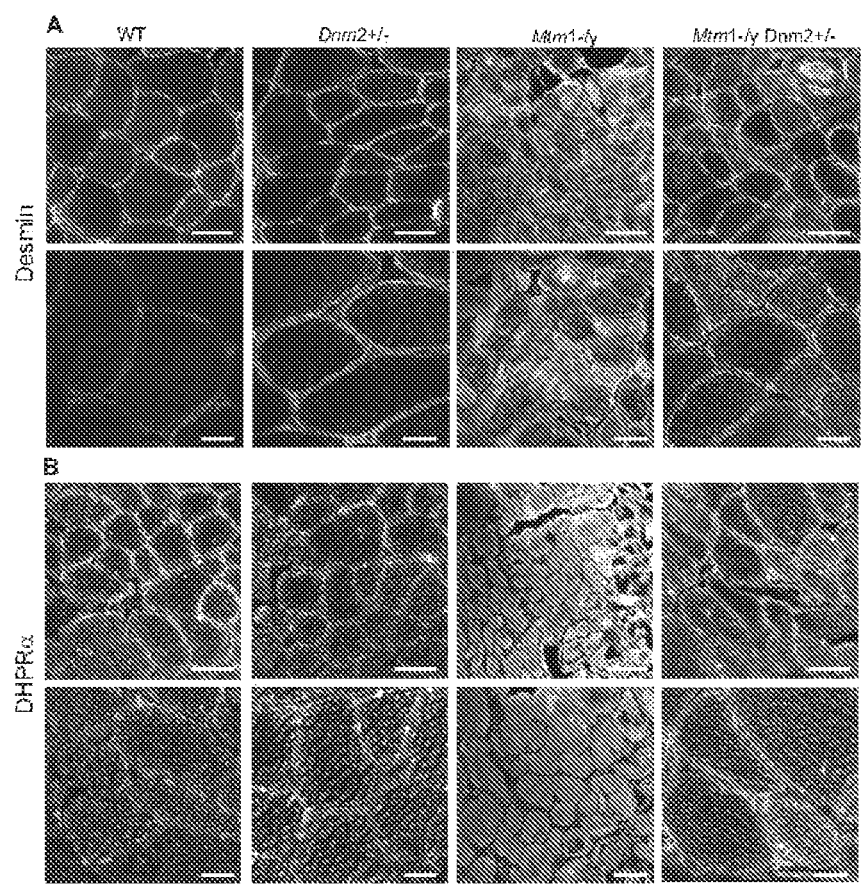
FIG. 15. Localization of desmin and organization of triad structures are rescued in TA muscles from 8 week old Mtm1−/y mice with reduced dynamin 2 expression. Transverse muscle sections from 8 week old mice were stained with a desmin (A) or DHPRα (B) antibody and imaged by confocal microscopy. Scale bar 50 μm (upper panel) and 20 μm (lower panel) for both. Note the cytosolic accumulation of desmin in Mtm1−/y, which is rescued in most Mtm1−/ yDnm2+/− fibers.

A common feature shared between CNM patients and animal models of CNM is a disruption of the structure and position of triads within skeletal muscle (Toussaint, A. et al. 2011. Defects in amphiphysin 2 (BIN1) and triads in several forms of centronuclear myopathies. *Acta Neuropathol* 121: 253-266; Dowling, J. J., et al. 2009. Loss of myotubularin function results in T-tubule disorganization in zebrafish and human myotubular myopathy. *PLoS Genet* 5:e1000372; Al-Qusairi, L. et al. 2009. T-tubule disorganization and defective excitation-contraction coupling in muscle fibers lacking myotubularin lipid phosphatase. *Proc Natl Acad Sci USA* 106:18763-18768; Beggs, et al. 2010. MTM1 mutation associated with X-linked myotubular myopathy in Labrador Retrievers. *Proc Natl Acad Sci USA* 107:14697-14702). To determine if triad structures were affected in Mtm1−/yDnm2+/− mice, the localization of triad markers were examined by immunolabeling. DHPRα, a voltage-dependent calcium channel found on T-tubules of mature muscles, was localized in punctuate structures within TA myofibers of WT and Dnm2+/− mice, consistent with T-tubule localization (FIG. 15B). However in Mtm1−/y muscle this specific staining was lost, indicating severe disruption of the T-tubules. In Mtm1−/yDnm2+/− muscle DHPRα localized similarly to WT and Dnm2+/− muscle, suggesting rescue of the T-tubule structures in these mice. This was confirmed by staining muscle sections for the ryanodine receptor (RyR1), a calcium channel localized specifically at the sarcoplasmic reticulum of triads. Transverse images showed a rescue of RyR1 localization in most fibers from Mtm1−/yDnm2+/− mice, with only a few fibers exhibiting RyR1 accumulations as seen extensively in Mtm1−/y mice (FIG. 6A). On longitudinal images a doublet of RyR1 staining was observed around the Z-line (marked with α-actinin) in WT and Dnm2+/− muscle consistent with triad localization. This staining in Mtm1−/y muscle was severely perturbed, and partially rescued in Mtm1−/yDnm2+/− muscle. To further analyze the triads, high magnification TEM images were taken from 8 w mice. A strong disruption of T-tubule/triad structures was observed in Mtm1−/y mice compared to WT and Dnm2+/− mice, whereas well positioned triads were clearly visible in Mtm1−/yDnm2+/− mice (FIG. 6B). Analysis of the triads confirmed no difference in the number of triads per sarcomere in WT, Dnm2+/−, or Mtm1−/yDnm2+/− mice, whereas Mtm1−/y mice exhibited a reduced number of triads per sarcomere (FIG. 6C). Therefore the localization and structure of triads were rescued in 8 w Mtm1−/yDnm2+/− mice.

Caveolin 3 is found at T-tubules during muscle development and regeneration, whereas in mature muscle caveolin 3 is mainly localized to the sarcolemma (reviewed in Miniou, P., et al. 1999. Gene targeting restricted to mouse striated muscle lineage. *Nucleic Acids Res* 27:e27). To determine if caveolin 3 localization is disrupted in Mtm1−/y and Mtm1−/yDnm2+/− mice, transverse muscle sections were stained with an antibody to caveolin 3. Whilst WT and Dnm2+/− muscle showed caveolin 3 localizing to the sarcolemma as expected, many fibers from Mtm1−/y mice exhibited a strong internal staining pattern of caveolin 3 (FIG. 6D). This phenotype was largely rescued in Mtm1−/yDnm2+/− muscle, with only occasional fibers showing internal localization of caveolin 3.

Longterm Physiological Phenotype of Mtm1−/y Dnm2+/− Mice.

Figure 7:
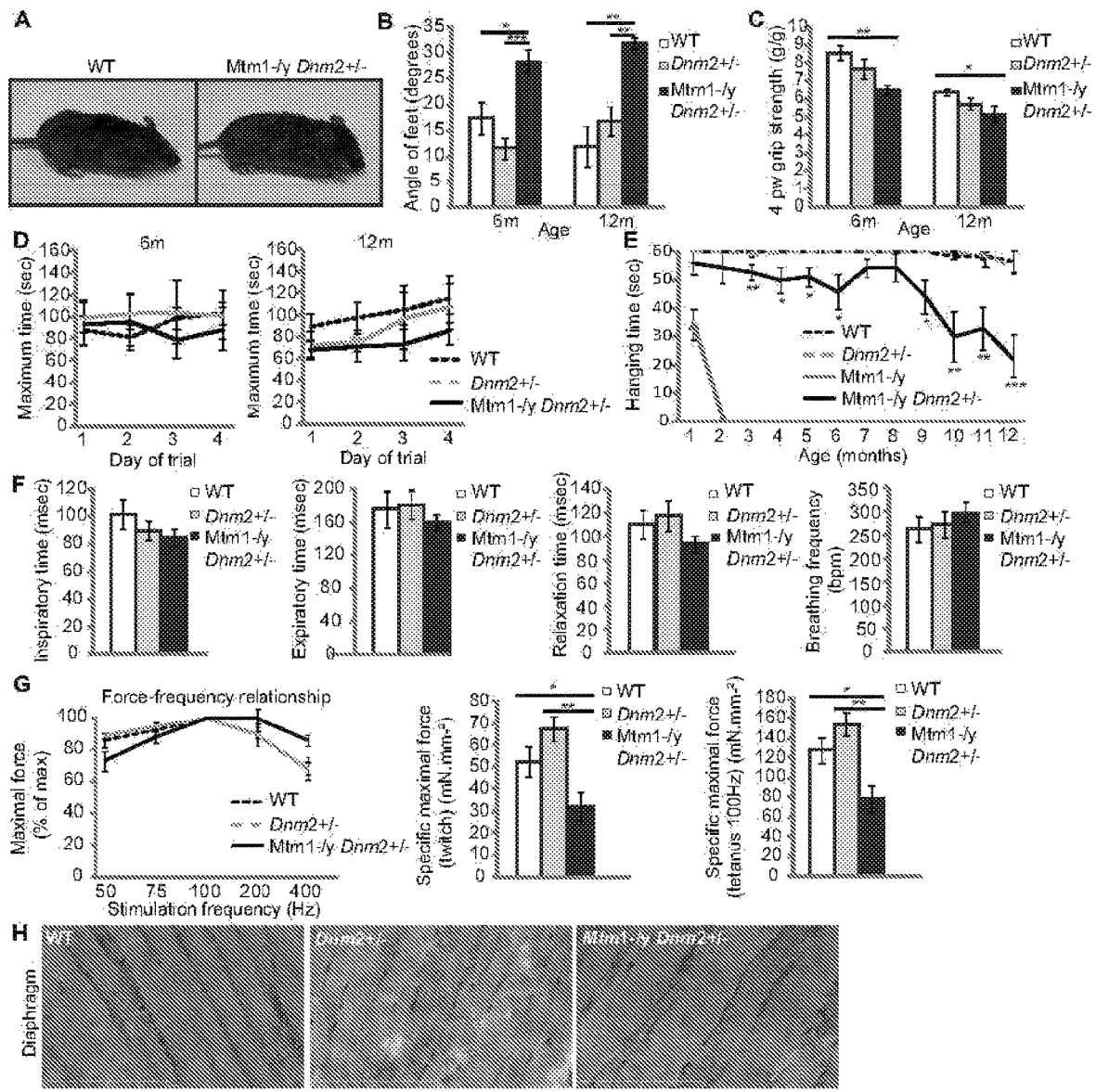
FIG. 7. Longterm phenotype of Mtm1−/y mice with reduced DNM2 expression. (A) A 12 month old WT (left) and Mtm1−/y Dnm2+/− (right) mouse. (B) Footprint test indicating the angle of separation between hindfeet. (C) 4 paw grip test. (D) Rotarod test performed under acceleration mode (4-40 rpm in 5 minutes). The time when mice fell off was recorded. Three trials per day/per mouse were recorded. (E) The hanging test requires mice to be suspended from a cage lid for up to 60 seconds. Three trials per mouse were performed. (F) A plethysmograph test for resting breathing measurements was performed on 6 month old mice. Inspiratory time, expiratory time, relaxation time, and breathing frequency are shown. (G) Diaphragm maximal muscle force was measured in strips of diaphragm from 6 month old mice. Force-frequency relationship, and specific maximal force under twitch and tetanus (100 Hz) are depicted. (H) Longitudinal diaphragm muscle sections were stained with HE and imaged by light microscopy. Scale bar 100 mm. All graphs depict mean±s.e.m. (*p<0.05, p<0.01, *p<0.001). n=minimum 5 mice.
Figure 16:
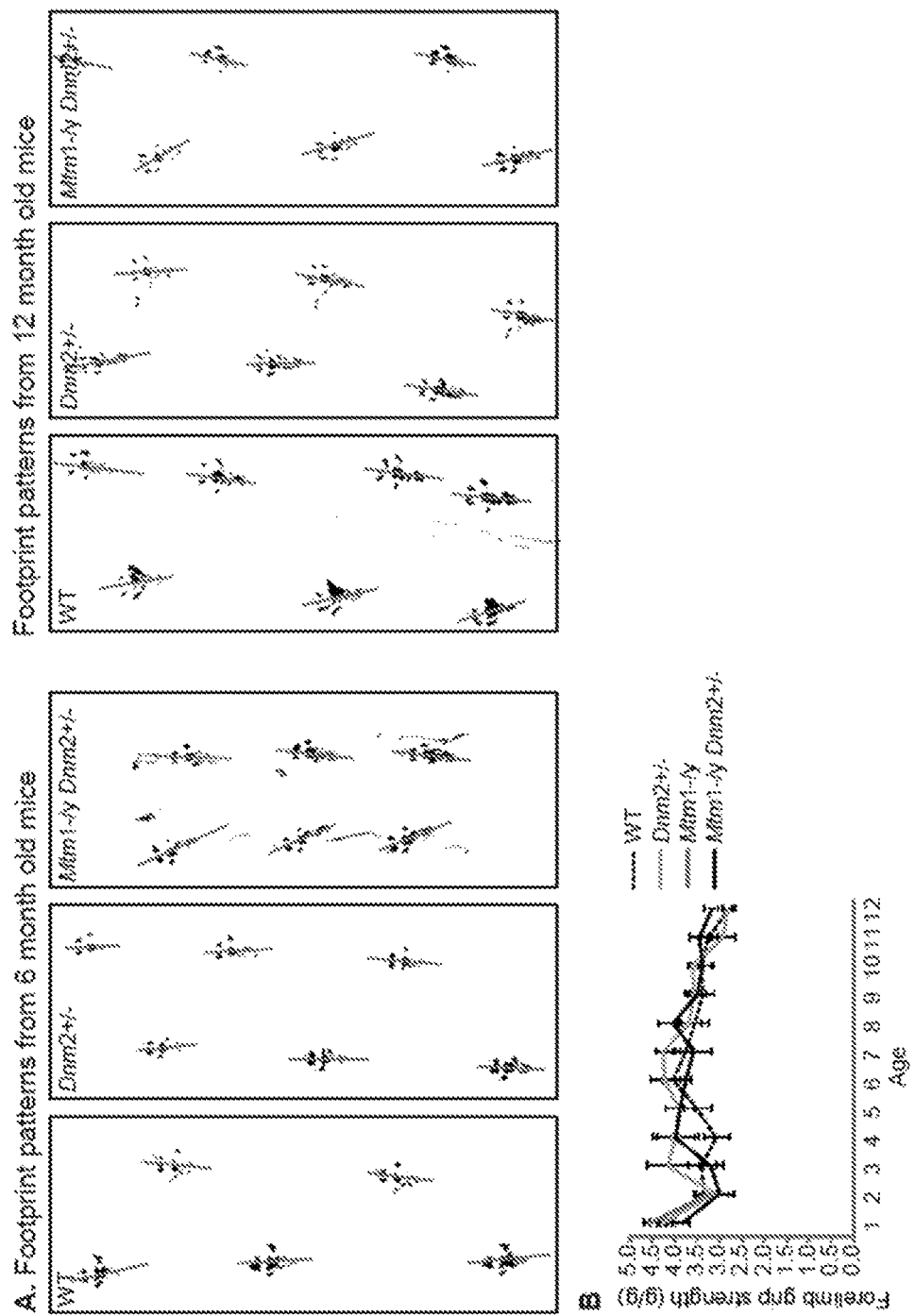
FIG. 16. Footprint patterns from 6 and 12 month old mice. A line of best fit is drawn to depict the angle measured between hindfeet. Notably Mtm1−/y Dnm2+/− walk with their feet turned out compared to WT and Dnm2+/− mice. Analyzed data is shown in FIG. 7B. (B) Forelimb grip test (front paws) was performed monthly (n=minimum 5 mice per group). Graph depicts mean±s.e.m. No significant difference was observed between groups.

XLCNM presents with very severe muscle weakness in patients and lethality in Mtm1−/y mice within 1-3 months; however, reducing dynamin 2 expression in these mice rescued the lifespan and greatly improved muscle strength at 8 and 16 w. The phenotype of Mtm1−/yDnm2+/− mice at later time points was determined to assess the extent of muscle function compatible with a normal lifespan. Mtm1−/yDnm2+/− mice aged 6 m and 12 m were able to move and perform basic tasks. Aged Mtm1−/yDnm2+/− mice looked similar to WT mice (FIG. 7A) but appeared to walk with hindfeet pointing outwards. This was quantified by placing the hindfeet in ink and measuring the angle between hindfeet when walking (FIG. 16A; FIG. 7B). This feature was not progressive from 6-12 m, as results were similar for both ages measured. To determine the overall maximal leg strength of these mice, the grip strength test was performed using a dynamometer. When only the two front paws were measured no difference was observed between WT or Mtm1−/yDnm2+/− during the first 12 months (FIG. S7B). When the four paws were measured, a small reduction in strength was observed in Mtm1−/yDnm2+/− mice compared to WT mice, at both 6 m and 12 m (FIG. 7C), indicating the hindlimbs of Mtm1−/yDnm2+/− mice exhibit reduced maximal muscle force compared to WT mice, which was not progressive. The rotarod test for general motor coordination, strength and endurance was performed, with no difference observed at 6 or 12 m (FIG. 7D), confirming the general coordination and overall strength of Mtm1−/yDnm2+/− was not severely perturbed. The hanging test is a strenuous test which requires the mouse to be suspended from a cage lid for 60 seconds. The severely affected Mtm1−/y mice were unable to perform this test after 1 month (FIG. 7E). In comparison aged Mtm1−/yDnm2+/− were able to perform this test up to the last age tested of 12 m, albeit to a lesser extent than WT and Dnm2+/− mice (FIG. 7E). As Mtm1−/yDnm2+/− mice are able to successfully perform basic motor strength tests up to 12 m, we conclude that the disease phenotype is not progressive overtime and lifespan and basic motor function are rescued.

Normal Long-Term Diaphragm Function in Mtm1−/y Dnm2+/− Mice.

Figure 13:
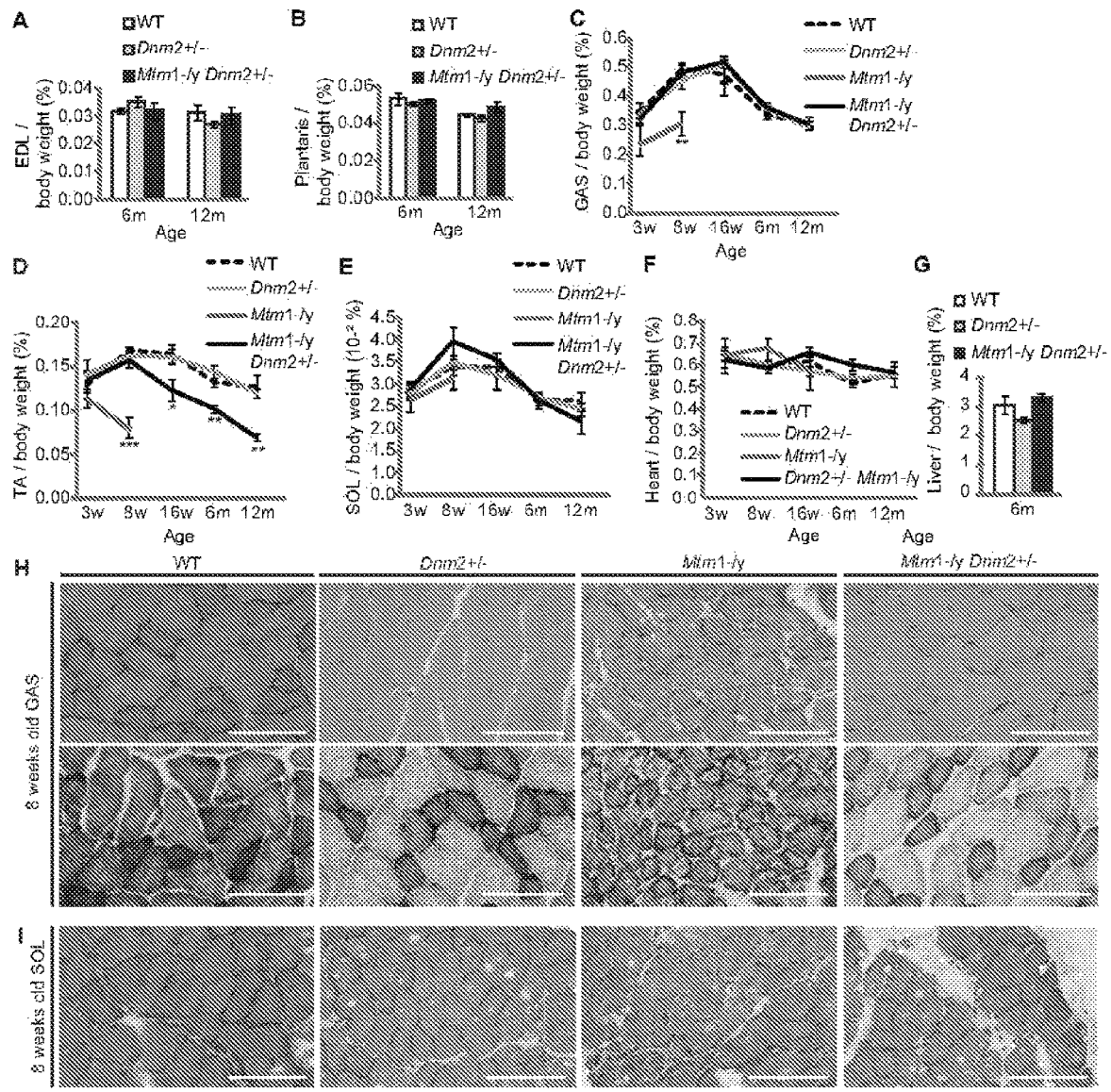
FIG. 13. Atrophy is rescued in skeletal muscles of Mtm1−/y mice with reduced dynamin 2 expression. EDL (A), plantaris (B), GAS (C), TA (D), SOL (E), heart (F), and liver (G) weights are reported as a percentage of total body weight (n=5-15 mice). All graphs depict mean±s.e.m. (*p<0.05, p<0.01, *p<0.001) (w=weeks of age, m=months of age). (H) Transverse GAS (H) or SOL (I) sections from 8 week old mice stained with HE (upper panel) or SDH (lower panel). Scale bar 100 μm.
Figure 17:
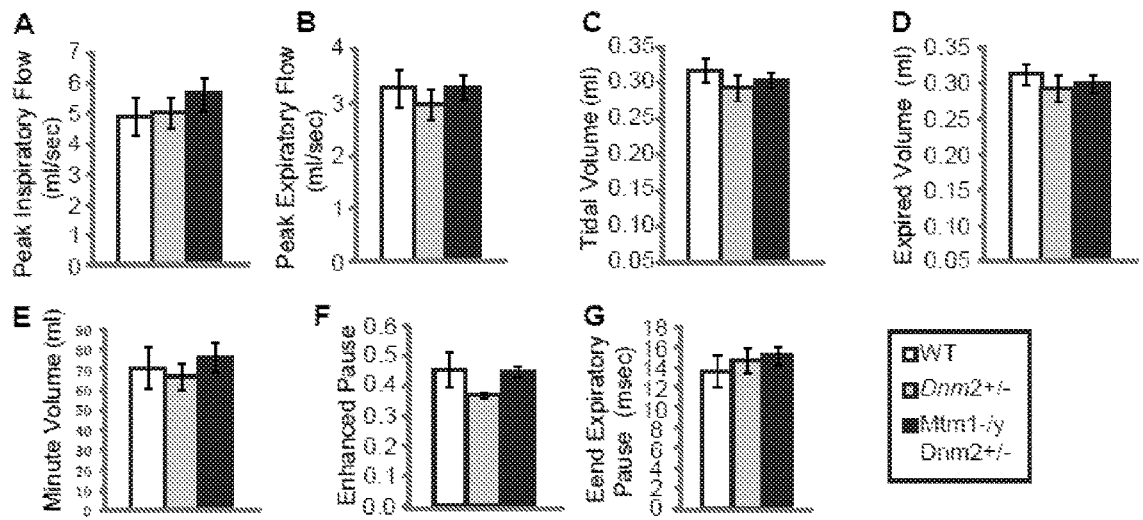
FIG. 17. Plethysmograph results for 6 mo Mtm1−/y mice with reduced dynamin 2 expression. The plethysmograph test was performed on resting mice to assess resting breathing patterns. All graphs depict mean±s.e.m. No significant difference was observed between groups.
Figure 18:
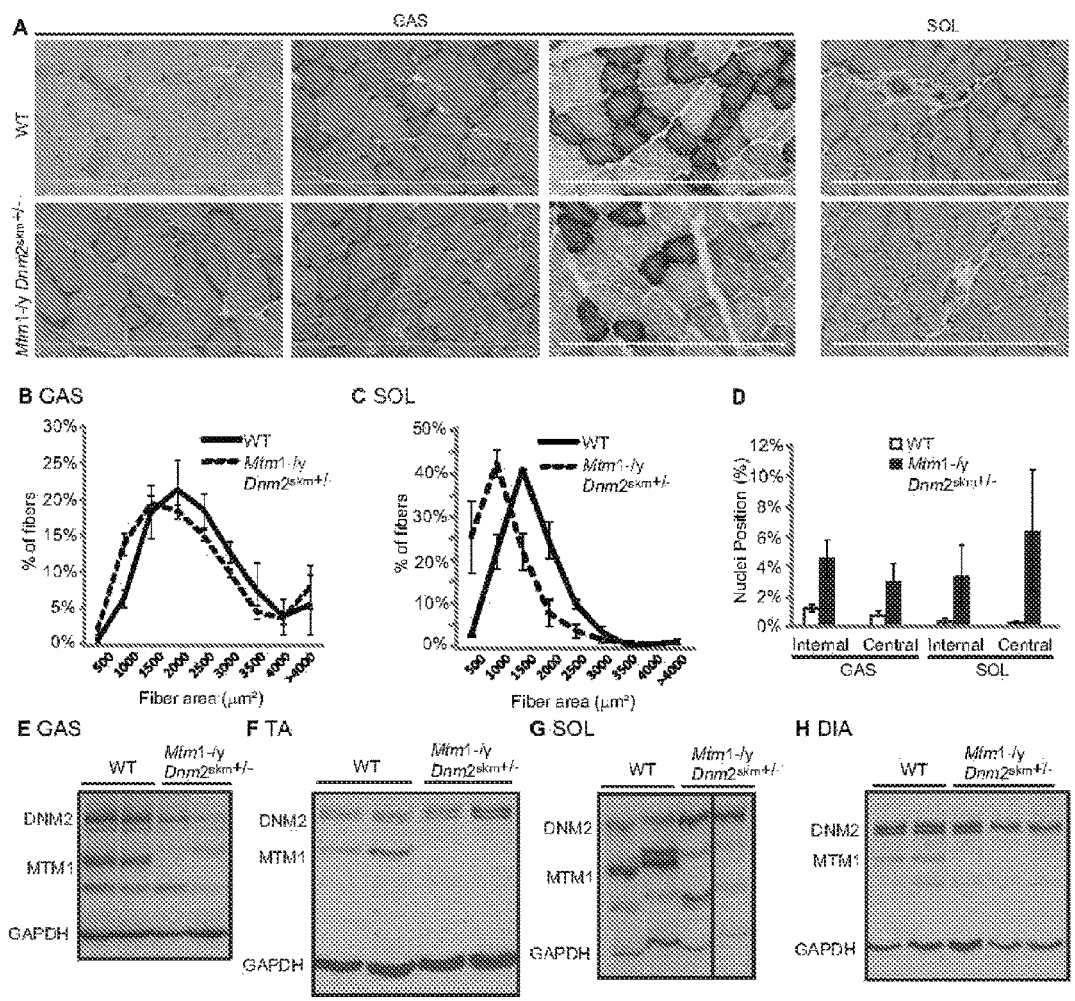
FIG. 18. Heterozygous deletion of dynamin 2 in skeletal muscle alone ameliorates the pathology of Mtm1−/y mice. (A) Transverse TA sections from 16 week old mice were stained with HE or SDH. Scale bar 300 μm. Transverse sections from 16 week old GAS (B) and SOL (C) muscles analyzed for fiber area. Fiber size is grouped into 500 μm$^2$ intervals, and represented as a percentage of total fibers in each group (n=3-6 mice). (D) The frequency of fibers with internal or central nuclei were counted (n=3-6 mice). Gastrocnemius (GAS)(E), tibialis anterior (TA) (F), soleus (SOL)(G), images shown are from the same western blot) and diaphragm (H) muscle lysates from 16 week old mice were immunoblotted for DNM2, MTM1 and GAPDH (loading control). All graphs depict mean+s.e.m. (*p<0.05, p<0.01, *p<0.001).
Figure 19:
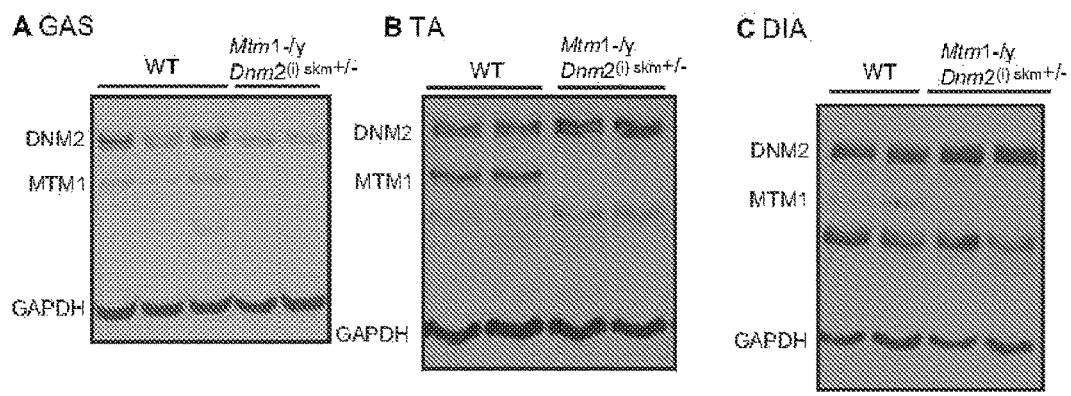
FIG. 19. Protein expression levels in Mtm1−/y Dnm2$^{skm+/-}$ mice. Gastrocnemius (GAS) (A), tibialis anterior (TA) (B), and diaphragm (C) skeletal muscle lysates from 16 week old mice were immunoblotted for DNM2, MTM1 and GAPDH (loading control).

It was shown that individual muscles appear to be differently affected in the Mtm1−/y XLCNM model and are differentially rescued by reduction of DNM2 (FIG. 2C-J; FIG. 13). The main concern for the longevity of patients with XLCNM is the ongoing function of the diaphragm as they have life-threatening respiratory failure (Jungbluth, H., Wallgren-Pettersson, C., and Laporte, J. 2008. Centronuclear (myotubular) myopathy. *Orphanet J Rare Dis* 3:26). In addition, the histology of the diaphragm in 5 w Mtm1−/y mice is strongly altered (FIG. 1G). The function of the diaphragm muscle in 6 m Mtm1−/yDnm2+/− mice was thus tested. The plethysmograph test was used to measure the spontaneous breathing pattern in mice under resting conditions. Mtm1−/yDnm2+/− mice performed similarly to WT and Dnm2+/− mice, with no significant difference detected (FIGS. 17 and 7F). The specific maximal force was measured on isolated strips of diaphragm muscle. No significant difference in the force-frequency relationship was detected, however a reduction in specific maximal force was observed (FIG. 7G). Histologically Mtm1−/yDnm2+/− diaphragm muscle resembled that of WT and Dnm2+/− muscle, with no major alterations to nuclei positioning or fibrosis observed (FIG. 7H). The diaphragm muscle of Mtm1−/yDnm2+/− mice sustained reduced DNM2 protein levels at 6 m (FIG. 2C), compared to Mtm1−/y mice in which DNM2 protein levels were elevated at 5 w (FIGS. 1E,F) and 8 w (FIG. 2C). Overall the diaphragm muscle of Mtm1−/yDnm2+/− mice was indistinguishable from control mice, supporting the extensive phenotypic amelioration of the XLCNM phenotypes upon DNM2 reduction.

Muscle Specific Reduction of DNM2 is Sufficient to Rescue the Phenotype and Improve the Lifespan in Mtm1−/y Mice.

Figure 8:
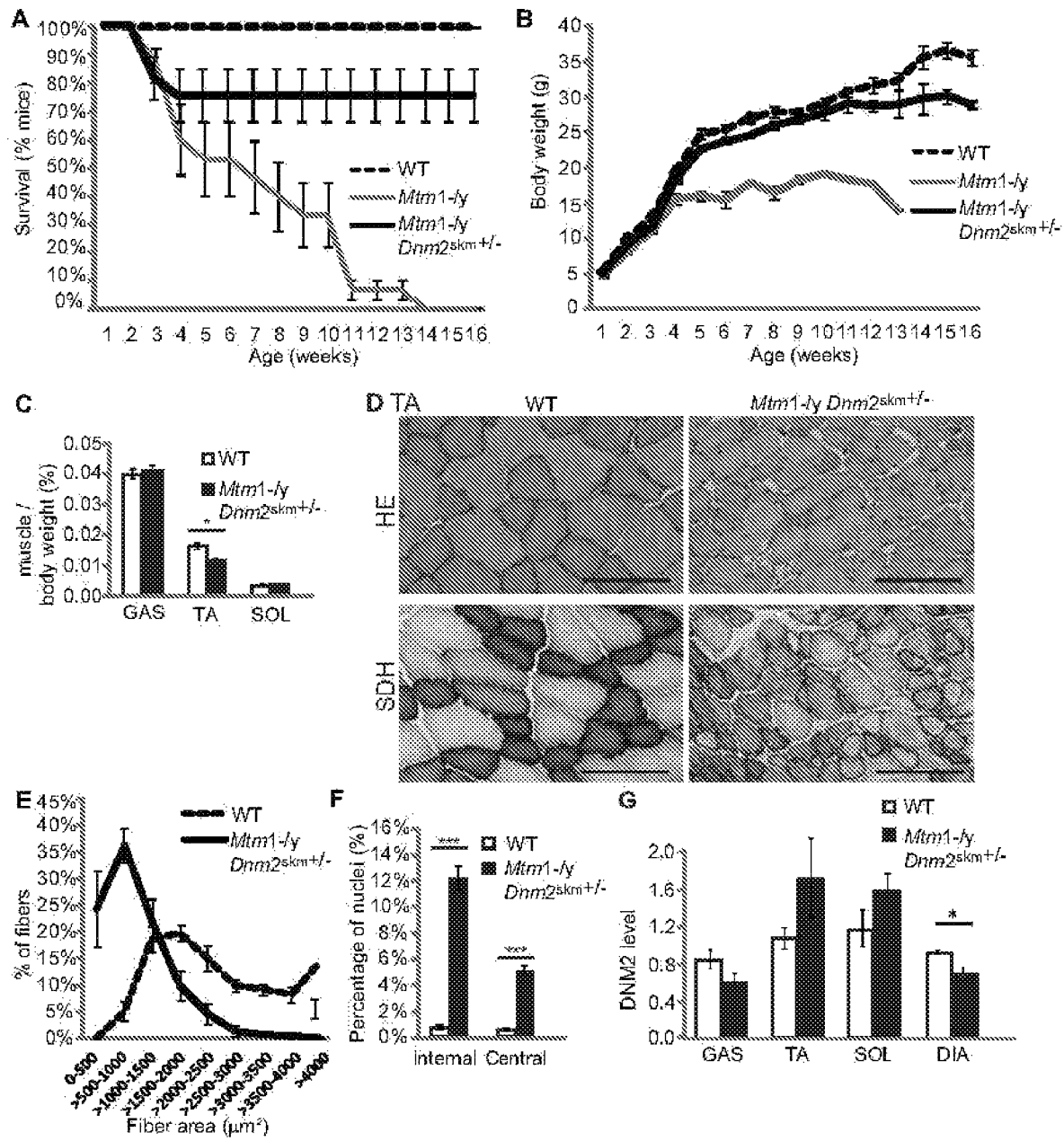
FIG. 8. Reducing DNM2 in skeletal muscle alone ameliorates the lifespan and pathology of Mtm1−/y mice. (A) Lifespan of all mice represented as a percentage of survival. Mtm1−/y mice with reduced DNM2 in muscle depicted as Mtm1−/y Dnm2skm+/−. (B) Bodyweight of mice. (C) Immediately after dissection gastrocnemius (GAS), tibialis anterior (TA) and soleus (SOL) muscles were weighed. Graphs represent muscle weight as a percentage of total body weight (n=5-12 mice). (D) Transverse TA sections from 16 week old mice were stained with HE (top panel) or SDH (lower panel). Scale bar 100 mm. (E) Transverse sections from 16 week old TA muscles analyzed for fiber area. Fiber size is grouped into 500 mm$^2$ intervals, and represented as a percentage of total fibers in each group (n=4-7 mice). (F) The frequency of fibers with internal or central nuclei were counted in TA muscle (n=4-7 mice). (G) Relative level of DNM2 protein determined by densitometry of DNM2 immunoreactive polypeptides, standardized to GAPDH loading. DNM2 level is represented as a fold difference from WT control lysate (n=4-7 mice). All graphs depict mean+s.e.m. (*p<0.05, p<0.01, *p<0.001).

In this study, we were able to fully rescue the lifespan of Mtm1−/y mice and most of the clinical and histological features of the disease, by reducing DNM2 expression in utero in all tissues. To test if the rescue of the muscle phenotype is cell-autonomous, human skeletal muscle α-actin (HSA)-Cre and HSA Cre-ER$^{T2}$ mice were obtained (Schuler, M. et al. 2005. Temporally controlled targeted somatic mutagenesis in skeletal muscles of the mouse. *Genesis* 41:165-170), which were crossed with floxed Dnm2 mice to produce Dnm2$^{skm+/−}$ (Cre positive) and Dnm2$^{(i)skm+/−}$ (Cre-ER$^{T2}$) heterozygous mice. These mice where then crossed with Mtm1−/y mice to produce tissue-specific excision of DNM2 in this background. When DNM2 expression was reduced in muscle (Mtm1−/yDnm2$^{skm+/−}$, HAS promoter active from 9 d.p.c. (Miniou, P. et al. 1999. Gene targeting restricted to mouse striated muscle lineage. *Nucleic Acids Res* 27:e27) lifespan of Mtm1−/yDnm2$^{skm+/−}$ mice was increased, with 75% of mice surviving until at least 16 weeks, whilst no Mtm1−/y mice survived to this age (FIG. 8A), consistent with the results from Mtm1−/yDnm2+/− mice (FIG. 2A). A cohort of 4 WT and 4 Mtm1−/y Dnm2$^{skm+/−}$ mice kept alive for future longterm analysis, and all mice are currently 9-12 months old. A corresponding increase in body weight was also observed in Mtm1−/yDnm2$^{skm+/-}$ mice compared to Mtm1−/y mice (FIG. 8B). No difference in mass of the gastrocnemius or soleus muscle was observed between Mtm1−/yDnm2$^{skm+/-}$ mice and WT mice (FIG. 8C). At 16 w when all Mtm1−/y littermates have died, the TA muscle of Mtm1−/yDnm2$^{skm+/-}$ mice exhibited some muscle atrophy, with a reduction in muscle mass and fiber size compared to WT littermates, which was associated with increased central and internal nuclei, and some abnormal SDH staining (FIG. 8D-F), similar to the TA muscle from 16 week old Mtm1−/yDnm2+/− mice (FIG. 2). These alterations were less pronounced than those seen in Mtm1−/y mice at 8 w. Importantly the gastrocnemius and soleus did not exhibit a significant difference in fiber size or nuclei position compared to WT mice (FIG. 18A-D), indicating the phenotype is rescued differently in different muscles. DNM2 protein levels were measured in different muscles at 16 w, and there was a significant reduction in DNM2 expression in the diaphragm, but not in other muscles measured compared to WT (FIGS. 8G, S9E-H). Mtm1−/y mice were not available at this age to compare the level of DNM2 that is increased at younger timepoints in these muscles (FIG. 2). As the diaphragm is a vital muscle required for breathing, the reduced DNM2 expression here may be important in the increased survival of Mtm1−/yDnm2$^{skm+/-}$ mice. Reduced DNM2 expression in the diaphragm muscle in Mtm1−/y mice appears critical to rescue XLCNM.

Muscle Specific Reduction of DNM2 after Birth is Sufficient to Rescue Mtm1−/y Mice.

Figure 3:
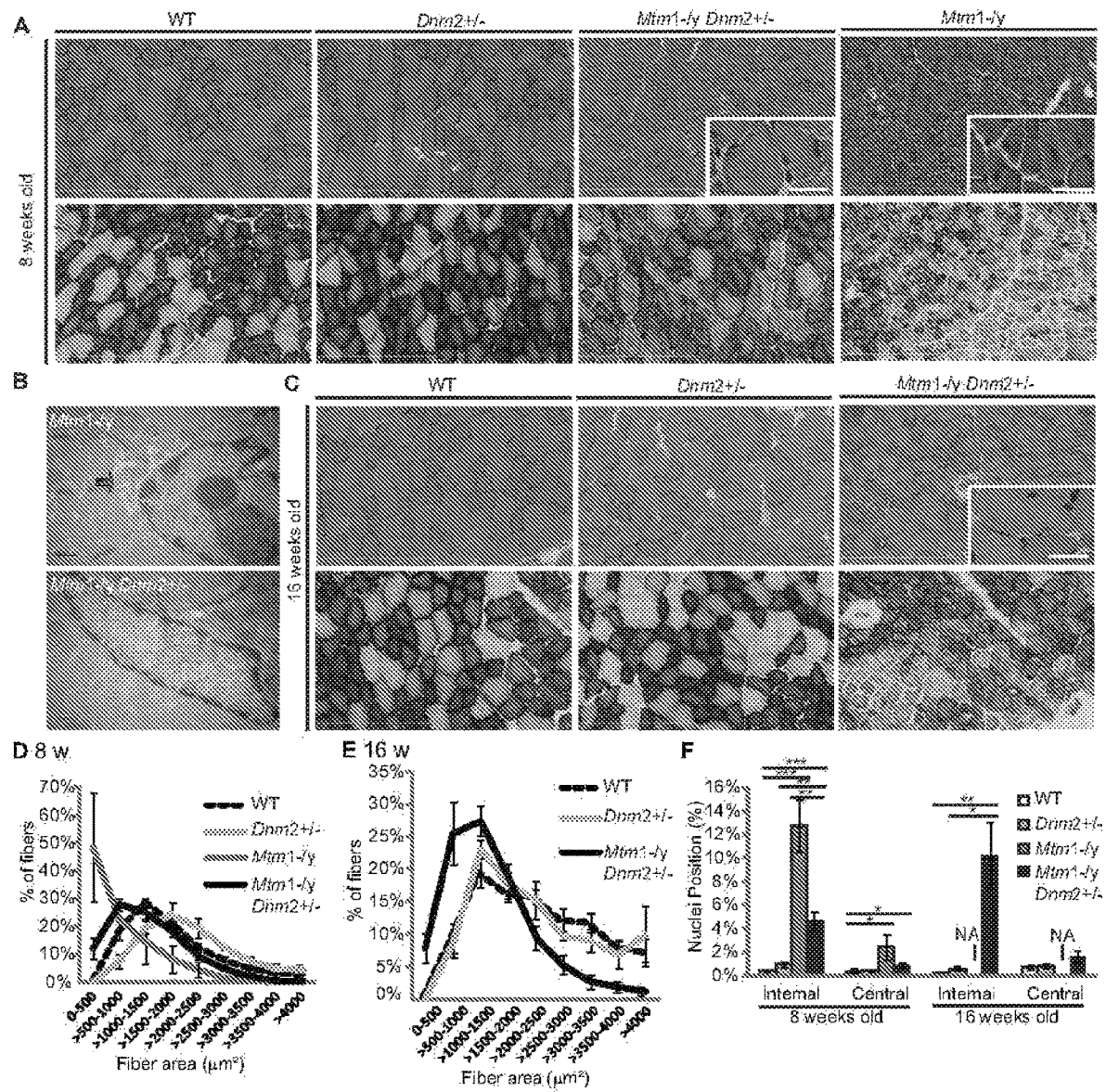
FIG. 3. CNM histological features are greatly rescued in Mtm1−/y mice with reduced DNM2 expression. Transverse TA sections from 8 (A) or 16 weeks old (C) mice were stained with haematoxylin and eosin (HE) (upper panel) or succinate dehydrogenase (SDH) (lower panel) and viewed by light microscopy. Scale bar 300 mm; high magnification scale bar 25 mm. (B) Transverse muscle sections were viewed by transmission electron microscopy. Arrow indicates membrane accumulation around nucleus. Scale bar 0.5 mm. Transverse muscle sections from 8 (D) and 16 weeks old (E) TA muscles were analyzed for fiber area. Fiber size is grouped into 500 $mm^2$ intervals, and represented as the percentage of total fibers in each group (n=5-7 mice). (F) The frequency of fibers with internal or central nuclei were scored (n=5 mice). Internal nuclei are defined as not subsarcolemmal nor central. Images and statistics were not measured in Mtm1−/y mice at 16 weeks old as they usually die before this age (marked NA for not applicable). All graphs depict mean±s.e.m. ($*p<0.05$, $p<0.01$, $*p<0.001$).
Figure 9:
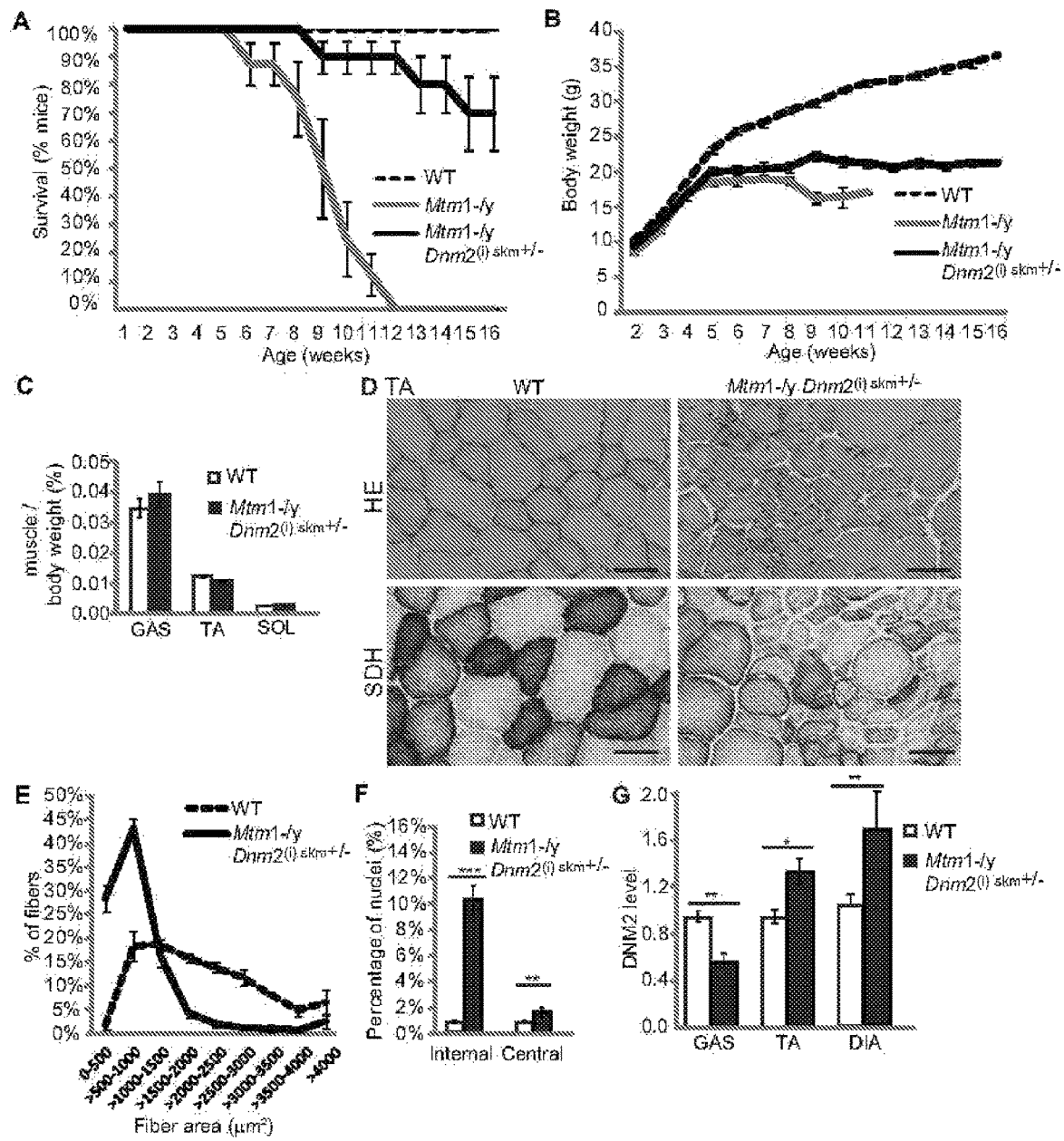
FIG. 9. Reducing DNM2 in skeletal muscle after the onset of symptoms ameliorates the lifespan and pathology of Mtm1−/y mice. (A) Lifespan of all mice represented as a percentage of survival. Mtm1−/y mice with reduced DNM2 in muscle depicted as Mtm1−/y Dnm2(i) skm+/−. (B) Bodyweight of mice. (C) Immediately after dissection gastrocnemius (GAS), tibialis anterior (TA) and soleus (SOL) muscles were weighed. Graphs represent muscle weight as a percentage of total body weight (n=5-12 mice). (D) Transverse TA sections from 16 week old mice were stained with HE (top panel) or SDH (lower panel). Scale bar 100 mm. (E) Transverse sections from 16 week old TA muscles analyzed for fiber area. Fiber size is grouped into 500 mm$^2$ intervals, and represented as a percentage of total fibers in each group (n=4-7 mice). (F) The frequency of fibers with internal or central nuclei were counted (n=4-7 mice). (G) Relative level of DNM2 protein determined by densitometry of DNM2 immunoreactive polypeptides, standardized to GAPDH loading. DNM2 level is represented as a fold difference from WT control lysate (n=5-7 mice). All graphs depict mean+ s.e.m. (*p<0.05, p<0.01, *p<0.001).

Mtm1−/y mice were crossed with Dnm2+/− mice under the HSA-Cre ER$^{T2}$ system to allow excision of DNM2 after birth in muscle, induced by tamoxifen injection (Schuler, M. et al. 2005. Temporally controlled targeted somatic mutagenesis in skeletal muscles of the mouse. *Genesis* 41:165-170). Importantly, tamoxifen injections were performed when mice were 3 weeks old, after the onset of symptoms like muscle atrophy (FIG. 2) and centralized nuclei (Al-Qusairi, L. et al. 2009. *Proc Natl Acad Sci USA* 106:18763-18768). 70% of the injected Mtm1−/yDnm2$^{(i)skm+/-}$ mice survived at least to 16 w (FIG. 9A). A higher body weight was observed compared to Mtm1−/y mice, however at 16 w body weight was still significantly reduced compared to WT mice (FIG. 9B). No difference in normalized mass of the gastrocnemius, soleus, or TA muscles was observed compared to WT mice at 16 w (FIG. 9C), unlike Mtm1−/y mice at earlier time points (FIG. 2). Further analysis of TA muscles from Mtm1−/yDnm2$^{(i)skm+/-}$ mice showed muscles exhibited some fiber hypotrophy (FIGS. 9D,E), associated with increased central and internal nuclei, and abnormal SDH staining (FIGS. 9D,F), similar to the TA muscle from 16 w Mtm1−/yDnm2+/− (FIG. 3). A decrease in DNM2 protein expression was noted in gastrocnemius muscles from Mtm1−/yDnm2$^{(i)skm+/-}$ mice at 16 w compared to WT mice, however an increase in DNM2 protein expression was observed in TA and diaphragm muscles (FIG. 9G, FIG. S10). These differences may be due to differential efficiency in DNM2 excision upon tamoxifen-mediated activation of the Cre recombinase. The increased DNM2 expression in the diaphragm at 16 w may be correlated with the reduced survival rate in Mtm1−/yDnm2$^{(i)skm+/-}$ mice from 8-16 weeks of age. Therefore one may conclude that reduction of DNM2 levels in muscle after birth, at an age when Mtm1−/y are affected, is sufficient to improve the lifespan and the CNM phenotype observed in Mtm1−/y mice.

Example 2

Materials and Methods are the same as, or equivalent to, the ones used in example 1.

The Bin1−/− mice is a mouse model for ARCNM and does not survive more than 24 hours after birth.

The Table 1 below show the results obtained with mice having different genotypes.

TABLE 1

| Genotype | Expected Mendelian ratio | Number of mice observed | Observed ratio |
| --- | --- | --- | --- |
| Wild type | 25% | 46 | 35% |
| Bin1+/− | 50% | 85 | 65% |
| Bin1−/− | 25% | 0 | 0% |

Bin1−/− mice die perinatally. Genotype counting a few days after birth of several litters obtained by crossing Bin1+/− males with Bin1+/− females, and showing absence of the Bin1−/− genotype.

Figure 20:
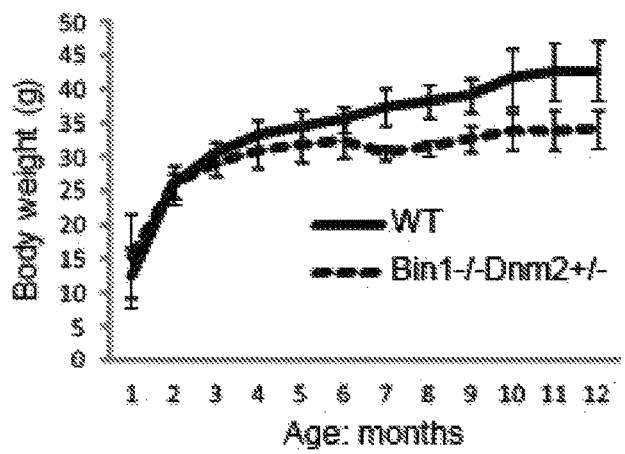
FIG. 20. Bin1−/− mice die perinatally while Bin1−/−Dnm2+/− mice survived and increase in body weight. —A. Body weights in grams show the Bin1−/− Dnm2+/− mice reach 34 grams. —B. 10 weeks old wild type and Bin1−/− Dnm2+/− mice are indistinguishable.
Figure 20:
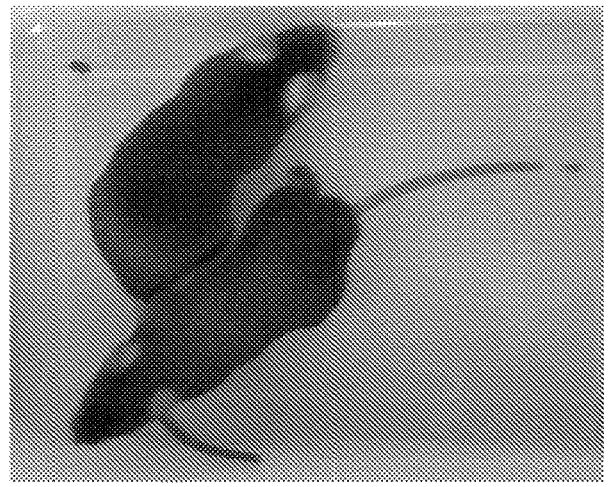
Figure 21:
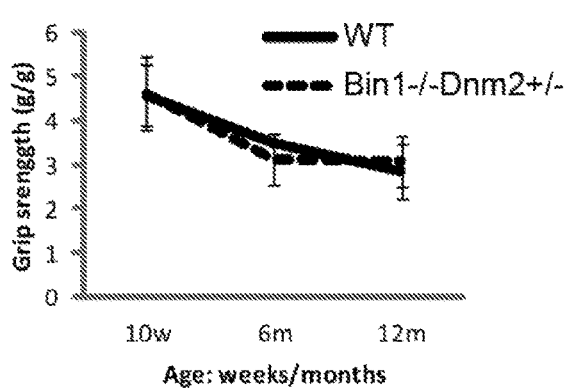
FIG. 21. Bin1−/−Dnm2+/− mice exhibit no performance deficits in clinical analysis compared to wild type (WT mice). (A-F) Young (2-6 months) and old (12-17 months) Bin1−/− Dnm2+/− mice were analyzed. (G-H) Specific maximal force (absolute maximal force compared to muscle weight) and half relaxation time are similar at both ages in Bin1−/− Dnm2+/− and wild type (WT) mice, supporting normal muscle force and resistance to fatigue.
Figure 21:
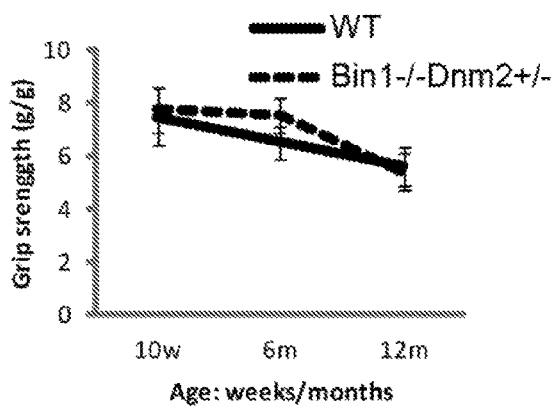
Figure 21:
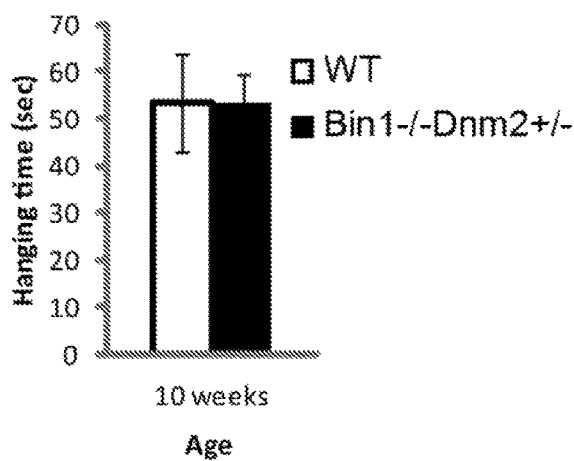
Figure 21:
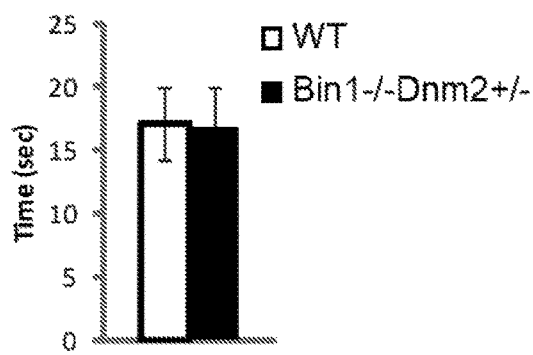
Figure 21:
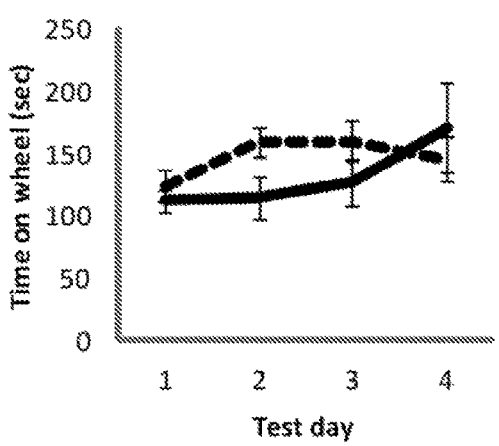
Figure 21:
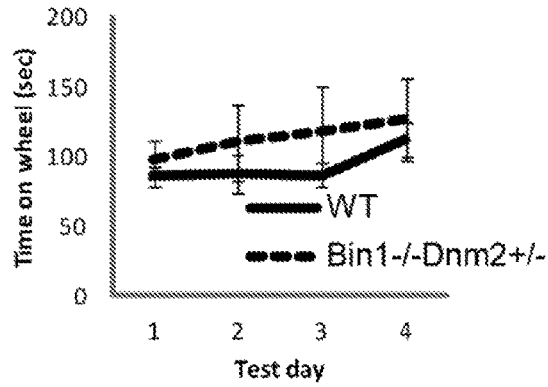
Figure 21:
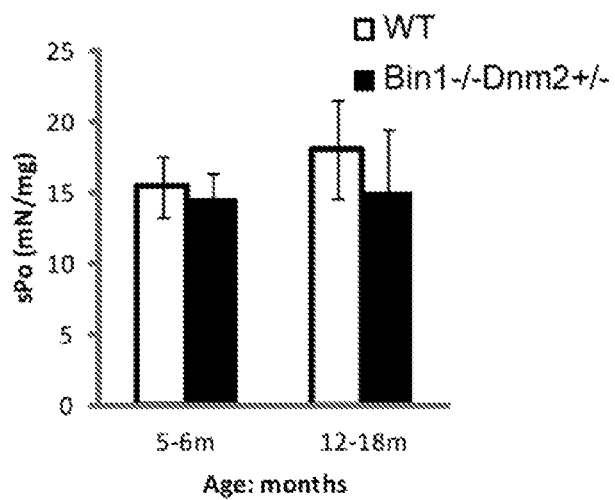
Figure 21:
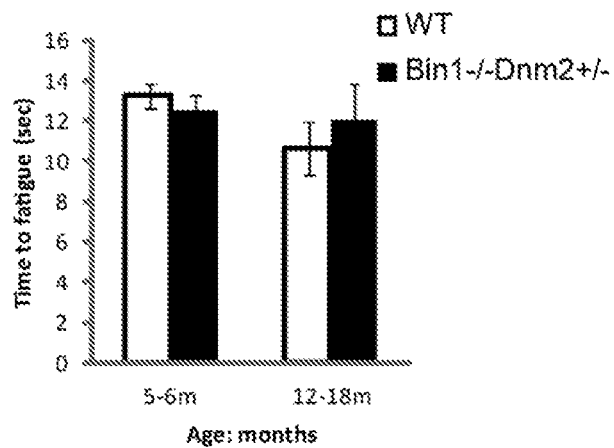
Figure 22:
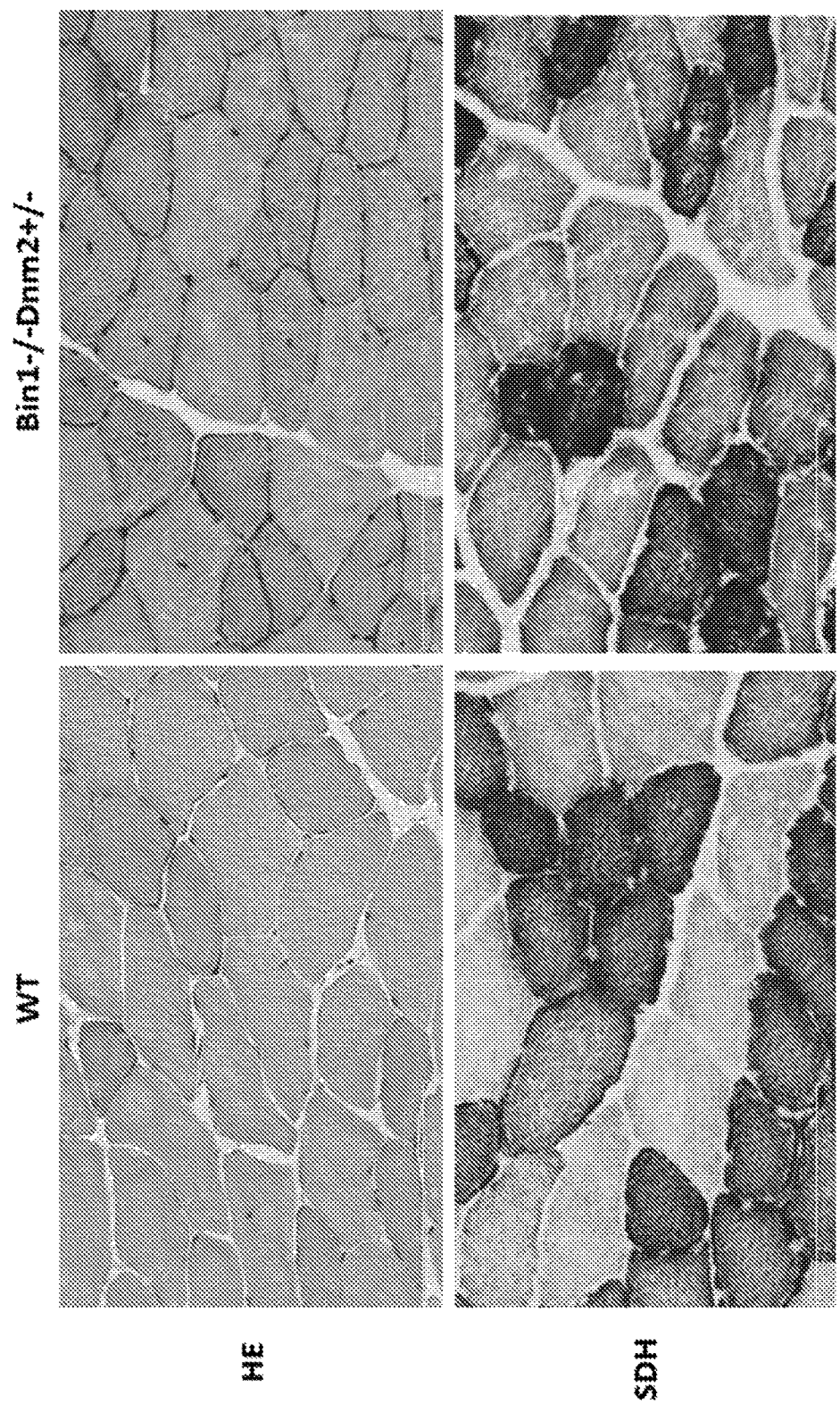
FIG. 22. Bin1−/−Dnm2+/− mice exhibit histology close to controls. Bin1−/−Dnm2+/− mice display muscle fibers with normal shape and size (HE: hematoxylin-eosin staining) and normal oxidative staining (SDH). They have a tendency to show more centralized nuclei without sign of excessive regeneration.
Figure 23:
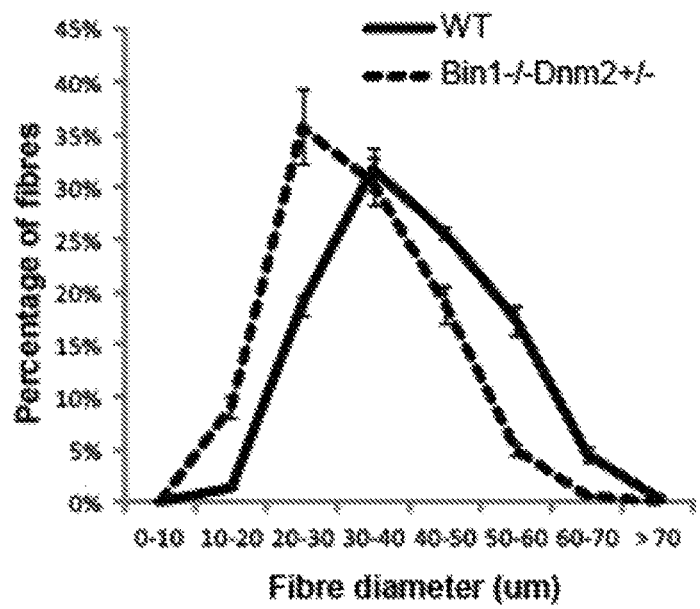
FIG. 23. Fiber size (A) and nuclei position (B). Bin1−/−Dnm2+/− mice exhibit similar fiber size with a slight tendency toward smaller fibers that is not significant when the mean of all fibers diameter is compared (left). Bin1−/−Dnm2+/− mice have more centralized nuclei (right).
Figure 23:
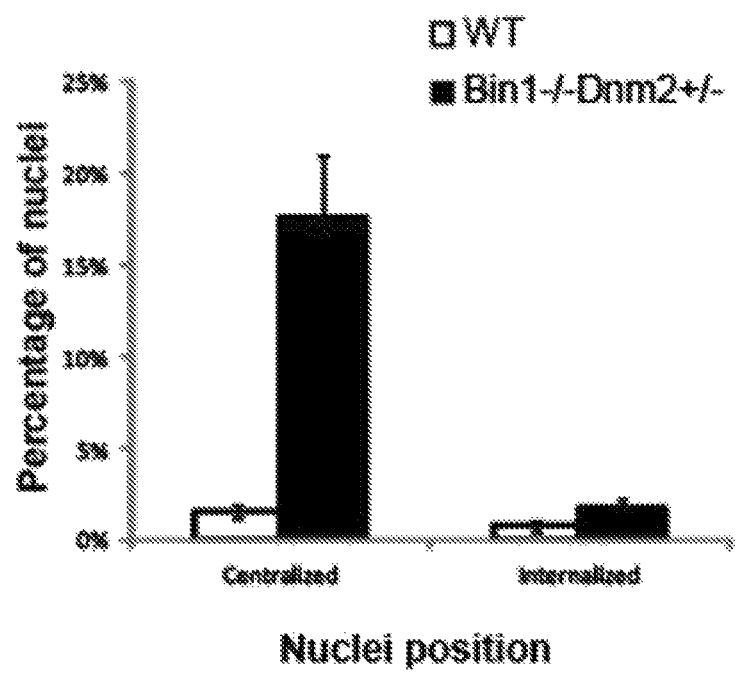
Figure 24:
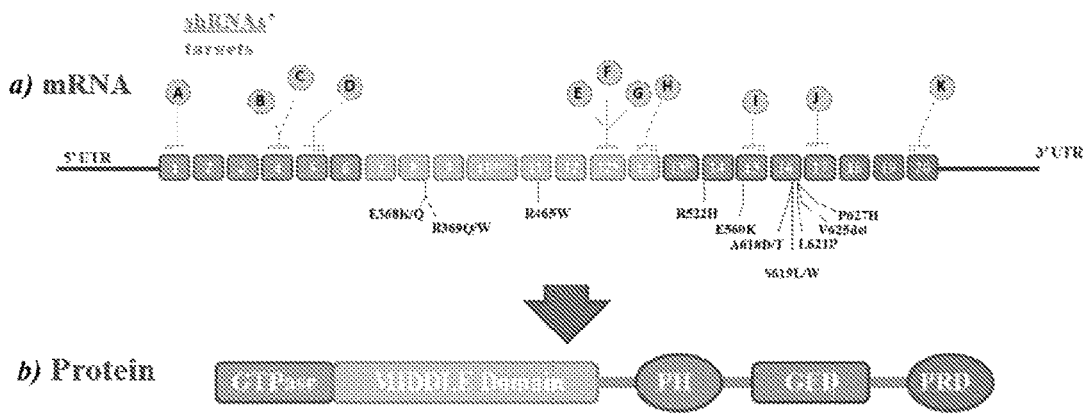
FIG. 24. Dynamin 2 mRNA exons & dynamin 2 protein domains: a) Dynamin2 mRNA regions that were chosen to be targeted by shRNA (above), dominant mutations in DNM2 that lead to centronuclear myopathy (below). b) GTPase domain, middle (MID), pleckstrin homology (PH) domain, GTPase effector domain (GED), and proline rich domain (PRD).
Figure 25:
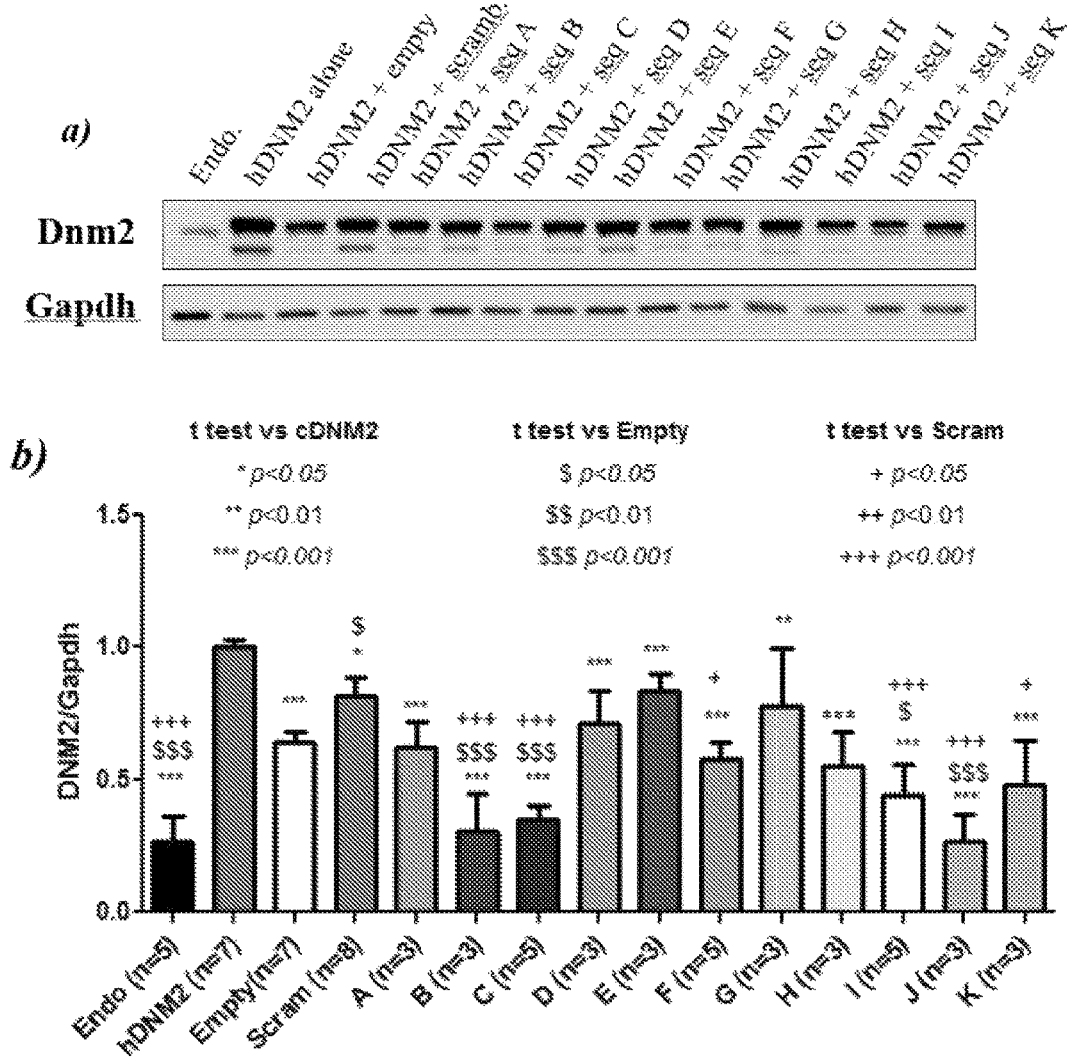
FIG. 25. Dynamin 2 protein expression in shDnm2-transfected HEK cells. a) Western-blot of co-transfected HEK (human embryonic kidney) cells with hDNM2 (plasmid encoding for human DNM2) and shRNA targeting DNM2 mRNA. b) Densitometry analysis shows that shRNA N° B, C, F, I and J target hDNM2 and reduced efficaciously its expression.
Figure 26:
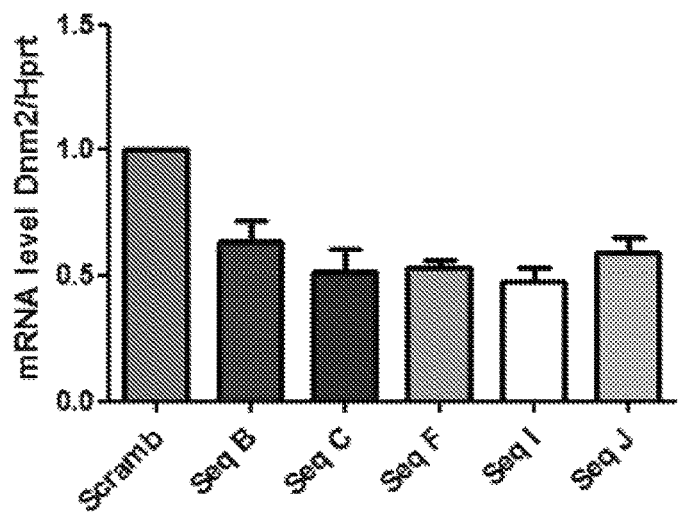
FIG. 26. Dynamin2 mRNA expression in shDnm2-transfected C2C12 cells. Dnm2 mRNA level was assessed in shRNA-transfected C2C12 (mouse myoblast). Selected shRNA reduced efficiently the Dnm2 mRNA to around 50%.

As an illustration that downregulation of DNM2 can significantly ameliorate the phenotypes of a mouse model for ARCNM (the Bin1−/− mouse), a 50% decrease of Dynamin 2 in the Bin1−/− mouse can efficiently rescue the early lethality, leading to the survival of Bin1−/−Dnm2+/− mice for at least 12 months (FIG. 20), which have a sub-normal body weight (FIG. 20) and a normal specific muscle force, resistance to fatigue and force and coordination behaviours (FIG. 21). Histological examinations and quantification show Bin1−/−Dnm2+/− muscles have normal fiber shape and size up to at least 12 months old, normal oxidative staining, and a slight increase in central nuclei without sign of excessive regeneration (FIGS. 22-23).

Thus DNM2 decrease can significantly ameliorate several forms of CNM in mice (XLCNM in the Mtm1−/y mice and ARCNM in the Bin1−/− mice).

Example 3

Materials and Methods
Production and Purification of AAV:
AAV2/9 vectors were generated by a triple transfection of AAV-293 cell line with pAAV2 insert containing the insert under the control of the CMV promoter and flanked by serotype 2 inverted terminal repeats, pXR1 containing rep and cap genes of AAV serotype 9, and pHelper encoding the adenovirus helper functions. Cell lysates were subjected to 3 freeze/thaw cycles, then treated with 50 U/mL of Benzonase (Sigma) for 30 minutes at 37° C., and clarified by centrifugation. Viral vectors were purified by Iodixanol gradient ultracentrifugation followed by dialysis and concentration against Dulbecco's Phosphate Buffered Saline using centrifugal filters (Amicon Ultra-15 Centrifugal Filter Devices 30K, Millipore, Bedford). Physical particles were quantified by real-time PCR using a plasmid standard pAAV-eGFP, and titers are expressed as viral genomes per milliliter (vg/mL). rAAV titers used in these experiments were 5 to 7 10$^{11}$ vg/mL.

AAV Transduction of Wild-Type Tibialis Anterior (T.A) and Gastrocnemius Muscles of Mice:

3-week-old, male, wild-type, 129PAS mice were anesthetized by i.p. injection of 5 μl/g of ketamine (20 mg/mL;

Virbac, Carros, France) and xylazine (0.4%, Rompun; Bayer, Wuppertal, Germany). Left leg muscles were injected with 25 µl of AAV2/9 shDnm2 N° C. while right leg muscles were with the same amount of AAV2/9 of scrambled. Animals were housed in a temperature-controlled room (19° C. to 22° C.) with a 12:12-hour light/dark cycle. Mice were sacrificed by $CO_2$ inhalation followed by cervical dislocation, according to national and European legislations on animal experimentation. The TA and Gast. muscles were dissected 5 weeks post injection, weighed and frozen in nitrogen-cooled isopentane and liquid nitrogen for histology.

Histology Assessment:

8 µm transverse sections were prepared, fixed and stained by H&E (haematoxylin & eosin). Fiber size was analyzed from H&E sections using the software Fiji. The percentage of TA muscle fibers with centralized or internalized nuclei was counted using the cell counter plugin in Fiji image analysis software. The fiber area was measured using the Fiji software. More than 800 fibers were counted and measured for each sample.

Cells Transfection:

HEK (human embryonic Kidney) cells were co-transfected with plasmid encoding for shDnm2 and plasmid encoding for muscle specific isoform hDNM2 (human DNM2) using lipofectamine2000 purchased from Thermo Fisher Scientific. C2C12 mouse myoblast were electroporated with plasmid encoding for shDnm2 using Amaxa kit V Cell Line Nucleofector™ purchased from Lonza.

Table 2: Sequences and potential off-target for shRNA against the DNM2 gene.

Exon 12b of Dynamin2 mRNA has the following sequence:

SEQ ID No 30: 5' ctgttactat actgagcagc tggtgacctg 3', or corresponds to the encoded protein sequence SEQ ID No 31: (Cys Tyr Tyr Thr Glu Gln Leu Val Thr Cys).

The target DNM2 sequences are 100% homologous to murine Dnm2 and human DNM2. No off-target genes have a homology higher than 80%, precluding efficient down-regulation of off-targets.

TABLE 2

| shRNA against DNM2 | Target sequence | Dnm2 Exon target | Potential off-target in human and % of homology | Potential off-target in mouse and % of homology |
| --- | --- | --- | --- | --- |
| A | AACCGCGGGATGGAAG AGCT (SEQ ID NO: 16) | 1 | ceramide synthase 2 (CERS2) 70% | phosphatase 1F (PP2C domain containing) (Ppm1f) 70% |
| B | AACTTGACCCTCATCG ACCTC (SEQ ID NO: 17) | 4 | DnaJ (Hsp40) homolog, subfamily C, member 2 (DNAJC2) 71% | potassium voltage-gated channel, subfamily G, member 1 (Kcng1) 76% |
| C | AAGGACATGATCCTGC AGTTCAT (SEQ ID NO: 2) | 4 | myosin IE (MYO1E) 43% | potassium voltage-gated channel, subfamily G, member 1 (Kcng1) 52% |
| D | TCGGTGTCATCACCAA GCT (SEQ ID NO: 18) | 5 | Dynamin1 73% | myosin IE (MYO1E) 78% |
| E | TGCCAACTGTTTCTATA CT (SEQ ID NO: 19) | 12b | multiple PDZ domain protein (MPDZ) 73% | folliculin interacting protein 1 (Fnip1) 73% |
| F | AACTGTTTCTATACTGA GGAG (SEQ ID NO: 20) | 12b | GTP cyclohydrolase 1 (GCH1) 76% | protocadherin 17 (Pcdh17) 71% |
| G | TTTCTATACTGAGGAG CTGGT (SEQ ID NO: 21) | 12b | THUMP domain containing 1 71% | WNK lysine deficient protein kinase 2 (Wnlc2) 71% |
| H | GCACGCAGCTGAACAA GAA (SEQ ID NO: 22) | 13 | tensin 3 (TNS3) 78% | HGF-regulated tyrosine kinase substrate (Hgs) 78% |
| I | AAGAAGTACATGCTGC CTCTGA (SEQ ID NO: 23) | 15 | SKI family transcriptional corepressor 1 (SKOR1) 69% | zinc finger, C3H1-type containing (Zfc3h1) and DENN/MADD domain containing 5A (Dennd5a) 69% |
| J | AACACCTTCTCCATGG ACCC (SEQ ID NO: 24) | 17 | GTP cyclohydrolase 1 (GCH1) 80% | GTP cyclohydrolase 1 (Gch1) 75% |
| K | CCATTATCCGCCCAGC CGAGC (SEQ ID NO: 25) | 21 | | |

Figure 27:
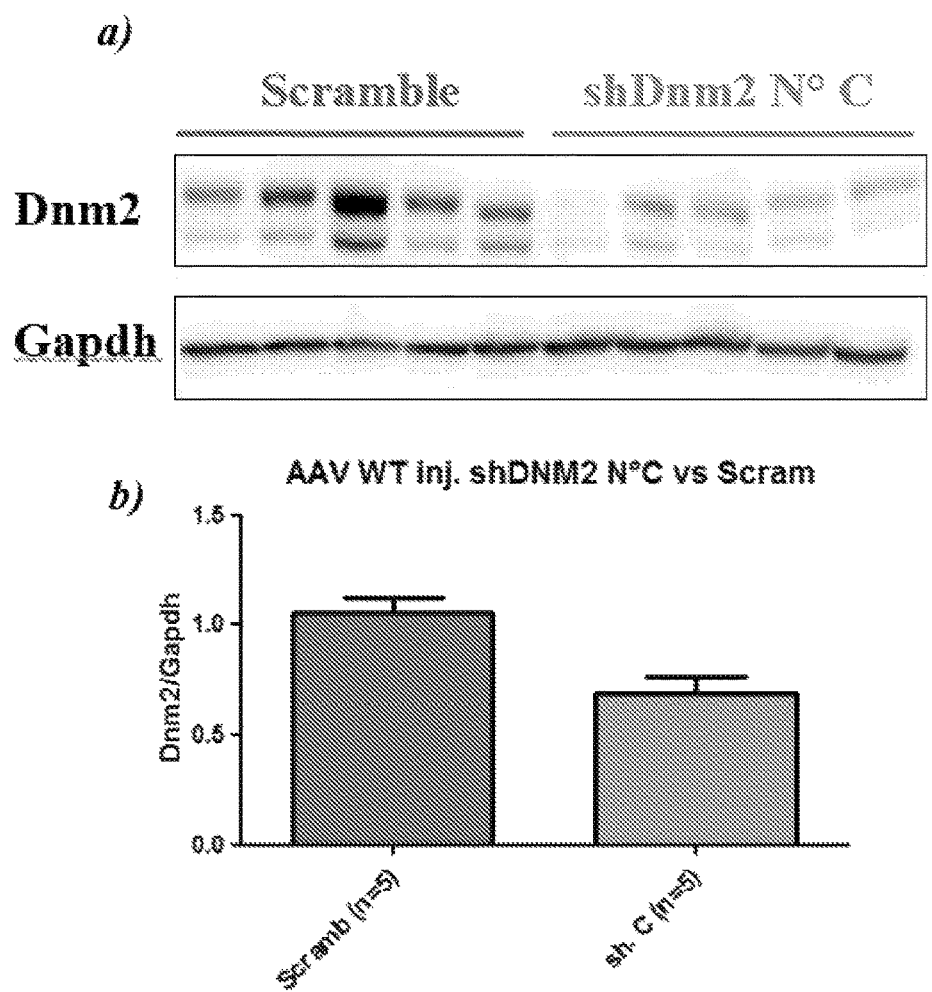
FIG. 27. Dynamin 2 protein expression in AAV-injected WT(wild-type) TA (Tibialis Anterior) muscle. a) Western-blot of WT TA injected with AAV expressing either shDnm2 N° C. or scrambled sequence. b) Densitometry analysis shows that shRNA N° C. targets Dnm2 in vivo and reduced its expression at around 60% compared to WT injected with AAV-scrambled.
Figure 28:
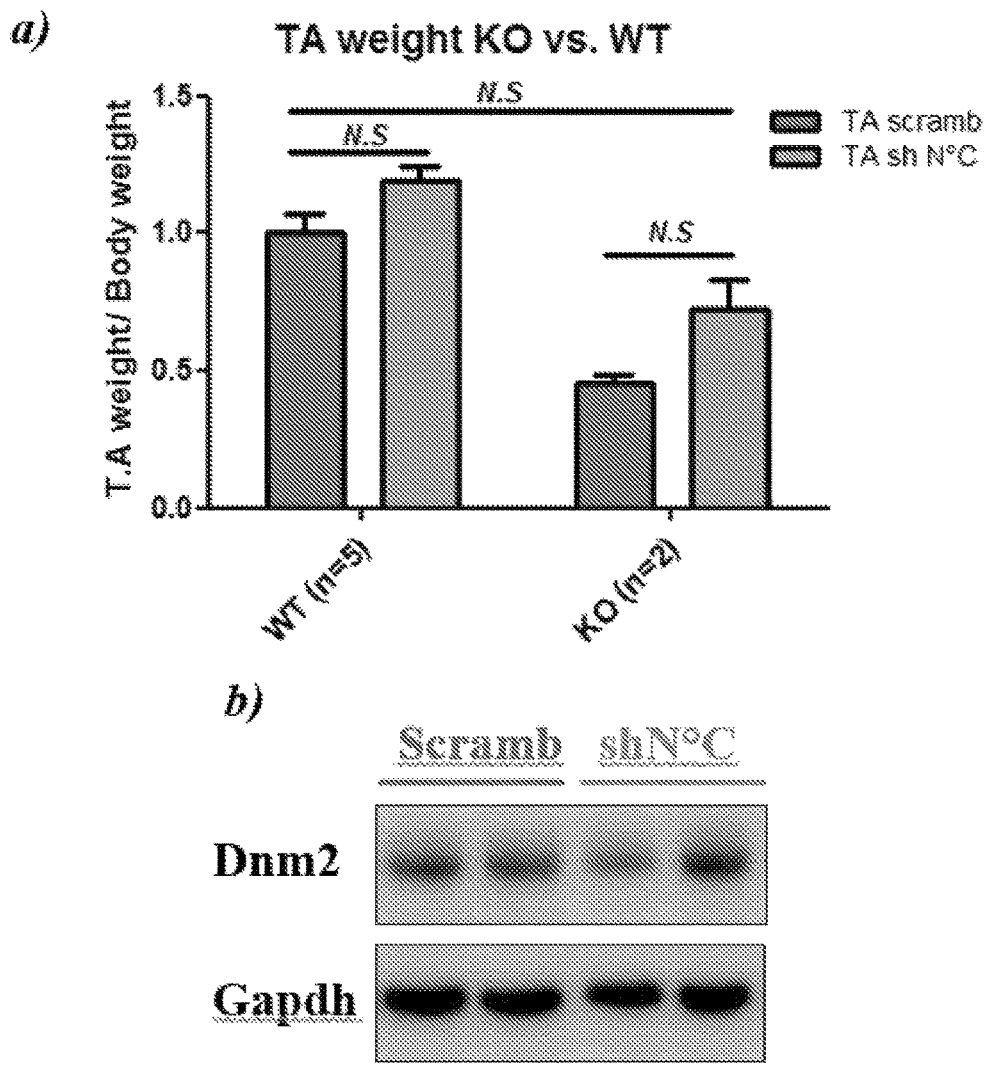
FIG. 28. Mtm1−/y KO TAs weight and Dnm2 protein expression after 5 weeks of AAV intramuscular injection. a) Intramuscular injection of AAV encoding shDnm2 N° C. shows a gain of muscle weight compared to TA injected with AAV-scrambled. b) Western-blot of Mtm1−/y KO Gastrocnemius injected with AAV expressing either shDnm2 N° C. or scrambled sequence FIG. 29. Mtm1−/y KO Gastrocnemius muscle cross-sections stained with H&E (Hematoxylin & Eosin) after 5 weeks of AAV intramuscular injection. Intramuscular injection of AAV encoding shDnm2 N° C. (right) shows an improvement of muscle histology and increased fiber size in Mtm1−/y KO Gastrocnemius compared to Mtm1−/y KO Gastrocnemius injected with AAV-scrambled sequence (left)
Figure 29:
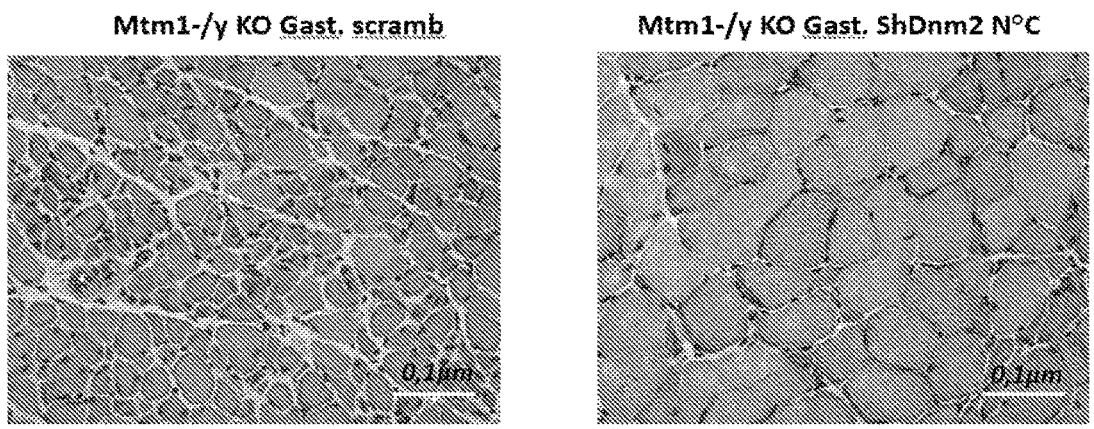
Figure 30:
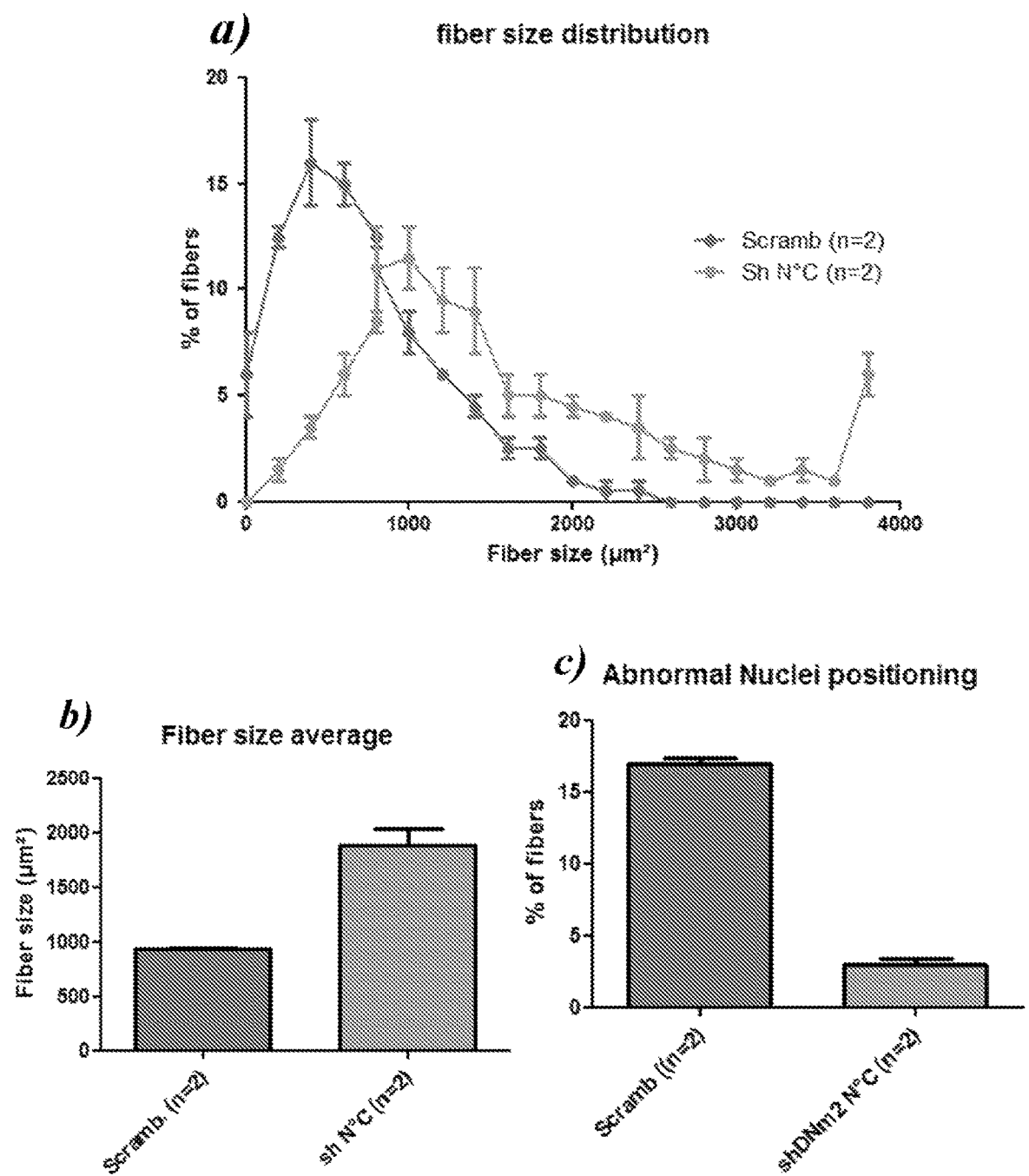
FIG. 30. Fiber size distribution, fiber size average & quantification of nuclei position in Mtm1−/y KO Gastrocnemius muscle cross-sections injected with AAVs. a) Fiber size distribution shows that Mtm1−/y KO Gastrocnemius injected with AAV-shDnm2 N° C. presented more large fibers compared to Mtm1−/y KO Gastrocnemius injected with AAV-scrambled. b) Fiber size average measurement demonstrates that Mtm1−/y KO Gastrocnemius injected with AAV-shDnm2 exhibit larger fibers (nearly doubling in size) compared to Mtm1−/y KO Gastrocnemius injected with AAV-scrambled. c) Mtm1−/y KO Gastrocnemius injected with AAV-shDnm2 N° C. present less abnormal position of nuclei within muscle fibers compared to Mtm1−/y KO Gastrocnemius injected with AAV-scrambled. >800 fibers were measured for (a) & (b). 1000 fibers were counted for each sample for (c)

Results (FIGS. 24-30)

examples of shRNA targeting specifically the DNM2 sequence (FIG. 24) and that can efficiently decreased Dynamin 2 level in transfected HEK cells (FIG. 25), in transfected C2C12 murine myoblasts (FIG. 26), in tibialis anterior of wild-type mice injected with an AAV expressing a shRNA targeting DNM2 (FIG. 27; AAGGACATGATCCTGCAGTTCAT: SEQ C or SEQ ID No2).

examples of a phenotypic amelioration in the Mtm1−/y KO mice model for XLCNM 5 weeks after the injection of an AAV expressing a shRNA targeting DNM2 (AAGGACATGATCCTGCAGTTCAT—SEQ C or SEQ ID No2) into the tibialis anterior (TA) and gastrocnemius muscles: compared to the injection of a control scrambled shRNA, the shRNA targeting DNM2 ameliorates the weight of injected muscles (FIG. 28), the general histology (FIG. 29), increases fiber size on qualitative and quantitative assessments (FIGS. 29 and 30), and nuclei positioning (FIG. 30).

The invention claimed is:

1. A method for the treatment of a X-linked centronuclear myopathy (XL-CNM) in a subject in need of said treatment, said method comprising administering to said subject in need of said treatment a therapeutically efficient amount of an inhibitor of Dynamin 2, said inhibitor being a RNAi, an antisense nucleic acid, a siRNA, a shRNA or a ribozyme interfering specifically with Dynamin 2 expression.

2. The method according to claim 1, wherein the Dynamin 2 inhibitor is an antisense nucleotide inducing exon-skipping within a Dynamin 2 pre-mRNA.

3. The method according to claim 2, wherein the Dynamin 2 inhibitor is an antisense nucleotide designed to specifically induce DNM2 exon 2 or exon 8 skipping.

4. The method according to claim 3, wherein said antisense nucleotide comprises SEQ ID NO: 26 or SEQ ID NO: 27.

5. The method according to claim 1, wherein the Dynamin 2 inhibitor is a nucleic acid molecule specifically interfering with Dynamin 2 and comprises a sequence selected from the group consisting of SEQ ID NOs: 2-25.

6. The method according to claim 1, wherein the inhibitor is administered in an amount sufficient to reduce the Dynamin 2 expression or the Dynamin 2 activity, expression or function in a level equal to or less than the normal level.

7. The method according to claim 1, wherein said X-linked centronuclear myopathy is due to MTM1 mutations.

* * * * *

UNITED STATES PATENT AND TRADEMARK OFFICE
CERTIFICATE OF CORRECTION

Page 1 of 1

PATENT NO. : 10,647,986 B2
APPLICATION NO. : 15/030127
DATED : May 12, 2020
INVENTOR(S) : Jocelyn Laporte, Belinda Cowling and Hichem Tasfaout It is certified that error appears in the above-identified patent and that said Letters Patent is hereby corrected as shown below:

In the Specification

Column 1,
Lines 1-5, "DYNAMIN 2 INHIBITOR FOR THE TREATMENT OF CENTRONUCLEAR MYOPATHIES

FIELD OF THE INVENTION"
Should read:
--DYNAMIN 2 INHIBITOR FOR THE TREATMENT OF CENTRONUCLEAR MYOPATHIES

CROSS-REFERENCE TO RELATED APPLICATION
This application is the U.S. national stage application of International Patent Application No. PCT/EP2014/072466, filed October 20, 2014.

FIELD OF THE INVENTION--.

Column 12,
Line 33, "Dynamin 2 The"
Should read:
--Dynamin 2. The--.

Column 14,
Line 2, "horning"
Should read:
--homing--.

Signed and Sealed this
Eighth Day of September, 2020

Andrei Iancu
*Director of the United States Patent and Trademark Office*